(12) United States Patent
Lee-Hoeflich et al.

(10) Patent No.: US 9,551,033 B2
(45) Date of Patent: Jan. 24, 2017

(54) GENE EXPRESSION MARKERS OF TUMOR RESISTANCE TO HER2 INHIBITOR TREATMENT

(75) Inventors: Si Tuen Lee-Hoeflich, Millbrae, CA (US); Howard Stern, San Carlos, CA (US)

(73) Assignee: Genentech, Inc., South San Francisco, CA (US)

(*) Notice: Subject to any disclaimer, the term of this patent is extended or adjusted under 35 U.S.C. 154(b) by 56 days.

(21) Appl. No.: 12/806,419

(22) Filed: Aug. 12, 2010

(65) Prior Publication Data

US 2011/0151454 A1 Jun. 23, 2011

Related U.S. Application Data

(63) Continuation-in-part of application No. 12/599,380, filed as application No. PCT/US2008/065766 on Jun. 4, 2008, now abandoned.

(60) Provisional application No. 60/942,906, filed on Jun. 8, 2007.

(51) Int. Cl.
*A61K 39/395* (2006.01)
*G01N 33/574* (2006.01)
*C12Q 1/68* (2006.01)

(52) U.S. Cl.
CPC ....... *C12Q 1/6886* (2013.01); *C12Q 2600/106* (2013.01); *C12Q 2600/112* (2013.01); *C12Q 2600/136* (2013.01); *C12Q 2600/178* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 4,935,341 A | 6/1990 | Bargmann | |
| 4,968,603 A | 11/1990 | Slamon | |
| 5,288,477 A | 2/1994 | Bacus | |
| 5,401,638 A | 3/1995 | Carney | |
| 5,514,554 A | 5/1996 | Bacus | |
| 5,571,894 A | 11/1996 | Wels | |
| 5,587,458 A | 12/1996 | King | |
| 5,604,107 A | 2/1997 | Carney | |
| 5,648,237 A | 7/1997 | Carter | |
| 5,677,171 A | 10/1997 | Hudziak | |
| 5,705,157 A | 1/1998 | Greene | |
| 5,720,937 A | 2/1998 | Hudziak | |
| 5,720,954 A | 2/1998 | Hudziak | |
| 5,725,856 A | 3/1998 | Hudziak | |
| 5,747,261 A | 5/1998 | King | |
| 5,770,195 A | 6/1998 | Hudziak | |
| 5,772,997 A | 6/1998 | Hudziak | |
| 5,783,186 A | 7/1998 | Arakawa | |
| 5,783,404 A | 7/1998 | Koski | |
| 5,804,396 A | 9/1998 | Plowman | |
| 5,824,311 A | 10/1998 | Greene | |
| 5,837,243 A | 11/1998 | Deo | |
| 5,846,749 A | 12/1998 | Slamon | |
| 5,856,089 A | 1/1999 | Wang | |
| 5,877,305 A | 3/1999 | Huston | |
| 5,910,486 A | 6/1999 | Curiel | |
| 5,922,845 A | 7/1999 | Deo | |
| 5,925,519 A | 7/1999 | Jensen | |
| 5,939,531 A | 8/1999 | Wels | |
| 5,977,322 A | 11/1999 | Marks | |
| 5,985,553 A | 11/1999 | King | |
| 5,994,071 A | 11/1999 | Ross | |
| 6,015,567 A | 1/2000 | Hudziak | |
| 6,028,059 A | 2/2000 | Curiel | |
| 6,054,297 A | 4/2000 | Carter | |
| 6,123,939 A | 9/2000 | Shawver | |
| 6,127,526 A | 10/2000 | Blank | |
| 6,165,464 A | 12/2000 | Hudziak | |
| 6,214,388 B1 | 4/2001 | Benz | |
| 6,267,958 B1 | 7/2001 | Andya | |
| 6,270,765 B1 | 8/2001 | Deo | |
| 6,333,169 B1 | 12/2001 | Hudziak | |
| 6,333,348 B1 | 12/2001 | Vogel | |
| 6,333,398 B1 | 12/2001 | Blank | |
| 6,339,142 B1 | 1/2002 | Basey | |
| 6,358,682 B1 | 3/2002 | Jaffee | |
| 6,387,371 B1 | 5/2002 | Hudziak | |
| 6,395,272 B1 | 5/2002 | Deo | |
| 6,399,063 B1 | 6/2002 | Hudziak | |
| 6,403,630 B1 | 6/2002 | Dannenberg | |
| 6,407,213 B1 | 6/2002 | Carter | |
| 6,417,335 B1 | 7/2002 | Basey | |
| 6,458,356 B1 | 10/2002 | Arakawa | |
| 6,489,447 B1 | 12/2002 | Basey | |

(Continued)

FOREIGN PATENT DOCUMENTS

EP 656367 A1 6/1995
EP 412116 B1 11/1995

(Continued)

OTHER PUBLICATIONS

Tan et al (Modern Pathology, 2005, 18:374-381).*
ADAPT, The Patterson Institute for Cancer Research, website for probesets for ERBB2, printed Nov. 20, 2012.*
Rouzier et al (Clinical Cancer research, 2005, 11:5678-5685).*
Harris et al (Clinical Cancer Research, Feb. 15, 2007, 13:1198-1207).*
ADAPT, The Patterson Institute for Cancer Research, website for probesets for PPM1H, printed Nov. 20, 2012.*
Chorn (Oncology Nursing Forum, 2006, 33:265-272), first page ONLY.*
Aasland et al. *Br. J, Cancer* 57:358-363 (1988).
Agus et al. *Cancer Cell* 2:127-37 (2002).
Agus et al. *Pro Am Soc Clin. Oncol.* 22:192 (2003).
Allison et al. *Pro Am Soc Clin. Oncol.* 22:197 (2003).
Arteaga et al. *Cancer Res.* 54:3758-3765 (1994).
Bacus et al. *Cancer Research* 52:2580-2589 (1992).
Bacus et al. *Molecular Carcinogenesis* 3:350-362 (1990).
Baselga et al., *Cancer Res.* 58:2825-2831 (1998).

(Continued)

*Primary Examiner* — Laura B Goddard
(74) *Attorney, Agent, or Firm* — Diane Marschang; Ginger R. Dreger; Arnold & Porter LLP

(57) ABSTRACT

The present invention concerns markers of resistance of HER2 expressing tumors to treatment with HER2 inhibitors, such as HER2 antibodies, including trastuzumab.

20 Claims, 38 Drawing Sheets

(56) References Cited

U.S. PATENT DOCUMENTS

| | | |
|---|---|---|
| 6,512,097 B1 | 1/2003 | Marks |
| 6,573,043 B1 | 6/2003 | Cohen |
| 6,582,919 B2 | 6/2003 | Danenberg |
| 6,602,670 B2 | 8/2003 | Danenberg |
| 6,627,196 B1 | 9/2003 | Baughman |
| 6,632,979 B2 | 10/2003 | Erickson |
| 6,685,940 B2 | 2/2004 | Andya |
| 6,719,971 B1 | 4/2004 | Carter |
| 6,767,541 B2 | 7/2004 | Slamon |
| 6,797,814 B2 | 9/2004 | Blank |
| 6,800,738 B1 | 10/2004 | Carter |
| 6,821,515 B1 | 11/2004 | Cleland |
| 6,905,830 B2 | 6/2005 | Cohen |
| 6,949,245 B1 | 9/2005 | Sliwkowski |
| 2002/0031515 A1 | 3/2002 | Caligiuri |
| 2002/0051785 A1 | 5/2002 | Slamon |
| 2002/0064785 A1 | 5/2002 | Mass |
| 2002/0076408 A1 | 6/2002 | Buchsbaum |
| 2002/0076695 A1 | 6/2002 | Ross |
| 2002/0090662 A1 | 7/2002 | Ralph |
| 2002/0141993 A1 | 10/2002 | Ashkenazi |
| 2002/0142328 A1 | 10/2002 | Danenberg |
| 2002/0155527 A1 | 10/2002 | Stuart |
| 2002/0192211 A1 | 12/2002 | Hudziak |
| 2002/0192652 A1 | 12/2002 | Danenberg |
| 2003/0022918 A1 | 1/2003 | Horak |
| 2003/0059790 A1 | 3/2003 | Jaffee |
| 2003/0068318 A1 | 4/2003 | O'Brien |
| 2003/0086924 A1 | 5/2003 | Sliwkowski |
| 2003/0103973 A1 | 6/2003 | Rockwell |
| 2003/0108545 A1 | 6/2003 | Rockwell |
| 2003/0134344 A1 | 7/2003 | Mass |
| 2003/0144252 A1 | 7/2003 | Furr |
| 2003/0147884 A1 | 8/2003 | Paton |
| 2003/0152572 A1 | 8/2003 | Homma |
| 2003/0152987 A1 | 8/2003 | Cohen |
| 2003/0157097 A1 | 8/2003 | Noguchi |
| 2003/0165840 A1 | 9/2003 | Danenberg |
| 2003/0170234 A1 | 9/2003 | Hellmann |
| 2003/0175845 A1 | 9/2003 | Kalbag |
| 2003/0190689 A1 | 10/2003 | Crosby |
| 2003/0202973 A1 | 10/2003 | Pieczenik |
| 2003/0211530 A1 | 11/2003 | Danenberg |
| 2003/0225528 A1 | 12/2003 | Baker et al. |
| 2003/0228663 A1 | 12/2003 | Lowman |
| 2004/0013297 A1 | 1/2004 | Taipei |
| 2004/0013667 A1 | 1/2004 | Kelsey |
| 2004/0024815 A1 | 2/2004 | Kawase |
| 2004/0082047 A1 | 4/2004 | Emery |
| 2004/0106161 A1 | 6/2004 | Bossenmaier |
| 2004/0138160 A1 | 7/2004 | Naito |
| 2004/0209290 A1 | 10/2004 | Cobleigh |
| 2004/0236078 A1 | 11/2004 | Carter |
| 2004/0258685 A1 | 12/2004 | Brunetta |
| 2005/0002928 A1 | 1/2005 | Hellmann |
| 2005/0037389 A1 | 2/2005 | Santin |
| 2005/0119288 A1 | 6/2005 | Bhattacharya |
| 2005/0208043 A1 | 9/2005 | Adams |
| 2005/0238640 A1 | 10/2005 | Sliwkowski |
| 2006/0034842 A1 | 2/2006 | Adams |
| 2006/0073143 A1 | 4/2006 | Adams |
| 2006/0127928 A1 | 6/2006 | Bacus et al. |
| 2006/0246470 A1 | 11/2006 | Fuqua et al. |
| 2006/0281122 A1 | 12/2006 | Bryant et al. |
| 2008/0052007 A1* | 2/2008 | Yu et al. .................. 702/20 |

FOREIGN PATENT DOCUMENTS

| | | |
|---|---|---|
| EP | 494135 B1 | 4/1996 |
| EP | 502812 B1 | 8/1996 |
| EP | 711565 | 8/1998 |
| EP | 554441 B1 | 1/1999 |
| EP | 616812 B1 | 11/1999 |
| EP | 1006194 A2 | 6/2000 |
| EP | 444181 B1 | 10/2001 |
| EP | 1357132 | 10/2003 |
| WO | WO 89/10412 | 11/1989 |
| WO | WO 91/02062 A2 | 2/1991 |
| WO | WO 91/05264 | 4/1991 |
| WO | WO 93/03741 A1 | 3/1993 |
| WO | WO 93/12220 A1 | 6/1993 |
| WO | WO 93/16185 A2 | 8/1993 |
| WO | WO 93/21232 A1 | 10/1993 |
| WO | WO 93/21319 A1 | 10/1993 |
| WO | WO 94/00136 A1 | 1/1994 |
| WO | WO 94/22478 A1 | 10/1994 |
| WO | WO 96/07321 A1 | 3/1996 |
| WO | WO 96/16673 A1 | 6/1996 |
| WO | WO 96/40789 A1 | 12/1996 |
| WO | WO 97/00271 A1 | 1/1997 |
| WO | WO 97/20858 A1 | 6/1997 |
| WO | WO 97/38731 A1 | 10/1997 |
| WO | WO 98/02463 A1 | 1/1998 |
| WO | WO 98/17797 A1 | 4/1998 |
| WO | WO 98/18489 A1 | 5/1998 |
| WO | WO 98/33914 A1 | 8/1998 |
| WO | WO 98/45479 A1 | 10/1998 |
| WO | WO 99/31140 A1 | 6/1999 |
| WO | WO 99/48527 A1 | 9/1999 |
| WO | WO 99/55367 A1 | 11/1999 |
| WO | WO 00/61145 A1 | 10/2000 |
| WO | WO 00/61185 A1 | 10/2000 |
| WO | WO 00/69460 A1 | 11/2000 |
| WO | WO 00/78347 A1 | 12/2000 |
| WO | WO 01/00238 A1 | 1/2001 |
| WO | WO 01/00244 A2 | 1/2001 |
| WO | WO 01/00245 A2 | 1/2001 |
| WO | WO 01/05425 A2 | 1/2001 |
| WO | WO 01/009187 A2 | 2/2001 |
| WO | WO 01/15730 A1 | 3/2001 |
| WO | WO 01/20033 A1 | 3/2001 |
| WO | WO 01/21192 A2 | 3/2001 |
| WO | WO 01/76586 A1 | 4/2001 |
| WO | WO 01/32155 A2 | 5/2001 |
| WO | WO 01/53354 A2 | 7/2001 |
| WO | WO 01/56604 A1 | 8/2001 |
| WO | WO 01/64246 A2 | 9/2001 |
| WO | WO 01/76630 A1 | 10/2001 |
| WO | WO 01/87334 A1 | 11/2001 |
| WO | WO 01/87336 A1 | 11/2001 |
| WO | WO 01/89566 A1 | 11/2001 |
| WO | WO 01/94626 A1 | 12/2001 |
| WO | WO 02/05791 A2 | 1/2002 |
| WO | WO 02/09754 A1 | 2/2002 |
| WO | WO 02/11677 A2 | 2/2002 |
| WO | WO 02/30268 | 4/2002 |
| WO | WO 02/44413 A2 | 6/2002 |
| WO | WO 02/45653 A2 | 6/2002 |
| WO | WO 02/055106 A2 | 7/2002 |
| WO | WO 02/070008 A1 | 9/2002 |
| WO | WO 02/087619 A1 | 11/2002 |
| WO | WO 02/089842 A1 | 11/2002 |
| WO | WO 03/006509 A2 | 1/2003 |
| WO | WO 03/012072 A2 | 2/2003 |
| WO | WO 03/028638 A2 | 4/2003 |
| WO | WO 03/040404 A1 | 5/2003 |
| WO | WO 03/041736 A2 | 5/2003 |
| WO | WO 03/078662 A1 | 9/2003 |
| WO | WO 03/86467 A1 | 10/2003 |
| WO | WO 03/087131 A2 | 10/2003 |
| WO | WO 2004/008099 A2 | 1/2004 |
| WO | WO 2004/004866 A2 | 3/2004 |
| WO | WO 2004/021010 A2 | 3/2004 |
| WO | WO 2004/041216 | 5/2004 |
| WO | WO 2004/048525 A2 | 6/2004 |
| WO | WO 2004/053497 A2 | 6/2004 |
| WO | WO 2004/063709 A2 | 7/2004 |
| WO | WO 2004/065545 | 8/2004 |
| WO | WO 2004/065583 A2 | 8/2004 |
| WO | WO 2004/000094 A2 | 12/2004 |
| WO | WO 2005/004432 A1 | 1/2005 |
| WO | WO 2005/016347 A1 | 2/2005 |
| WO | WO 2005/044091 | 5/2005 |

(56) References Cited

FOREIGN PATENT DOCUMENTS

| WO | WO 2006/026313 A2 | 3/2006 |
| WO | WO 2006/063042 | 6/2006 |
| WO | WO 2006/110593 A2 | 10/2006 |

OTHER PUBLICATIONS

Baselga et al., *J. Clin. Oncol.* 14:737-744 (1996).
Borst et al, *Gynecol. Oncol.*, 38:364 (1990).
Cho et al. *Nature* 421:756-60 (2003).
Cohen et al., *Oncogene*, 4:81-88 (1989).
Cronin et al. *Am. J. Path.* 164(1): 35-42 (2004).
Disouza et al. *Proc. Nail. Acad. Sci.* 91:7202-7206 (1994).
Drebin et al. *Oncogene* 2:273-277 (1988).
Drebin et al., *Cell* 41:695-706 (1985).
Fendly et al. *Cancer Research* 50:1550-1558 (1990).
Fukushige et al., *Mol Cell Biol.*, 6:955-958 (1986).
Gu et al. *Cancer Letters.* 99:185-9 (1996).
Guerin et al, *Oncogene Res.*,3:21-31 (1988).
Hancock et al. *Cancer Res.* 51:4575-4580 (1991).
Harari and Yarden *Oncogene* 19:6102-14 (2000).
Harwerth et al. *J. Biol. Chem.* 267:15160-15167 (1992).
Hudziak ei al., *Mol. Cell. Biol.* 9(3):1165-1172 (1989).
Kasprzyk et al. *Cancer Research* 52:2771-2776 (1992).
Kern et al., *Cancer Res.*, 50:5184 (1990).
King et al, *Science*, 229:974 (1985).
Klapper et al. *Oncogene* 14:2099-2109 (1997).
Kotts et al. In *Vitro* 26(3):59A (1990).
Kumar et al. *Mol. Cell. Biol.* 11(2):979-986 (1991).
Lee et al., *Nature* 378:394-396 (1995).
Lewis et al. *Cancer Research* 56:1457-1465 (1996).
Lewis et al. *Cancer Immunol. Immunoiher.* 37:255-263 (1993).
Ma et al. *Cancer Cell* 5:607-616 (2004).
Maier et al. *Cancer Res.* 51:5361-5369 (1991.
Malik et al. *Pro Am Soc Cancer Res* 44:176-7 (2003).
McCann et al, *Cancer*, 65:88-92 (1990).
McKenzie et al. *Oncogene* 4:543-548 (1989).
Myers et al., *Meth. Enzym.* 198:277-290 (1991).
Park et al., *Cancer Res.*, 49:6605 (1989).
Pietras el al. *Oncogene* 9:1829-1838 (1994).
Press et al., *Cancer Res.* 53:4960-4970 (1993).
Romond et al., *N Engl. IMed* 353:1673-1684 (2005).
Ross et al. *Hum. Pathol.* 28:827-33 (1997).
Ross et al. *Cancer* 79:2162-70 (1997).
Sadasivan et al. *J. Urol.* 150:126-31 (1993).
Sarup et al. *Growth Regulation* 1:72-82 (1991).
Schaefer et al. *Oncogene* 15:1385-1394 (1997).
Scott et al. *J. Biol. Chem.* 266:14300-5 (1991).
Shawver et al. *Cancer Res.* 54:1367-1373 (1994).
Shepard et al. *J Clin. Immunol.* 11(3):117-127 (1991).
Slamon et al., *Science*, 235:177-182 (1987).
Slamon et al., *N. Engl. J. Med.* 344:783-792 (2001).
Slamon et al., *Science*, 244:707-712 (1989).
Sliwkowski et al. *J. Biol. Chem.* 269(20):1466114665 (1994).
Sliwkowski *Nat. Struct. Biol.* 10:158-9 (2003).
Stancovski et al. *IWAS (USA)* 88:8691-8695 (1991).
Tagliabue et al. *Int. Cancer* 47:933-937 (1991).
Vitctta et al. *Cancer Research* 54:5301-5309 (1994).
Weiner et al, *Cancer Res.*, 50:421-425 (1990).
Williams et al. *Pathobiology* 59:46-52 (1991).
Xu et al. *Int. J. Cancer* 53:401-408 (1993).
Yarden and Sliwkowski. *Nat Rev Mol Cell Biol.* 2:127-37 (2001).
Yokota et at, *Lancet*: 1:765-767 (1986).
Yonemura et a/., *Cancer Res.*, 51:1034 (1991).
Zhau et al., *Mol. Carcinog.*, 3:254-257 (1990).
Agazie et al. "Molecular mechanism for a role of SHP2 in epidermal growth factor receptor signaling", Molecular and Cellular Biology, 23(21) 7875-7886, 2003.
Bentires-Alj et al. "A role for the scaffolding adapter GAB2 in breast cancer", Nature Medicine, 12(1) 114-121, 2005.
Mohi et al. "The role of SHP2(PTPN11) in cancer", Current Opinion Genetics 17(1)23-30,2007.
Su et al. "HER-2/neu raises SHP-2, stops IFN-gamma anti-proliferation in bladder cancer", Biochemical and Biophysical Research Communications 356(1)181-186, 2007.
European Search Report dated Jul. 11, 2013, cited in copending EP Application No. 12194103.3.
Hamel et al. "Molecular determinants of resistance to trastuzumab in breast cancer", Proceedings of the American Association Cancer Res. 48:555, 2007.
Mukhopadhyay et al. "Upregulation and targeting of chemokine receptor CXCR4 in acquired trastuzumab resistance", Proceedings of the American Association Cancer Res. 48:555, 2007.
Nagata et al. "PTEN activation contributes to tumor inhibition by trastuzumab, and loss of PTEN predicts trastuzumab resistance in patients", Cancer Cell vol. 6:117-127, 2004.
Rennstam et al. "Cytogenetic characterization and gene expression profiling of the trastuzumab-resistant breast cancer cell line JIMT-1", Cancer Genetics Cytogenetics 172 (2)95-106, 2007.
Ring et al. "Predictors of response to systemic therapy in breast cancer", Forum Trends in Experimental and Clinical Medicine 12 (1)19-32, 2002.
Robert et al. "Predicting drug response based on gene expression", Criticals Review in Oncology/Hematology 51(3)205-227, 2004.
Ross et al. "Breast cancer biomarkers and molecular medicine", Expert Rev. Mol. Diagn. 3(5) 573-583, 2003.
European Search Report dated Apr. 4, 2013, cited in copending EP Application No. 12194103.3.
Affymetrix "Gene chip human genome U133 arrays", Technical Bulletin Part No. 701484 Rev. 4 available on line at http://www.affymetrix.com/catalog/131455/AFFY/Human-Genome-U133-Plus-2.0-Affay#1_3, 2003.
Fan et al. "Concordance among gene-expression based predictors for breast cancer", New England Journal Medicine 355(6):560-569, Aug. 2006.
Sorlie et al. "Gene expression patterns of breast carcinomas distinguish tumor subclasses with clinical implications", Pro. Natl. Acad. Sci. 98(19):10869-10874, Sep. 2001.
Chandramouli et al., "Haploinsufficiency of the *cdc21* gene contributes to skin cancer development in mice," Carcinogenesis 2007, vol. 28, No. 9, pp. 2028-2035.

* cited by examiner

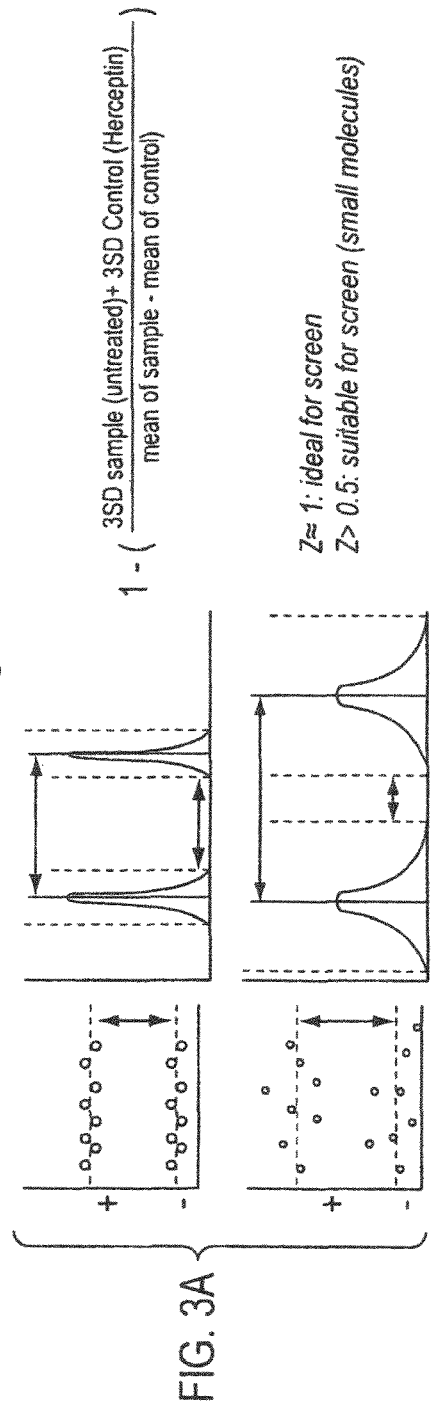
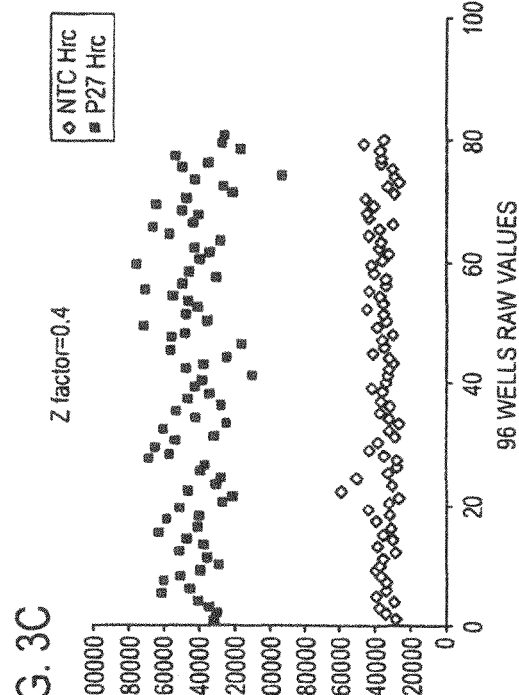
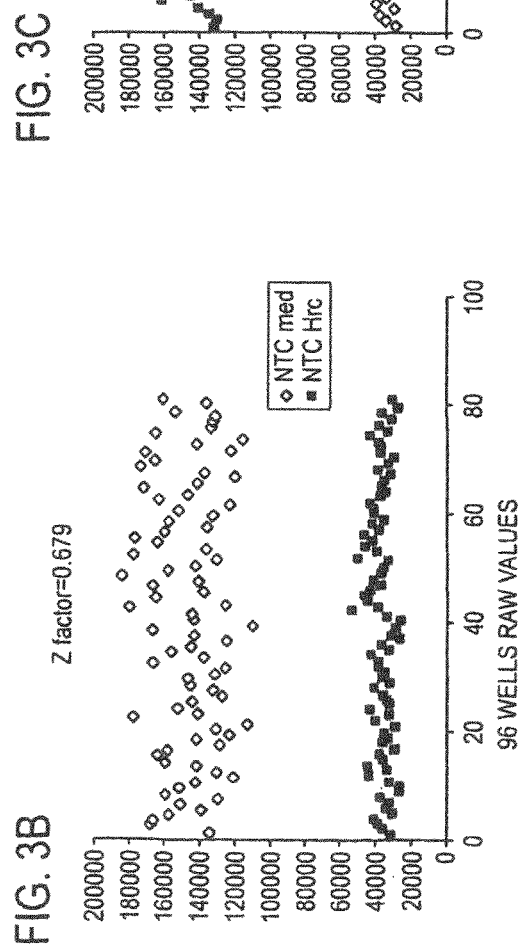
FIG. 3A
FIG. 3B
FIG. 3C

Summary of the Phosphatase Library Screen

| normalization | Li analysis z>1.5 | | | Raw values analysis | |
|---|---|---|---|---|---|
| | ave | pos | neg | | Nil |
| PTEN | 3 | 1 | 1 | | 3 |
| PTPN11 | 2 | 2 | 2 | | 3 |
| PPP2R1A | 1* | 2 | 3 | | 3 |
| KIAA0685 | 2 | 2 | 2 | | 2 |
| PPM1H | 2 | 2 | 2 | | 2 |
| SSH3 | 1 | 2 | 2 | | 2 |
| MTMR3 | 1 | 2 | 2 | | 1 |
| PPP2R2B | 0 | 2 | 1 | | 1 |
| PTENP1 | 2 | 1 | 1 | | 2 |
| KIF1B | 2 | 0 | 0 | | 2 |
| MPHOSPH1 | 2 | 0 | 0 | | 2 |

2 or 3 oligo hits (disregard of mix results) = 11 (5.5% of the library)
2 oligo hits (in all analysis) = 3 (1.5% of the library)
* Average of plate is obscured due to one high data point ≥3 oligo hits or 2 oligos + pool Data analysis by plotting raw values of the screen showed P27 is a 4 oligo hit

Combine Analysis of Kinase Library Hits

\* 2 oligo hits in some but not all normalized analysis

Result from the Kinase Library Screen

| Known/putative functions | examples | hits |
|---|---|---|
| Cell cycle regulation | CDKs, RhoGTPases/ cytoskeleton | 6 (2 oligo hits) 1 (3 oligo hits) |
| Key downstream Signaling pathways | MAPKs, PI 3/4 kinase | 7 (2 oligo hits) 1 (3 oligo hits) |
| Less Characterized pathways | Metabolic pathways, PKC, KAK-STAT, Wnt | 5 (2 oligo hits) |
| Others | Novel genes, unrelated pathways | 7 (2 oligo hits) 1 (3 oligo hits) |

FIG. 8

Development of the Secondary Screen

*P27=oligo2*

Combined analysis of the screens

| Gene | 1st screen # oligo hits | (oligos) | Validation screen # oligo hits | (oligos) | SKBR3 # oligo hits | (oligos) |
|---|---|---|---|---|---|---|
| CDK11 | 2 | (2,3) | 2 | (2,3) | 1 | (,2) |
| DKFZP586B16 | 2 | (2,3) | 2+P | (2,3) | 0 | 0 |
| DGKI | 2 | (2,3) | 2+P | (2,3) | 1 | (,2) |
| DUSP4 | 2 | (1,4) | 2 | (1,4) | 1+P | (,1) |
| DUSP6 | 2 | (2,4) | 2 | (2,4) | 1 | (,1) |
| DYRK1A | 2 | (1,4) | 4+P | (1,2,3,4) | 4+P | (1,2,3,4) |
| FLJ35107 | 2 | (1,2) | 2 | (1,2) | 1 | (,2) |
| FLT1 | 3 | (1,2,3) | 4+P | (1,2,3,4) | 2 | (2,4) |
| HIPK3 | 2 | (3,4) | 1 | (,3) | 0 | 0 |
| HK2 | 2 | (1,4) | 3 | (1,2,4) | 3 | (1,2,4) |
| ITK | 2 | (1,2) | 2 | (1,2) | 1 | (,2) |
| MOAP1/ITPK1 | 2 | (3,4) | 1 | (,4) | 1 | (,3) |
| KIAA1639 | 3 (4) | (1,2,3, 4?) | 3+P | (1,3,4) | 2 | (1,3) |
| LATS2 | 2(3) | (1,3, 4?) | 3+P | (1,3,4) | 0 | 0 |
| LIM/PDLIM5 | 2 | (1,2) | 2+P | (1,2) | 0 | 0 |
| MAPK8/JNK | 2 | (1,3) | 1 | (,1) | 0 | 0 |
| MAP4K4 | 2 | (1,2) | 2 | (1,2) | 2 | (1,2) |
| PANK1 | 2 | (1,3) | 3 | (2,3,4) | 1+P | (,1) |
| PI4K2B | 2 (3) | (1,2 4?) | 2 | (2,4) | 1 | (,2) |
| PRKWNK3 | 2 | (2,4) | 2+P | (2,4) | 0 | 0 |
| RYK | 2 | (1,4) | 2 | (1,4) | 0 | 0 |
| SPEC2 | 2 | (3,4) | 2 | (3,4) | 2+P | (2,4) |
| Socs5 | 2 | (1,3) | 2 | (1,3) | 4+P | (1,2,3,4) |
| STK10 | 2 | (1,2) | 4+P | (1,2,3,4) | 3 | (2,3,4) |
| STK22C | 2 | (1,4) | 3+P | (1,3,4) | 2+P | (3,4) |
| STYK1/NOV* | 2 | (1,2) | 3+P | (1,2,4) | 0 | 0 |
| TXND3 | 2 | (1,3) | 2 | (1,3) | 2 | (1,2) |
| Wee1 | 2 | (1,2) | 2 | (1,2) | 0 | 0 |

FIG. 10

Summary of the Phosphatase Library Screen

|  | Li analysis z>1.5 | | | Raw values analysis |
|---|---|---|---|---|
| normalization | ave | pos | neg | Nil |
| PTEN | 3 | 1 | 1 | 3 |
| PTPN11 | 2 | 2 | 2 | 3 |
| PPP2R1A | 1* | 2 | 3 | 3 |
| KIAA0685 | 2 | 2 | 2 | 2 |
| PPM1H | 2 | 2 | 2 | 2 |
| SSH3 | 1 | 2 | 2 | 2 |
| MTMR3 | 1 | 2 | 2 | 1 |
| PPP2R2B | 0 | 2 | 1 | 1 |
| PTENP1 | 2 | 1 | 1 | 2 |
| KIF1B | 2 | 0 | 0 | 2 |
| MPHOSPH1 | 2 | 0 | 0 | 2 |

2 or 3 oligo hits (disregard of mix results) = 11 (5.5% of the library)
2 oligo hits (in all analysis) = 3 (1.5% of the library)
*Average of plate is obscured due to one high data point

FIG. 11

Top Hits Based on Strongest Phenotype and >2 Oligo Hit

| | | | |
|---|---|---|---|
| 1 | PPM1H | 3+P strong | UNQ11299 |
| 2 | DYRK1A | 4+P strong | UNQ3880 |
| 3 | STK10 | 4+P strong | UNQ4026 |
| 4 | PTPN11* | 2+P | UNQ7397 |

*PTPN11 was included despite being only a 2 oligo hit because of a known link to HER2-PI3K/Akt signaling

FIG. 13

Examples of how top hits augment cell proliferation in BT474 cells treated with Herceptin Examples of how top hits augment cell proliferation in BT474-M1 cells treated with Herceptin Knockdown of candidate genes also attenuates lapatinib response in mutiple cell lines (PPM1H in particular)

| Summary | Cell lines | | |
|---|---|---|---|
| Genes | M1 | HCC1419 | SKBR3 |
| PTEN | + | - | +/- |
| P27 | + | + | - |
| PPM1H | + | + | + |
| PTPN11 | + | - | N/D |
| STK10 | -/+ | + | N/D |
| DYRK1A | - | -/+ | N/D |

+ significant decreased of Lapatinib response
+/- moderate decreased of Lapatinib response

| gene | # oligos worked Primary | Validation | SKBR3 | ccession number |
|---|---|---|---|---|
| CDK11 | 2 | 2 | | NM_015076 |
| DYRK1A | 2 | 4+P | * | NM_001396 |
| LATS2 | 2-3 | 3+P | | NM_014572 |
| STK10 | 2 | 4+P | * | NM_005990 |
| Wee1 | 2 | 2 | | NM_003390 |
| DUSP4 | 2 | 2 | | NM_001394 |
| DUSP6 | 2 | 2 | | NM_001946 |
| HIPK3 | 2 | 1 | | NM_005734 |
| JNK | 2 | 1 | | NM_002752 |
| MAP4K4 | 2 | 2 | | NM_004834 |
| PTPN11 | 2-3 | 3+P | * | NM_002834 |
| Socs5 | 2 | 2 | ** | NM_014011 |
| PPM1H | 2-3 | 3+P | * | NM_051093 |
| DKFZP586B16 | 2 | 2+P | | NM_015533 |
| DGKI | 2 | 2+P | | NM_004717 |
| FLJ35107 | 2 | 2 | | NM_496631 |
| FLT1 | 3 | 4+P | | NM_002019 |
| HK2 | 2 | 3 | * | NM_000189 |
| ITK | 2 | 2 | | NM_005546 |
| MOAP1 | 2 | 1 | | NM_014216 |
| KIAA0685 | 2 | 1+P | | NM_014678 |
| KIAA1639 | 3-4 | 3+P | * | NM_290923 |
| LIM/PDLIM5 | 2 | 2+P | | NM_006457 |
| PANK1 | 2 | 3 | | NM_138316 |
| PI4K2B | 2-3 | 2 | | NM_018323 |
| PPP2R1A | 2-3 | 2+P | | NM_014225 |
| PRKWNK3 | 2 | 2+P | | NM_020922 |
| RYK | 2 | 2 | | NM_002958 |
| SPEC2 | 2 | 2 | | NM_020240 |
| STK22C | 2 | 3+P | * | NM_052841 |
| STYK1 | 2 | 3+P | | NM_018423 |
| TXND3 | 2 | 2 | * | NM_016616 |

* 2 or more oligo hits in SKBR3 cell line functions
  Blue: cell cycle
  Green: Erk/MARK pathway
  Red: Post-translation modification

FIG. 33

Summary

| Gene | Cell lines<br>Lower expression in Basal | Tissue<br>Lower expression in Basal |
|---|---|---|
| PTEN | Y | Y |
| CDKN1B | Y | Y |
| PPM1H | Y | Y |
| PTPN11 | Y | Y |
| DYRK1A | N | N |
| STK10 | N | N |
| PPM1A | Y | Y |
| PPM1B | N | N |
| ILKAP | N | N |
| PPM1M | N | N |
| PPM1J | Y | Y |

FIG. 34

|  | Refseq |
|---|---|
| CDKN1B | NM_004064 |
| DYRK1A | NM_001396 |
| TNNI3K | NM_015978 |
| DUSP4 | NM_001394 |
| ATR | NM_001184 |
| BCR | NM_004327 |
| BMPR1A | NM_004329 |
| CDK11 | NM_015076 |
| DKFZP586B1 | NM_015533 |
| CDC2L2 | NM_024011 |
| DUSP6 | NM_001946 |
| STYK1 | NM_018423 |
| DGKI | NM_004717 |
| KIAA1639 | NM_290923 |
| FLJ35107 | NM_496631 |
| LIM | NM_006457 |
| MARK8 | NM_002750 |
| FLT1 | NM_002019 |
| ITPK1 | NM_014216 |
| HK2 | NM_000189 |
| ITK | NM_005546 |
| MAP4K4 | NM_004834 |
| LATS2 | NM_014572 |
| SPEC2 | NM_020240 |
| EXOSC10 | NM_002685 |
| PRKWNK3 | NM_020922 |
| PI4K2B | NM_018323 |
| STK22C | NM_052841 |
| STK10 | NM_005990 |
| PANK1 | NM_138316 |
| SOCS5 | NM_014011 |
| RYK | NM_002958 |
| PDK3 | NM_005391 |
| PRKD2 | NM_016457 |
| TXNDC3 | NM_016616 |
| WEE1 | NM_003390 |
| PPM1H | NM_051093 |
| PPP2R1A | NM_014225 |
| PPP2R2B | NM_004576 |
| MTMR3 | NM_021090 |
| PTPN11 | NM_002834 |
| SSH3 | NM_017857 |

FIG. 35

GENE EXPRESSION MARKERS OF TUMOR RESISTANCE TO HER2 INHIBITOR TREATMENT

CROSS-REFERENCE TO RELATED APPLICATIONS

This application is a continuation-in-part application of U.S. patent application Ser. No. 12/599,380, filed Feb. 22, 2010, which is a National Stage Application under 37 C.F.R. 371 of International Application No. PCT/US2008/065766, filed Jun. 4, 2008, and claims priority under 35 U.S.C. Section 119(e) and the benefit of U.S. Provisional Application Ser. No. 60/942,906 filed Jun. 8, 2007, the contents of which are incorporated herein by reference in their entireties.

FIELD OF THE INVENTION

The present invention concerns markers of resistance of HER2 expressing tumors to treatment with HER2 inhibitors, such as HER2 antibodies, including trastuzumab.

DESCRIPTION OF THE RELATED ART

HER receptors and HER antibodies

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2).

The second member of the HER family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science*, 235:177-182 (1987); Slamon et al., *Science*, 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science*, 229:974 (1985); Yokota et al., *Lancet:* 1:765-767 (1986); Fukushige et al., *Mol Cell Biol.*, 6:955-958 (1986); Guerin et al., *Oncogene Res.*, 3:21-31 (1988); Cohen et al., *Oncogene*, 4:81-88 (1989); Yonemura et al., *Cancer Res.*, 51:1034 (1991); Borst et al., *Gynecol. Oncol.*, 38:364 (1990); Weiner et al., Cancer Res., 50:421-425 (1990); Kern et al., *Cancer Res.*, 50:5184 (1990); Park et al., *Cancer Res.*, 49:6605 (1989); Zhau et al., *Mol. Carcinog.*, 3:254-257 (1990); Aasland et al. *Br. J. Cancer* 57:358-363 (1988); Williams et al. *Pathobiology* 59:46-52 (1991); and McCann et al., *Cancer,* 65:88-92 (1990). HER2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Antibodies directed against the rat p185$^{neu}$ and human HER2 protein products have been described.

Drebin and colleagues have raised antibodies against the rat neu gene product, p185$^{neu}$ See, for example, Drebin et al., *Cell* 41:695-706 (1985); Myers et al., *Meth. Enzym.* 198: 277-290 (1991); and WO94/22478. Drebin et al. *Oncogene* 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α. See also U.S. Pat. No. 5,677,171 issued Oct. 14, 1997. The HER2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. Mol. Cell. Biol. 11(2): 979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized version of the murine HER2 antibody 4D5 (huMAb4D5-8, rhuMAb HER2, trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration Sep. 25, 1998 for the treatment of patients with metastatic breast cancer whose tumors overexpress the HER2 protein. In November 2006, the FDA approved HERCEPTIN® (trastuzumab) as part of a treatment regimen containing doxorubicin, cyclophosphamide and paclitaxel, for the adjuvant treatment of patients with HER2-positive, node-positive breast cancer. See also, Press et al., *Cancer Res.* 53:4960-4970 (1993); Baselga et al., *Cancer Res.* 58:2825-2831 (1998); Pegram et al., *Proc. Am. Assoc. Cancer* 38:602 (1997), Abstract 4044; Slamon et al., *N. Engl. J. Med.* 344:783-792(2001); Lee et al., *Nature* 378:394-396 (1995); Romond et al., *N. Engl. J. Med.* 353:1673-1684 (2005); Ta-Chiu et al., *J. Clin. Oncol.* 7811-7819 (2005).

Other HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765

(1994); Harwerth et al. *J. Biol. Chem.* 267:15160-15167 (1992); U.S. Pat. No. 5,783,186; and Klapper et al. *Oncogene* 14:2099-2109 (1997).

Additional patent publications related to HER antibodies include: U.S. Pat. Nos. 5,677,171, 5,720,937, 5,720,954, 5,725,856, 5,770,195, 5,772,997, 6,165,464, 6,387,371, 6,399,063, US2002/0192211A1, U.S. Pat. Nos. 6,015,567, 6,333,169, 4,968,603, 5,821,337, 6,054,297, 6,407,213, 6,719,971, 6,800,738, US2004/0236078A1, U.S. Pat Nos. 5,648,237, 6,267,958, 6,685,940, 6,821,515, WO98/17797, U.S. Pat. Nos. 6,127,526, 6,333,398, 6,797,814, 6,339,142, 6,417,33, 6,489,447, WO99/31140, US 2003/0147884A1, US 2003/0170234A1, US2005/0002928A1, U.S. Pat Nos. 6,573,043, US2003/0152987A1, WO99/48527, US2002/0141993A1, WO01/00245, US2003/0086924, US2004/0013667A1, WO00/69460, WO01/00238, WO01/15730, U.S. Pat. Nos. 6,627,196B1, U.S Pat. No. 6,632,979B1, WO01/00244, US2002/0090662A1, WO01/89566, US2002/0064785, US2003/0134344, WO 04/24866, US2004/0082047, US2003/0175845A1, WO03/087131, US2003/0228663, WO2004/008099A2, US2004/0106161, WO2004/048525, US2004/0258685A1, U.S. Pat. Nos. 5,985,553, 5,747,261, 4,935,341, 5,401,6, 5,604,107, WO 87/07646, WO 89/10412, WO 91/05264, EP 412,116 B1, EP 494,135 B1, U.S Pat No. 5,824,311, EP 444,181 B1, EP 1,006,194 A2, US2002/0155527A1, WO 91/02062, U.S. Pat. Nos 5,571,894, 5,939,531, EP 502,812 B1, WO 93/03741, EP 554,441 B1, EP 656,367 A1, U.S Pat. Nos. 5,288,477, 5,514,554, 5,587,458, WO 93/12220, WO 93/16185, U.S. Pat No 5,877,305, WO 93/21319, WO 93/21232, U.S. Pat. No. 5,856,089, WO 94/22478, U.S. Pat. No. 5,910,486, 6,028,059, WO 96/07321, U.S. Pat. Nos. 5,804,396, 5,846,749, EP 711,565, WO 96/16673, U.S. Pat. Nos. 5,783,404, 5,977,322, 6,512,097, WO 97/00271, U.S. Pat. Nos 6,270,765, 6,395,272, 5,837,243, WO 96/40789, U.S. Pat. Nos. 5,783,186, 6,458,356, WO 97/20858, WO 97/38731, U.S. Pat. Nos. 6,214,388, 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US2003/0211530A1, WO 02/44413, US2002/0142328, U.S. Pat. No. 6,602,670 B2, WO 02/45653, WO 02/055106, US2003/0152572, US2003/0165840, WO 02/087619, WO 03/006509, WO03/012072, WO 03/028638, US 2003/0068318, WO 03/041736, EP 1,357,132, US 2003/0202973, US 2004/138160, U.S. Pat. Nos. 5,705,157, 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842 and WO 03/86467.

U.S. Application Publication No. 2005010 (published May 12, 2005) and its PCT counterpart, WO 20054432, concern method for treating cancer, including lung cancer, bone cancer and ovarian cancer, with a combination of an ErbB2 ligand and an ErbB antibody.

U.S. Application Publication No. 20050119288 (published Jun. 2, 2005) and its PCT counterpart, WO 200516347, are directed to a method for treating overexpression of the erbB2 receptor by administering a therapeutically effective amount of a first inhibitor of the erbB2 receptor; and subsequently, after an interval comprising less than 24 hours, from one to six therapeutically effective amounts of a second inhibitor of the erbB2 receptor.

WO 2006026313, published Mar. 9, 2006, concerns method for treating cancer by administering 4-quinazolinamines, which are dual inhibitors of EGFR and ErbB2, in combination with at least one other ErbB family inhibitor.

HERCEPTIN® (trastuzumab) provides clinical benefit to a large percentage of patients diagnosed with HER2 positive breast cancer, both alone and in the adjuvant setting, in combination with chemotherapy. However, a significant number of HER2 positive patients exhibits either primary resistance or acquired resistance to treatment with trastuzumab. It is, therefore, a great need for identifying genes that might be involved in resistance to treatment with trastuzumab and other HER2 antibodies.

Pertuzumab (also known as recombinant human monoclonal antibody 2C4; OMNITARG™, Genentech, Inc., South San Francisco) represents the first in a new class of agents known as HER dimerization inhibitors (HDI) and functions to inhibit the ability of HER2 to form active heterodimers with other HER receptors (such as EGFR/HER1, HER3 and HER4) and is active irrespective of HER2 expression levels.

Pertuzumab blockade of the formation of HER2-HER3 heterodimers in tumor cells has been demonstrated to inhibit critical cell signaling, which results in reduced tumor proliferation and survival (Agus et al. *Cancer Cell* 2:127-37 (2002)).

Pertuzumab has undergone testing as a single agent in the clinic with a phase Ia trial in patients with advanced cancers and phase II trials in patients with ovarian cancer and breast cancer as well as lung and prostate cancer. In a Phase I study, patients with incurable, locally advanced, recurrent or metastatic solid tumors that had progressed during or after standard therapy were treated with pertuzumab given intravenously every 3 weeks. Pertuzumab was generally well tolerated. Tumor regression was achieved in 3 of 20 patients evaluable for response. Two patients had confirmed partial responses. Stable disease lasting for more than 2.5 months was observed in 6 of 21 patients (Agus et al. *Pro Am Soc Clin Oncol* 22:192 (2003)). At doses of 2.0-15 mg/kg, the pharmacokinetics of pertuzumab was linear, and mean clearance ranged from 2.69 to 3.74 mL/day/kg and the mean terminal elimination half-life ranged from 15.3 to 27.6 days. Antibodies to pertuzumab were not detected (Allison et al. *Pro Am Soc Clin Oncol* 22:197 (2003)).

DIAGNOSTICS

Patients treated with the HER2 antibody trastuzumab are selected for therapy based on HER2 overexpression/amplification. See, for example, WO99/31140 (Paton et al.), US2003/0170234A1 (Hellmann, S.), and US2003/0147884 (Paton et al.); as well as WO01/89566, US2002/0064785, and US2003/0134344 (Mass et al.). See, also, U.S. Pat. Nos. 6,573,043, 6,905,830, and US2003/0152987, Cohen et al., concerning immunohistochemistry (IHC) and fluorescence in situ hybridization (FISH) for detecting HER2 overexpression and amplification.

WO2004/053497 and US2004/024815A1 (Bacus et al.), as well as US 2003/0190689 (Crosby and Smith), refer to determining or predicting response to trastuzumab therapy. US2004/013297A1 (Bacus et al.) concerns determining or predicting response to ABX0303 EGFR antibody therapy. WO2004/000094 (Bacus et al.) is directed to determining response to GW572016, a small molecule, EGFR-HER2 tyrosine kinase inhibitor. WO2004/063709, Amler et al., refers to biomarkers and methods for determining sensitivity to EGFR inhibitor, erlotinib HCl. US2004/0209290 and WO04/065583, Cobleigh et al., concern gene expression markers for breast cancer prognosis. See, also, WO03/078662 (Baker et al.), and WO03/040404 (Bevilacqua et al.). WO02/44413 (Danenberg, K.) refers to determining EGFR and HER2 gene expression for determining a chemotherapeutic regimen.

Patients treated with pertuzumab can be selected for therapy based on HER activation or dimerization. Patent publications concerning pertuzumab and selection of patients for therapy therewith include: U.S. Pat. No. 6,949,245, WO01/00245, US2005/0208043, US2005/0238640, US2006/0034842, and US2006/0073143 (Adams et al.); US2003/0086924 (Sliwkowski, M.); US2004/0013667A1 (Sliwkowski, M.); as well as WO2004/008099A2, and US2004/0106161 (Bossenmaier et al.).

Cronin et al. *Am. J. Path.* 164(1): 35-42 (2004) describes measurement of gene expression in archival paraffin-embedded tissues. Ma et al. *Cancer Cell* 5:607-616 (2004) describes gene profiling by gene oliogonucleotide microarray using isolated RNA from tumor-tissue sections taken from archived primary biopsies.

SUMMARY OF THE INVENTION

In one aspect, the invention concerns a method of predicting the likelihood of response of a mammalian subject diagnosed with or at risk of developing a HER2 expressing tumor to treatment with a HER2 inhibitor, comprising determining, in a biological sample obtained from said subject, the expression level of RNA transcripts or their expression products of one or more genes selected from the group consisting of CDK11, DYRK1A, LATS2, STK10, Wee1, DUSP4, DUSP6, HIPK3, JNK, MAP4K4, PTPN11, Socs5, PPM1H, DKFZP586B16, DGKI, FLJ35107, FLT1, HK2, ITK, MOAP1, KIAA0685, KIAA1639, LIM/PDLIM5, PANK1, P14K2B, PPP2R1A, PRKWNK3, RYK, SPEC2, STK22C, STYK1, and TXND3, wherein a lower level of expression relative to one or more positive and/or negative controls indicates that the subject is likely to be resistant to treatment with the HER2 inhibitor.

The mammalian subject preferably is a human patient, such as a human cancer patient diagnosed with or at risk of developing a HER2 expressing cancer.

In various embodiments, the diagnosis includes quantification of the HER2 expression level, such as by immunohistochemistry (IHC) and/or fluorescence in situ hybridization (FISH).

In other embodiments, the cancer expresses HER2 at least at a 1+ level, or at least at a 2+ level, or at a 3+ level.

In another embodiment, the cancer is selected from the group consisting of breast cancer, squamous cell cancer, small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, and head and neck cancer.

In yet another embodiment, the cancer is selected from the group consisting of Overexpression of HER2 (frequently but not uniformly due to gene amplification) has also been observed in other carcinomas including carcinomas of the stomach, endometrium, salivary gland, lung, kidney, colon, thyroid, pancreas and bladder, and prostate cancer.

In still another embodiment, the cancer is breast cancer, such as metastatic breast cancer.

In various embodiments, the resistance to a HER2 inhibitor is determined by using one or more genes are selected from the group consisting of DYRKIA, HK2, Socs5, STK10, KIaa1639, and MAP4K4, and/or the group consisting of PTPN11, KIAA0685, and PPM1H.

The HER2 inhibitor may be an agent which interferes with HER2 activation or function.

HER 2 inhibitors include, without limitation, HER antibodies and antibody fragments, small molecule HER2 antagonists, HER2 tyrosine kinases inhibitors, and antisense molecules.

In one embodiment, the HER2 inhibitor is a HER2 antibody or antibody fragment, or a small molecule which binds to and inhibits the HER2 receptor.

In various embodiments, the HER2 antibody may inhibits HER2 ectodomain cleavage, may block ligand activation of a HER receptor, or may inhibit HER2 dimerization.

In another embodiment, the HER2 antibody binds to the heterodimeric binding site of HER2.

In yet another embodiment, the HER2 antibody or antibody fragment binds to the 4D5 epitope, and may, for example, be selected from the group consisting of humanized antibodies huMAb4D5-1, huMAb4D5-2, huMAb4D5-3, huMAb4D5-4, huMAb4D5-5, huMAb4D5-6, huMAb4D5-7 and trastuzumab, and fragments thereof.

In a preferred embodiment, the HER2 antibody is trastuzumab or a fragment thereof.

In a further embodiment, the HER2 antibody blocks ligand activation of a HER2 receptor more effectively than trastuzumab.

In a different embodiment, the HER2 antibody binds the 2C4 epitope, and may, for example, be pertuzumab or a fragment thereof.

In various embodiments, the biological sample is a tumor sample, such as a sample is from a fixed, wax-embedded cancer tissue specimen of a patient.

In another embodiment, the tumor sample is a core biopsy tissue.

In yet another embodiment, the biological sample is biological fluid, such as, for example, blood, urine, saliva, ascites fluid, blood serum or blood plasma.

In a further embodiment, determination of the expression level is implemented using an apparatus adapted to determine the expression levels of the transcripts or their expression products.

Determination of the expression levels may, for example, be performed by using a software program executed by a suitable processor, which may be embodied in software stored on a tangible medium. Representative but non-limiting examples of tangible media include a CD-ROM, a floppy disk, a hard drive, a DVD, and a memory associated with the processor.

In a further embodiment, the method of the present invention further comprises the step of preparing a report recording the results of said determination or the prediction.

In one embodiment, the report is recorded or stored on a tangible medium.

In another embodiment, the tangible medium is paper.

In yet another embodiment, the tangible medium is selected from the group consisting of a CD-ROM, a floppy disk, a hard drive, a DVD, and a memory associated with the processor.

In a further embodiment, the methods herein further comprise the step of communicating the results of the test to an interested party, such as the patient or the attending physician.

Communication may, for example, be in writing, by email, or by telephone.

In another aspect, the invention concerns an array comprising polynucleotides hybridizing to two or more, or at least 3, or at least 5 of the following genes: CDK11, DYRK1A, LATS2, STK10, Wee1, DUSP4, DUSP6, HIPK3, JNK, MAP4K4, PTPN11, Socs5, PPM1H, DKFZP586B16, DGKI, FLJ35107, FLT1, HK2, ITK, MOAP1, KIAA0685, KIAA1639, LIM/PDLIM5, PANK1, P14K2B, PPP2R1A, PRKWNK3, RYK, SPEC2, STK22C, STYK1, and TXND3.

In one embodiment, the array comprises polynucleotides hybridizing to all of the following genes: CDK11, DYRK1A, LATS2, STK10, Wee1, DUSP4, DUSP6, HIPK3, JNK, MAP4K4, PTPN11, Socs5, PPM1H, DKFZP586B16, DGKI, FLJ35107, FLT1, HK2, ITK, MOAP1, KIAA0685, KIAA1639, LIM/PDLIM5, PANK1, P14K2B, PPP2R1A, PRKWNK3, RYK, SPEC2, STK22C, STYK1, and TXND3.

In another embodiment, the array comprises polynucleotides hybridizing to all of the following genes: DYRK1A, HK2, Socs5, STK10, KIaa1639, and MAP4K4.

In yet another embodiment, the array comprises polynucleotides hybridizing to the following genes: PTPN11, KIAA0685, and PPM1H.

In yet another embodiment, the assay comprises polynucleotides hybridizing to PPM1H in the absence of polynucleotides hybridizing to any other marker.

BRIEF DESCRIPTION OF THE DRAWINGS

FIGS. 3A, 3B and 3C. Optimization of the screening window coefficient —Z factor.

FIG. 8. Results from the kinase library screen.

FIG. 10. Combined analysis of the screens.

FIG. 11. Summary of the phosphatase library screen.

FIG. 13. Top hits based on strongest phenotype and >2 oligo hit.

FIG. 33. List of trastuzumab resistance markers identified.

FIG. 34. Summary of expression data in basal-like cell lines and tumors.

FIG. 35. Accession numbers of markers identified herein.+

DETAILED DESCRIPTION OF THE PREFERRED EMBODIMENT

Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

A "HER receptor" or "HER" is a receptor protein tyrosine kinase which belongs to the HER receptor family and includes EGFR (ErbB1, HER1), HER2 (ErbB2), HER3 (ErbB3) and HER4 (ErbB4) receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated. The HER receptor may be a "native sequence" HER receptor or an "amino acid sequence variant" thereof. Preferably the HER receptor is native sequence human HER receptor. Thus, the term "HER", as used herein, will encompass HER1, HER2, HER3, and HER4.

The terms "ErbB1", "HER1", "epidermal growth factor receptor" and "EGFR" are used interchangeably herein and refer to EGFR as disclosed, for example, in Carpenter et al. *Ann. Rev. Biochem.* 56:881-914 (1987), including naturally occurring mutant forms thereof (e.g. a deletion mutant EGFR as in Ullrich et al, Nature (1984) 309:418425 and Humphrey et al. *PNAS* (USA) 87:4207-4211 (1990)), as well we variants thereof, such as EGFRvIII. Variants of EGFR also include deletional, substitutional and insertional variants, for example those described in Lynch et al (New England Journal of Medicine 2004, 350:2129), Paez et al (Science 2004, 304:1497), and Pao et al (PNAS 2004, 101:13306).

The expressions "ErbB2" and "HER2" are used interchangeably herein and refer to human HER2 protein described, for example, in Semba et al., *PNAS* (USA) 82:6497-6501 (1985) and Yamamoto et al. *Nature* 319:230-234 (1986) (GenBank accession number X03363). The term "erbB2" refers to the gene encoding human HER2 and "neu" refers to the gene encoding rat $p185^{neu}$. Preferred HER2 is native sequence human HER2.

Figure 1:
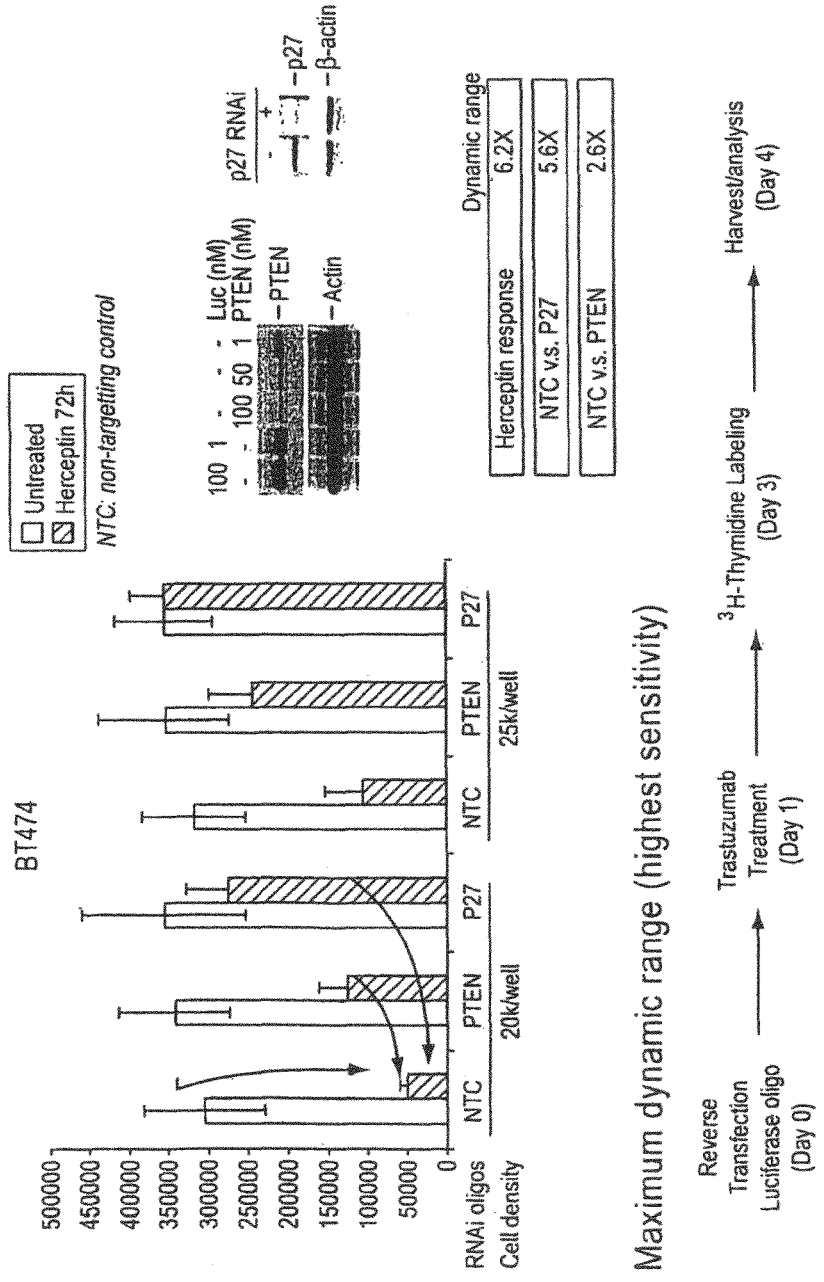
FIG. 1. Measurement of trastuzumab response of HER2 amplified cell line BT474 by 3H-thymidine incorporation assay.

Herein, "HER2 extracellular domain" or "HER2 ECD" refers to a domain of HER2 that is outside of a cell, either anchored to a cell membrane, or in circulation, including fragments thereof. In one embodiment, the extracellular domain of HER2 may comprise four domains: "Domain I" (amino acid residues from about 1-195, "Domain II" (amino acid residues from about 196-319), "Domain III" (amino acid residues from about 320-488), and "Domain IV" (amino acid residues from about 489-630) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004); and Plowman et al. *Proc. Natl. Acad. Sci.* 90:1746-1750 (1993), as well as FIG. 1 herein.

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989).

The terms "ErbB4" and "HER4" herein refer to the receptor polypeptide as disclosed, for example, in EP Pat. Appln. No. 599,274; Plowman et al., *Proc. Natl. Acad. Sci. USA,* 90:1746-1750 (1993); and Plowman et al., *Nature,* 366:473-475 (1993), including isoforms thereof, e.g., as disclosed in WO99/19488, published Apr. 22, 1999.

By "HER ligand" is meant a polypeptide which binds to and/or activates a HER receptor. The HER ligand of particular interest herein is a native sequence human HER ligand such as epidermal growth factor (EGF) (Savage et al., *J. Biol. Chem.* 247:7612-7621 (1972)); transforming growth factor alpha (TGF-α) (Marquardt et al., *Science* 223:1079-1082 (1984)); amphiregulin also known as schwanoma or keratinocyte autocrine growth factor (Shoyab et al. *Science* 243:1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Haran et al. *Oncogene* 18:2681-89 (1999)); and cripto (CR-1) (Kalman et al. *J. Biol. Chem.* 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4, and heregulins.

"Heregulin" (HRG) when used herein refers to a polypeptide encoded by the heregulin gene product as disclosed in U.S. Pat. No. 5,641,869, or Marchionni et al., *Nature,* 362:312-318 (1993). Examples of heregulins include heregulin-α, heregulin-β1, heregulin-β2 and heregulin-β3 (Holmes et al., *Science,* 256:1205-1210 (1992); and U.S. Pat. No. 5,641,869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); γ-heregulin (Schaefer et al. *Oncogene* 15:1385-1394 (1997)).

A "HER dimer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.,* 269(20): 14661-14665 (1994), for example. Other proteins, such as a cytokine receptor subunit (e.g. gp130) may be associated with the dimer. Preferably, the HER dimer comprises HER2.

A "HER heterodimer" herein is a noncovalently associated heterodimer comprising at least two different HER receptors, such as EGFR-HER2, HER2-HER3 or HER2-HER4 heterodimers.

A "HER inhibitor" is an agent which interferes with HER activation or function. Examples of HER inhibitors include HER antibodies (e.g. EGFR, HER2, HER3, or HER4 antibodies); EGFR-targeted drugs; small molecule HER antagonists; HER tyrosine kinase inhibitors; HER2 and EGFR dual tyrosine kinase inhibitors such as lapatinib/GW572016; antisense'molecules (see, for example, WO2004/87207); and/or agents that bind to, or interfere with function of, downstream signaling molecules, such as MAPK or Akt. Preferably, the HER inhibitor is an antibody or small molecule which binds to a HER receptor. The term "HER inhibitor" specifically includes HER1, HER2, HER3 and HER4 inhibitors. Thus, for example, a HER2 inhibitor is an agent which interferes with HER2 activation or function, including antibodies, small molecule HER2 antagonists, HER2 tyrosine kinase inhibitors, HER2 and EGFR dual tyrosine kinase inhibitors, antisense molecules, and the like.

A "HER dimerization inhibitor" or "HDI" is an agent which inhibits formation of a HER homodimer or HER heterodimer. Preferably, the HER dimerization inhibitor is an antibody, for example an antibody which binds to HER2 at the heterodimeric binding site thereof. However, HER dimerization inhibitors also include peptide and non-peptide small molecules, and other chemical entities which inhibit the formation of HER homo- or heterodimers. The most preferred HER dimerization inhibitor herein is pertuzumab or MAb 2C4. Binding of 2C4 to the heterodimeric binding site of HER2 is illustrated in FIG. 4. Other examples of HER dimerization inhibitors include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384 (2004)); antibodies which bind to HER3 and inhibit dimerization thereof with one or more other HER receptors; antibodies which bind to HER4 and inhibit dimerization thereof with one or more other HER receptors; peptide dimerization inhibitors (U.S. Pat. No. 6,417,168); antisense dimerization inhibitors; etc.

A "HER2 dimerization inhibitor" herein is a HER2 antibody or other HER2 antagonist, such as a peptide or on-peptide small molecule, which bind to HER2 and interferes with the formation of HER2-containing oligomers, including HER2 homo- and heterodimers, such as one or more of HER2-HER2, HER2-EGFR, HER2-HER3, and HER2-HER4 heterodimers. Preferably, the HER2 dimerization inhibitor is a molecule, such as an HER2 antibody or a peptide or non-peptide small molecule, that blocks the formation of all of HER2-HER2, HER2-EGFR and HER2-HER3 heterodimers, for example by binding to HER2 at a location required for heterodimerization, such as the heterodimeric binding site shown in FIG. 4. A typical representative of such HER2 dimerization inhibitors is pertuzumab, which was also listed as a "HER dimerization inhibitor" in a broader sense.

A "HER antibody" or "HER antibody" is an antibody that binds to a HER receptor. Optionally, the HER antibody further interferes with HER activation or function. Preferably, the HER antibody binds to the HER2 receptor. A HER2 antibody of particular interest herein is trastuzumab. Another example of a HER2 antibody is pertuzumab.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

"Phosphorylation" refers to the addition of one or more phosphate group(s) to a protein, such as a HER receptor, or substrate thereof.

An antibody which "inhibits HER dimerization" is an antibody which inhibits, or interferes with, formation of a HER dimer, regardless of the underlying mechanism. Preferably, such an antibody binds to HER2 at the heterodimeric binding site thereof. The most preferred dimerization inhibiting antibody herein is pertuzumab or MAb 2C4. Binding of 2C4 to the heterodimeric binding site of HER2 is illustrated in FIG. 4. Other examples of antibodies which inhibit HER dimerization include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384 (2004)); antibodies which bind to HER3 and inhibit dimerization thereof with one or more other HER receptors; and antibodies which bind to HER4 and inhibit dimerization thereof with one or more other HER receptors.

An antibody which "blocks ligand activation of a HER receptor more effectively than trastuzumab" is one which reduces or eliminates HER ligand activation of HER receptor(s) or HER dimer(s) more effectively (for example at least about 2-fold more effectively) than trastuzumab. Preferably, such an antibody blocks HER ligand activation of a HER receptor at least about as effectively as murine monoclonal antibody 4D5 or a Fab fragment thereof, or as trastuzumab or a Fab fragment thereof. One can evaluate the ability of an antibody to block ligand activation of a HER receptor by studying HER dimers directly, or by evaluating HER activation, or downstream signaling, which results from HER dimerization, and/or by evaluating the antibody-HER2 binding site, etc. Assays for screening for antibodies with the ability to inhibit ligand activation of a HER receptor more effectively than trastuzumab are described in Agus et al. *Cancer Cell* 2: 127-137 (2002) and U.S. Pat. No. 6,949,245 (Adams et al.). By way of example only, one may assay for: inhibition of HER dimer formation (see, e.g., FIGS. 1A-B of Agus et al. *Cancer Cell* 2: 127-137 (2002); and U.S. Pat. No. 6,949,245); reduction in HER ligand activation of cells which express HER dimers (U.S. Pat. No. 6,949,245 and FIGS. 2A-B of Agus et al. *Cancer Cell* 2: 127-137 (2002), for example); blocking of HER ligand binding to cells which express HER dimers (U.S. Pat. No. 6,949,245, and FIG. 2E of Agus et al. *Cancer Cell* 2: 127-137 (2002), for example); cell growth inhibition of cancer cells (e.g. MCF7, MDA-MD-134, ZR-75-1, MD-MB-175, T-47D cells) which express HER dimers in the presence (or absence) of HER ligand (U.S. Pat. No. 6,949,245,and FIGS. 3A-D of Agus et al. *Cancer Cell* 2: 127-137 (2002), for instance); inhibition of downstream signaling (for instance, inhibition of HRG-dependent AKT phosphorylation or inhibition of HRG- or TGFα-dependent MAPK phosphorylation) (see, U.S. Pat. No. 6,949,245, and FIGS. 2C-D of Agus et al. *Cancer Cell* 2: 127-137 (2002), for example). One may also assess whether the antibody inhibits HER dimerization by studying the antibody-HER2 binding site, for instance, by evaluating a structure or model, such as a crystal structure, of the antibody bound to HER2 (See, for example, Franklin et al. *Cancer Cell* 5:317-328 (2004)).

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2. Franklin et al. *Cancer Cell* 5:317-328 (2004).

The HER2 antibody may "inhibit HRG-dependent AKT phosphorylation" and/or inhibit "HRG- or TGFα-dependent MAPK phosphorylation" more effectively (for instance at least 2-fold more effectively) than trastuzumab (see Agus et al. *Cancer Cell* 2: 127-137 (2002) and WO01/00245, by way of example).

The HER2 antibody may be one which, like pertuzumab, does "not inhibit HER2 ectodomain cleavage" (Molina et al. *Cancer Res.* 61:4744-4749(2001)). Trastuzumab, on the other hand, can inhibit HER2 ectodomain cleavage. Thus, the HER2 antibody may be one which, like trastuzumab, inhibits HER2 ectodomain cleavage.

A HER2 antibody that "binds to a heterodimeric binding site" of HER2, binds to residues in domain II (and optionally also binds to residues in other of the domains of the HER2 extracellular domain, such as domains I and III), and can sterically hinder, at least to some extent, formation of a HER2-EGFR, HER2-HER3, or HER2-HER4 heterodimer. Franklin et al. *Cancer Cell* 5:317-328 (2004) characterize the HER2-pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II and optionally residues in other domain(s) of HER2, such as domains I and III. Preferably the antibody that binds to domain II binds to the junction between domains I, II and III of HER2.

Herein "time to disease progression" or "TTP" refer to the time, generally measured in weeks or months, from the time of initial treatment until the cancer progresses or worsens. Such progression can be evaluated by the skilled clinician.

By "extending TTP" is meant increasing the time to disease progression in a treated patient relative to an untreated patient.

"Survival" refers to the patient remaining alive, and includes overall survival as well as progression free survival.

"Overall survival" refers to the patient remaining alive for a defined period of time, such as 1 year, 5 years, etc. from the time of diagnosis or treatment.

"Progression free survival" refers to the patient remaining alive, without disease progression.

By "extending survival" is meant increasing overall or progression free survival in a treated patient relative to an untreated patient, or relative to a patient treated with an approved anti-tumor agent for the treatment of the cancer in question.

An "objective response" refers to a measurable response, including complete response (CR) or partial response (PR).

By "complete response" or "CR" is intended the disappearance of all signs of cancer in response to treatment. This does not always mean the cancer has been cured.

"Partial response" or "PR" refers to a decrease in the size of one or more tumors or lesions, or in the extent of cancer in the body, in response to treatment.

The term "refractory tumor" or "refractory cancer" is used to refer to tumors that fail to respond to or are resistant to a certain treatment, such as treatment with a HER2 inhibitor, such as a HER2 antibody, e.g. trastuzumab, when administered alone or in combination with other cancer treatments. For the purposes of this specification, refractory tumors also encompass tumors that appear to be inhibited by such treatment(s) but recur within 12 months from the completion of such treatment.

A tumor which "responds poorly" to a certain treatment, such as treatment with a HER2 inhibitor, such as a HER2 antibody, e.g. trastuzumab, does not show statistically significant improvement in response to such treatment when compared to no treatment or treatment with placebo in a recognized animal model or a human clinical trial, or which responds to initial treatment but grows as treatment is continued.

The term "standard of care" is used to refer to a treatment process that an ordinary skilled prudent physician uses to treat a certain disease, such as cancer. The standard of care varies depending on the type and stage of cancer, the patient's condition and treatment history, and the like, and will be apparent to those skilled in the art.

Protein "expression" refers to conversion of the information encoded in a gene into messenger RNA (mRNA) and then to the protein.

Herein, a sample or cell that "expresses" a protein of interest (such as a HER receptor or HER ligand) is one in which mRNA encoding the protein, or the protein, including fragments thereof, is determined to be present in the sample or cell.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced also increases in the proportion of the number of copies made of the particular gene expressed.

The term "modulate" is used herein to mean that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator.

The terms "inhibit", "down-regulate", and "reduce" are used interchangeably and mean that the expression of a gene, or level of RNA molecules or equivalent RNA molecules encoding one or more proteins or protein subunits, or activity of one or more proteins or protein subunits, is reduced relative to one or more controls, such as, for example, one or more positive and/or negative controls.

The term "up-regulate" is used to mean that the expression of a gene, or level of RNA molecules or equivalent RNA molecules encoding one or more proteins or protein subunits, or activity of one or more proteins or protein subunits, is elevated relative to one or more controls, such as, for example, one or more positive and/or negative controls.

An "interfering RNA" or "small interfering RNA (siRNA)" is a double stranded RNA molecule usually less than about 30 nucleotides in length that reduces expression of a target gene. Interfering RNAs may be identified and synthesized using known methods (Shi Y., *Trends in Genetics* 19(1):9-12 (2003), WO/2003056012 and WO2003064621), and siRNA libraries are commercially available, for example from Dharmacon, Lafayette, Colo.

A "native sequence" polypeptide is one which has the same amino acid sequence as a polypeptide (e.g., HER receptor or HER ligand) derived from nature, including naturally occurring or allelic variants. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "antibody" herein is used in the broadest sense and specifically covers monoclonal antibodies, polyclonal antibodies, multispecific antibodies (e.g. bispecific antibodies), and antibody fragments, so long as they exhibit the desired biological activity.

The term "monoclonal antibody" as used herein refers to an antibody from a population of substantially homogeneous antibodies, i.e., the individual antibodies comprising the population are identical and/or bind the same epitope(s), except for possible variants that may arise during production of the monoclonal antibody, such variants generally being present in minor amounts. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature*, 256:495 (1975); Harlow et al., *Antibodies: A Laboratory Manual*, (Cold Spring Harbor Laboratory Press, 2nd ed. 1988); Hammerling et al., in: Monoclonal Antibodies and T-Cell Hybridomas 563-681, (Elsevier, N.Y., 1981)), recombinant DNA methods (see, e.g., U.S. Pat. No. 4,816,567), phage display technologies (see, e.g., Clackson et al., *Nature*, 352:624-628 (1991); Marks et al., *J. Mol. Biol.*, 222:581-597 (1991); Sidhu et al., *J. Mol. Biol.* 338(2):299-310 (2004); Lee et al., *J. Mol. Biol.* 340(5):1073-1093 (2004); Fellouse, *Proc. Nat. Acad. Sci. USA* 101(34):12467-12472 (2004); and Lee et al. *J. Immuno. Methods* 284(1-2):119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); U.S. Pat. Nos. 5,545,806; 5,569,825; 5,591,669 (all of GenPharm); U.S. Pat. No. 5,545,807; WO 1997/17852; U.S. Pat. Nos. 5,545,807; 5,545,806; 5,569, 825; 5,625,126; 5,633,425; and 5,661,016; Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); and Lonberg and Huszar, *Intern. Rev. Immunol.*, 13: 65-93 (1995)).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc.) and human constant region sequences, as well as "humanized" antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or trastuzumab as described in Table 3 of U.S. Pat. No. 5,821,337 expressly incorporated herein by reference; humanized 520C9 (WO93/21319); and humanized 2C4 antibodies such as pertuzumab as described herein.

An "intact antibody" herein is one which comprises two antigen binding regions, and an Fc region. Preferably, the intact antibody has a functional Fc region.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragment(s).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab=fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., *Sequences of Proteins of Immunological Interest*, 5th Ed. Public Health Service, National Institutes of Health, Bethesda, Md. (1991), expressly incorporated herein by reference. The "EU index as in Kabat" refers to the residue numbering of the human IgG1 EU antibody.

A "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS (USA)* 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)), and regulates homeostasis of immunoglobulins.

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. No. 5,571,894; and U.S. Pat. No. 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$ - $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

A "naked antibody" is an antibody that is not conjugated to a heterologous molecule, such as a cytotoxic moiety or radiolabel.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

The term "main species antibody" herein refers to the antibody structure in a composition which is the quantitatively predominant antibody molecule in the composition. In one embodiment, the main species antibody is a HER2 antibody, such as an antibody that binds to Domain II of HER2, antibody that inhibits HER dimerization more effectively than trastuzumab, and/or an antibody which binds to a heterodimeric binding site of HER2. The preferred embodiment herein of the main species antibody is one comprising the variable light and variable heavy amino acid sequences in SEQ ID Nos. 3 and 4, and most preferably comprising the light chain and heavy chain amino acid sequences in SEQ ID Nos. 11 and 12 (pertuzumab).

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include an acidic variant (e.g. deamidated antibody variant), a basic variant, an antibody with an amino-terminal leader extension (e.g. VHS-) on one or two light chains thereof, an antibody with a C-terminal lysine residue on one or two heavy chains thereof, etc., and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moieities attached thereto which differ from one or more carbohydrate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc., and combinations of glycosylation alterations.

Where the antibody has an Fc region, an oligosaccharide structure may be attached to one or two heavy chains of the antibody, e.g. at residue 299 (298, Eu numbering of residues). For pertuzumab, G0 was the predominant oligosaccharide structure, with other oligosaccharide structures such as G0-F, G-1, Man5, Man6, G1-1, G1(1-6), G1(1-3) and G2 being found in lesser amounts in the pertuzumab composition.

Unless indicated otherwise, a "G1 oligosaccharide structure" herein includes G-1, G1-1, G1(1-6) and G1(1-3) structures.

An "amino-terminal leader extension" herein refers to one or more amino acid residues of the amino-terminal leader sequence that are present at the amino-terminus of any one or more heavy or light chains of an antibody. An exemplary amino-terminal leader extension comprises or consists of three amino acid residues, VHS, present on one or both light chains of an antibody variant.

A "deamidated" antibody is one in which one or more asparagine residues thereof has been derivatized, e.g. to an aspartic acid, a succinimide, or an iso-aspartic acid.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer.

An "advanced" cancer is one which has spread outside the site or organ of origin, either by local invasion or metastasis.

A "recurrent" cancer is one which has regrown, either at the initial site or at a distant site, after a response to initial therapy.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

Herein, a "subject"includes a mammalian and a human subject. The subject may be a "tumor subject" or a "cancer subject," i.e. one who is suffering or at risk for suffering from one or more symptoms of tumor, such as cancer.

A "tumor sample" herein is a sample derived from, or comprising tumor cells from, a patient's tumor. Examples of tumor samples herein include, but are not limited to, tumor biopsies, circulating tumor cells, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

A "fixed" tumor sample is one which has been histologically preserved using a fixative.

A "formalin-fixed" tumor sample is one which has been preserved using formaldehyde as the fixative.

An "embedded" tumor sample is one surrounded by a firm and generally hard medium such as paraffin, wax, celloidin, or a resin. Embedding makes possible the cutting of thin sections for microscopic examination or for generation of tissue microarrays (TMAs).

A "paraffin-embedded" tumor sample is one surrounded by a purified mixture of solid hydrocarbons derived from petroleum.

Herein, a "frozen" tumor sample refers to a tumor sample which is, or has been, frozen.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

A cancer or biological sample which "displays HER activation" is one which, in a diagnostic test, demonstrates activation or phosphorylation of a HER receptor. Such activation can be determined directly (e.g. by measuring HER phosphorylation by ELISA) or indirectly (e.g. by gene expression profiling or by detecting HER heterodimers, as described in U.S. patent application publication No. 2004/0106161, published Jun. 3, 2004).

Herein, "gene expression profiling" refers to an evaluation of expression of one or more genes as a surrogate for determining HER phosphorylation directly.

A "phospho-ELISA assay" herein is an assay in which phosphorylation of one or more HER receptors, especially HER2, is evaluated in an enzyme-linked immunosorbent assay (ELISA) using a reagent, usually an antibody, to detect phosphorylated HER receptor, substrate, or downstream signaling molecule. Preferably, an antibody which detects phosphorylated HER2 is used. The assay may be performed on cell lysates, preferably from fresh or frozen biological samples.

A cancer cell with "HER receptor overexpression or amplification" is one which has significantly higher levels of a HER receptor protein or gene compared to a noncancerous cell of the same tissue type. Such overexpression may be caused by gene amplification or by increased transcription or translation. HER receptor overexpression or amplification may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via fluorescent in situ hybridization (FISH; see WO98/45479 published October, 1998), southern blotting, or polymerase chain reaction (PCR) techniques, such as quantitative real time PCR (qRT-PCR). One may also study HER receptor overexpression or amplification by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Herein, an "anti-tumor agent" refers to a drug used to treat cancer. Non-limiting examples of anti-tumor agents herein include chemotherapeutic agents, HER dimerization inhibitors, HER antibodies, antibodies directed against tumor associated antigens, anti-hormonal compounds, cytokines, EGFR-targeted drugs, anti-angiogenic agents, tyrosine kinase inhibitors, growth inhibitory agents and antibodies, cytotoxic agents, antibodies that induce apoptosis, COX inhibitors, farnesyl transferase inhibitors, antibodies that binds oncofetal protein CA 125, HER2 vaccines, Raf or ras inhibitors, liposomal doxorubicin, topotecan, taxane, dual tyrosine kinase inhibitors, TLK286, EMD-7200, pertuzumab, trastuzumab, erlotinib, and bevacizumab.

An "approved anti-tumor agent" is a drug used to treat cancer which has been accorded marketing approval by a regulatory authority such as the Food and Drug Administration (FDA) or foreign equivalent thereof.

Where an anti-tumor agent is administered as a "single anti-tumor agent" it is the only anti-tumor agent administered to treat the cancer, i.e. it is not administered in combination with another anti-tumor agent, such as chemotherapy.

A "growth inhibitory agent" when used herein refers to a compound or composition which inhibits growth of a cell, especially a HER expressing cancer cell either in vitro or in vivo. Thus, the growth inhibitory agent may be one which significantly reduces the percentage of HER expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, S-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth inhibitory" antibodies are those which bind to HER2 and inhibit the growth of cancer cells overexpressing HER2. Preferred growth inhibitory HER2 antibodies inhibit growth of SK-BR-3 breast tumor cells in cell culture by greater than 20%, and preferably greater than 50% (e.g. from about 50% to about 100%) at an antibody concentration of about 0.5 to 30 µg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is a humanized variant of murine monoclonal antibody 4D5, e.g., trastuzumab.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the HER2 receptor. Preferably the cell is a tumor cell, e.g. a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using BT474 cells (see below). Examples of HER2 antibodies that induce apoptosis are 7C2 and 7F3.

The "epitope 4D5" is the region in the extracellular domain of HER2 to which the antibody 4D5 (ATCC CRL 10463) and trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive of the HER2 ECD, residue numbering including signal peptide).

The "epitope 2C4" is the region in the extracellular domain of HER2 to which the antibody 2C4 binds. In order to screen for antibodies which bind to the 2C4 epitope, a routine cross-blocking assay such as that described in *Antibodies, A Laboratory Manual*, Cold Spring Harbor Laboratory, Ed Harlow and David Lane (1988), can be performed. Preferably the antibody blocks 2C4's binding to HER2 by about 50% or more. Alternatively, epitope mapping can be performed to assess whether the antibody binds to the 2C4 epitope of HER2. Epitope 2C4 comprises residues from Domain II in the extracellular domain of HER2. 2C4 and pertuzumab binds to the extracellular domain of HER2 at the junction of domains I, II and III. Franklin et al. *Cancer Cell* 5:317-328 (2004).

The "epitope 7C2/7F3" is the region at the N terminus, within Domain I, of the extracellular domain of HER2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on HER2 (e.g. any one or more of residues in the region from about residue 22 to about residue 53 of the HER2 ECD, residue numbering including signal peptide).

"Treatment" refers to both therapeutic treatment and prophylactic or preventative measures. Those in need of treatment include those already with cancer as well as those in which cancer is to be prevented. Hence, the patient to be treated herein may have been diagnosed as having cancer or may be predisposed or susceptible to cancer.

The term "effective amount" refers to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma II and calicheamicin omega II (see, e.g., Agnew, *Chem Intl. Ed. Engl.*, 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; bisphosphonates such as clodronate (for example, BONEFOS® or OSTAC®), etidronate (DIDROCAL®), NE-58095, zoledronic acid/zoledronate (ZOMETA®), alendronate (FOSA-MAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); sorafenib (Bayer); SU-11248 (Pfizer); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

An "anti-hormonal agent" or "endocrine therapeutic" is an agent that acts to regulate, reduce, block, or inhibit the effects of hormones that can promote the growth of cancer. They may be hormones themselves. Examples include: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure antiestrogens without agonist properties, such as EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor downregulators (ERDs); anti-androgens such as flutamide, nilutamide and bicalutamide.

An "antimetabolite chemotherapeutic agent" is an agent which is structurally similar to a metabolite, but can not be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecitabine (XELODAJ), 6-mercaptopurine, methotrexate, 6-thioguanine, pemetrexed, raltitrexed, arabinosylcytosine ARA-C cytarabine (CYTOSAR-U®), dacarbazine (DTIC-DOME®), azocytosine, deoxycytosine, pyridmidene, fludarabine (FLUDARA®), cladribine, 2-deoxy-D-glucose etc. The preferred antimetabolite chemotherapeutic agent is gemcitabine.

"Gemcitabine" or "2'-deoxy-2',2'-difluorocytidine monohydrochloride (b-isomer)" is a nucleoside analogue that exhibits antitumor activity. The empirical formula for gemcitabine HCl is $C_9H_{11}F_2N_3O_4$ A HCl. Gemcitabine HCl is sold by Eli Lilly under the trademark GEMZAR®.

A "platinum-based chemotherapeutic agent" comprises an organic compound which contains platinum as an integral part of the molecule. Examples of platinum-based chemotherapeutic agents include carboplatin, cisplatin, and oxaliplatinum.

By "platinum-based chemotherapy" is intended therapy with one or more platinum-based chemotherapeutic agents, optionally in combination with one or more other chemotherapeutic agents.

By "chemotherapy-resistant" cancer is meant that the cancer patient has progressed while receiving a chemotherapy regimen (i.e. the patient is "chemotherapy refractory"), or the patient has progressed within 12 months (for instance, within 6 months) after completing a chemotherapy regimen.

By "platinum-resistant" cancer is meant that the cancer patient has progressed while receiving platinum-based chemotherapy (i.e. the patient is "platinum refractory"), or the patient has progressed within 12 months (for instance, within 6 months) after completing a platinum-based chemotherapy regimen.

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to vascular endothelial growth factor (VEGF), such as bevacizumab (AVASTIN®) (see U.S. Pat. No. 6,884,879B 1).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2 (e.g. PROLEUKIN®), IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943, 533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., *J. Biol. Chem.* 279 (29):30375-30384 (2004)). The anti-EGFR antibody may be conjugated with a cytotoxic agent, thus generating an immunoconjugate (see, e.g., EP659,439A2, Merck Patent GmbH). Examples of small molecules that bind to EGFR include ZD1839 or Gefitinib (IRESSA; Astra Zeneca); CP-358774 or Erlotinib (TARCEVA™; Genentech/OSI); and AG1478, AG1571 (SU 5271; Sugen); EMD-7200.

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the HER2 receptor tyrosine kinase (Pfizer and OSI); dual-HER inhibitors such as EKB-569 (available from Wyeth) which preferentially binds EGFR but inhibits both HER2 and EGFR-overexpressing cells; GW572016 (available from Glaxo) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (Gleevac®) available from Glaxo; MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; WO99/09016 (American Cyanimid); WO98/43960 (American Cyanamid); WO97/38983 (Warner Lambert); WO99/06378 (Warner Lambert); WO99/06396 (Warner Lambert); WO96/30347 (Pfizer, Inc.); WO96/33978 (Zeneca); WO96/3397 (Zeneca); and WO96/33980 (Zeneca).

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m² dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of the present invention, reference to "at least one," "at least two," "at least three," "at least four," "at least five," etc. of the genes listed in any particular gene set means any one or any and all combinations of the genes listed.

DETAILED DESCRIPTION

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", 2$^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4$^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

As discussed earlier, trastuzumab (Herceptin®) is an anti-human epidermal growth factor receptor 2 (HER2, ErbB2) therapeutic monoclonal antibody that provides significant clinical benefit for breast cancer patients whose tumors exhibit overexpression or amplification of the oncogene HER2 (Cobleigh, M. A. et al. Multinational study of the efficacy and safety of humanized anti-her2 monoclonal antibody in women who have her2-overexpressing metastatic breast cancer that has progressed after chemotherapy for metastatic disease (Cobleigh et al., *J Clin Oncol* 17, 2639-2648 (1999); Piccart-Gebhart, M. J. et al. *N Engl J Med* 353, 1659-1672 (2005); Romond, E. H. et al. *N Engl J Med* 353, 1673-1684 (2005); Slamon, D. J. et al. *N Eng! J Med* 344, 783-792 (2001); and Vogel, C. L. et al. *J Clin Oncol* 20, 719-726 (2002)).

Trastuzumab acts, at least in part, by blocking the interaction between overexpressed HER2 and its dimerization partner HER3, resulting in inhibition of oncogenic PI3K pathway signaling and subsequent upregulation of the cyclin dependent kinase (CDK) inhibitor p27 (Junttila, T. T. et al. Ligand-independent her2/her3/pi3k complex is disrupted by trastuzumab and is effectively inhibited by the pi3k inhibitor gdc-0941 (Lane, H. A. et al. *Mol Cell Bio!* 20, 3210-3223 (2000); Lane, H. A., Motoyama, A. B., Beuvink, I., & Hynes, N. E. *Ann Oncol* 12 Suppl 1, S21-22 (2001); Yakes, F. M. et al. *Cancer Res* 62, 4132-4141 (2002)). Unfortunately, due to the molecular heterogeneity of cancer, not all patients with HER2-amplified tumors respond to HER2-targeted agents. In the metastatic setting, those that derive initial benefit often exhibit evolution of the tumor with resultant progression on therapy. One major hypothesis on the mechanism of resistance to HER2-targeted therapy is that the PI3K pathway may be independently activated downstream of the HER2-HER3 receptor complex via loss of PTEN or acquisition of activating PIK3CA mutations (Berns, K. et al. *Cancer Cell* 12, 395-402 (2007); Nagata, Y. et al. *Cancer Cell* 6, 117-127 (2004)). A recent preclinical study demonstrates that trastuzumab-resistant models harboring PTEN loss or PIK3CA activating mutations are sensitive to GDC-0941, a class 1A PI3K small molecule inhibitor (Junttila, T. T. et al. *Cancer Cell* 15, 429-440 (2009)). This finding illustrates how understanding the molecular nature of resistance can reveal potentially more effective diagnostic/therapeutic co-development strategies to better treat individual patients.

While PTEN loss and PIK3CA activating mutations may play a role in trastuzumab resistance, we hypothesized that there could be additional resistance factors for several reasons. First, the PI3K signalling pathway is known to elicit a complex network of downstream events which may involve regulatory factors other than PTEN and PIK3CA (Bader, A. G., Kang, S., Zhao, L., & Vogt, P. K. *Nat Rev Cancer* 5, 921-929 (2005)). Second, there is ample evidence that the HER2/3 complex may activate signalling pathways other than PI3K, such as the MAPK pathway (Jones, R. B., Gordus, A., Krall, J. A., & MacBeath, G. *Nature* 439, 168-174 (2006)). Third, the downstream effect of trastuzumab primarily involves inhibition of the G1/S transition via stabilization of the cell cycle inhibitor p27, raising the possibility that downstream cell cycle regulators may also impact response to trastuzumab.

Identification of Diagnostic Markers of Resistance to Treatment with HER2 Inhibitors As discussed above, trastuzumab is used in clinical practice both in the adjuvant and the metastatic setting to treat breast cancer in patients whose tumor overexpresses the HER2 oncogene. Currently, HER2 expression levels are typically measured by two main types of assay, immunohistochemistry (IHC) and fluorescent in situ hybridization (FISH). Thus, HER2 overexpression may be analyzed by IHC, e.g. using the HERCEPTEST® (Dako). Paraffin embedded tissue sections from a tumor biopsy may be subjected to the IHC assay and accorded HER2 protein staining intensity criteria as follows:

Score 0–no staining is observed or membrane staining is observed in less than 10% of tumor cells.

Score 1+a faint/barely perceptible membrane staining is detected in more than 10% of the tumor cells. The cells are only stained in part of their membrane.

Score 2+a weak to moderate complete membrane staining is observed in more than 10% of the tumor cells.

Score 3+a moderate to strong complete membrane staining is observed in more than 10% of the tumor cells.

Those tumors with 0 or 1+ scores for HER2 overexpression assessment may be characterized as not overexpressing HER2, whereas those tumors with 2+ or 3+ scores may be characterized as overexpressing HER2.

Tumors overexpressing HER2 may be rated by immunohistochemical scores corresponding to the number of copies of HER2 molecules expressed per cell, and can been determined biochemically:

0=0-10,000 copies/cell,
1+=at least about 200,000 copies/cell,
2+=at least about 500,000 copies/cell,
3+=at least about 2,000,000 copies/cell.

Overexpression of HER2 at the 3+ level, which leads to ligand-independent activation of the tyrosine kinase (Hudziak et al., *Proc. Natl. Acad. Sci. USA,* 84:7159-7163 (1987)), occurs in approximately 30% of breast cancers, and in these patients, relapse-free survival and overall survival are diminished (Slamon et al., *Science,* 244:707-712 (1989); Slamon et al., *Science,* 235:177-182 (1987)).

Alternatively, or additionally, FISH assays such as the INFORM™ (sold by Ventana, Arizona) or PATHVISION™ (Vysis, Ill.) may be carried out on formalin-fixed, paraffin-embedded tumor tissue to determine the extent (if any) of HER2 amplification in the tumor.

For review, see Winston et al., *Am J. Pathol* 121(Suppl. 1):S33-49 (2004).

In patients with metastatic breast cancer, approximately 30% of patients who test positive for HER2 either by IHC or FISH (i.e. patients with HER2-expressing tumors) exhibit an objective response to trastuzumab alone, and about 50% to trastuzumab plus chemotherapy. Some of the remaining patients may still derive clinical benefit without an objective response, but there still remains a proportion of patients that exhibit primary resistance to trastuzumab. Furthermore, many patients that do benefit initially in the metastatic setting eventually progress while on trastuzumab treatment (acquired resistance). Patients with primary or acquired resistance to treatment with trastuzumab and collectively referred to as "refractory" or "resistant" to such treatment. In the adjuvant setting, the addition of trastuzumab to chemotherapy results in a significant improvement in disease-free survival. Nevertheless, there is still a group of patients whose tumor recurs after treatment.

The present invention is based on the identification of genes that are associated with trastuzumab resistance. Accordingly, the expression levels of such genes can serve as diagnostic markers to identify patients with HER2 expressing tumors who are less likely to respond to current therapies with trastuzumab or other HER2 inhibitors, and might benefit from novel combination treatments including trastuzumab or other HER2 inhibitors in combination with other anti-cancer agents and/or other treatment modalities.

It is well known that kinases and phosphatases control the reversible process of phosphorylation and are dysregulated in a variety of diseases, including cancer. Accordingly, a large-scale RNAi approach was elected to identify kinases and phosphatases that are associated with resistance to treatment with trastuzumab. In particular, performing a large-scale siRNA screen on HER2 positive cell lines that are sensitive to trastuzumab treatment in vitro, a group of kinases and phosphatases has been identified whose loss of function turned the cell lines resistant to treatment with trastuzumab. The results were validated by re-assaying the siRNA and by confirming the results in two different cell lines (BT474 and SKBR3). Details of this screen are provided in the Example below.

Thus, according to the present invention, the following genes have been identified as being associated with resistance to treatment with HER2 inhibitors: CDK11, DYRK1A, LATS2, STK10, Wee1, DUSP4, DUSP6, HIPK3, JNK, MAP4K4, PTPN11, Socs5, PPM1H, DKFZP586B16, DGKI, FLJ35107, FLT1, HK2, ITK, MOAP1, KIAA0685, KIAA1639, LIM/PDLIM5, PANK1, P14K2B, PPP2R1A, PRKWNK3, RYK, SPEC2, STK22C, STYK1, TXND3. These genes are also listed in Table 1, along with their NCBI GenBank accession numbers. Reduced expression or activity of one or more of these genes, or the corresponding RNA molecules or encoded proteins in a biological sample obtained from the patient, relative to control, indicates that the patient's tumor is likely to show resistance to treatment with a HER2 inhibitor.

The control can, for example, be a gene, present in the same cell, which is known to be down-regulated in patients showing resistance to HER2 inhibitor treatment (positive control), such as, for example, p27 or PTEN. Alternatively, or in addition, the control can be the expression level of the same gene in a normal cell of the same cell type (negative control). Expression levels can also be normalized, for example, to the expression levels of housekeeping genes, such as glyceraldehyde-3-phosphate-dehydrogenase (GAPDH) and/or β-actin, or to the expression levels of all genes in the sample tested. In one embodiment, expression of one or more of the above noted genes is deemed positive expression if it is at the median or above, e.g. compared to other samples of the same tumor-type. The median expression level can be determined essentially contemporaneously with measuring gene expression, or may have been determined previously. These and other methods are well known in the art, and are apparent to those skilled in the art.

Although the present invention identifies specific markers of tumor resistance to treatment with a HER2 inhibitor, surrogate markers the expression of which positively or negatively coordinately regulated with the expression of a gene specifically disclosed herein, are also suitable as resistance markers. Thus, surrogate markers include genes that are positive regulators of the same pathway as the pathway positively regulated by a gene specifically identified herein, or a downstream pathway. The lower expression (inactivation or inhibition) of such genes will be a predictor of resistance of HER2 expressing tumors to treatment with HER2 inhibitors. Included within this group are genes which show a similar expression pattern to a gene specifically disclosed herein, where the similar expression pattern may, for example, result from involvement of both genes in a particular biological process and/or being under common regulatory control in tumor cells. Surrogate markers also include genes the expression of which inversely correlates with the expression of a gene specifically identified herein, i.e. genes the expression of which is negatively coordinately regulated with a specifically disclosed gene. Included in this group of surrogate markers are genes which are negative regulators of the same pathway as a pathway positively regulated by a gene specifically identified herein, or a downstream pathway. The higher expression (activation or upregulation) of such genes will be a predictor of resistance of HER2 expressing tumors to treatment with HER2 inhibitors.

Diagnostic and Prognostic Methods

Methods for identifying patients for treatment with HER2 inhibitors, such as HER2 antibodies have been discussed above. Of this patient population, patients who are likely to be resistant or not repond well to such treatment can be identified by determining the expression level of one or more of the genes, the corresponding RNA molecules or encoded proteins in a biological sample comprising tumor cells obtained from the patient. The biological sample can, for example, be a fresh or frozen or archived paraffin-embedded and fixed (e.g. formalin-fixed) tissue sample, routinely prepared and preserved in everyday clinical practice. The biological sample can also be a different sample obtained from the patient, such as a biological fluid, including, without limitation, blood, urine, saliva, ascites fluid, or derivatives such as blood serum and blood plasma, and the like.

Various methods for determining expression of mRNA or protein include, but are not limited to, gene expression profiling, polymerase chain reaction (PCR) including quantitative real time PCR (qRT-PCR), microarray analysis that can be performed by commercially available equipment, following manufacturer's protocols, such as by using the Affymetrix GenChip technology, serial analysis of gene expression (SAGE) (Velculescu et al., *Science* 270:484-487 (1995); and Velculescu et al., *Cell* 88:243-51 (1997)), MassARRAY, Gene Expression Analysis by Massively Parallel Signature Sequencing (MPSS) (Brenner et al., *Nature Biotechnology* 18:630-634 (2000)), proteomics, immunohistochemistry (IHC), etc. Preferably mRNA is quantified. Such mRNA analysis is preferably performed using the technique of polymerase chain reaction (PCR), or by microarray analysis. Where PCR is employed, a preferred form of PCR is quantitative real time PCR (qRT-PCR).

The steps of a representative protocol for profiling gene expression using fixed, paraffin-embedded tissues as the RNA source, including mRNA isolation, purification, primer extension and amplification are given in various published journal articles (for example: Godfrey et al. *J. Molec. Diagnostics* 2: 84-91 (2000); Specht et al., *Am. J. Pathol.* 158: 419-29 (2001)). Briefly, a representative process starts with cutting about 10 microgram thick sections of paraffin-embedded tumor tissue samples. The mRNA is then extracted, and protein and DNA are removed. General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest*. 56:A67 (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MasterPure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation. After analysis of the RNA concentration, RNA repair and/or amplification steps may be included, if necessary, and RNA is reverse transcribed using gene specific promoters followed by PCR. Peferably, real time PCR is used, which is compatible both with quantitative competitive PCR, where internal competitor for each target sequence is used for normalization, and with quantitative comparative PCR using a normalization gene contained within the sample, or a housekeeping gene for RT-PCR. For further details see, e.g. "PCR: The Polymerase Chain Reaction", Mullis et al., eds., 1994; and Held et al., *Genome Research* 6:986-994 (1996). Finally, the data are analyzed to identify the best treatment option(s) available to the patient on the basis of the characteristic gene expression pattern identified in the tumor sample examined.

Expression levels can also be determined at the protein level, for example, using various types of immunoassays or proteomics techniques.

In immunoassays, the target diagnostic protein marker is detected by using an antibody specifically binding to the markes. The antibody typically will be labeled with a detectable moiety. Numerous labels are available which can be generally grouped into the following categories:

Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al. (1991) Ed. Wiley-Interscience, New York, N.Y., Pubs. for example and radioactivity can be measured using scintillation counting.

Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter.

Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al. (1981) Methods for the Preparation of Enzyme-Antibody Conjugates for use in Enzyme Immunoassay, in *Methods in Enzym*. (ed J. Langone & H. Van Vunakis), Academic press, New York 73:147-166.

Examples of enzyme-substrate combinations include, for example:

Horseradish peroxidase (HRPO) with hydrogen peroxidase as a substrate, wherein the hydrogen peroxidase oxidizes a dye precursor (e.g.,orthophenylene diamine (OPD) or 3,3',5,5'-tetramethyl benzidine hydrochloride (TMB));

alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In other versions of immunoassay techniques, the antibody need not be labeled, and the presence thereof can be detected using a labeled antibody which binds to the antibody.

Thus, the diagnostic immunoassays herein may be in any assay format, including, for example, competitive binding assays, direct and indirect sandwich assays, and immunoprecipitation assays. Zola, *Monoclonal Antibodies: A Manual of Techniques*, pp. 147-158 (CRC Press, Inc. 1987).

Competitive binding assays rely on the ability of a labeled standard to compete with the test sample analyze for binding with a limited amount of antibody. The amount of antigen in the test sample is inversely proportional to the amount of standard that becomes bound to the antibodies. To facilitate determining the amount of standard that becomes bound, the antibodies generally are insolubilized before or after the competition, so that the standard and analyze that are bound to the antibodies may conveniently be separated from the standard and analyze which remain unbound.

Sandwich assays involve the use of two antibodies, each capable of binding to a different immunogenic portion, or epitope, of the protein to be detected. In a sandwich assay, the test sample analyze is bound by a first antibody which is immobilized on a solid support, and thereafter a second antibody binds to the analyze, thus forming an insoluble three-part complex. See, e.g., U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Protein levels can also be detected using proteomics techniques. The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable alternatives or supplements to other methods of gene expression profiling, and can be used, alone or in combination with other methods, to detect the products of the tumor resistance markers of the present invention.

Preferred markers of the present invention, identified by the kinase library screen, include DYRK1A, HK2, Socs5, STK10, KIaa1639, and MAP4K4. A particularly preferred group of kinase markers includes DYRK1A, HK2, Socs5, and STK10. Members of these groups, as single markers or in any combination, are preferred for use in the diagnostic assays of the present invention.

Preferred markers, identified by the phosphatase library screen, include PTPN11, KIAA0685, and PPM1H. These markers, as single markers or any , combination, are preferred for use in the diagnostic assays of the present invention.

The most preferred marker herein is PPM1H.

Measurement of biomarker expression levels may be performed by using a software program executed by a suitable processor. Suitable software and processors are well known in the art and are commercially available. The program may be embodied in software stored on a tangible medium such as CD-ROM, a floppy disk, a hard drive, a DVD, or a memory associated with the processor, but persons of ordinary skill in the art will readily appreciate that the entire program or parts thereof could alternatively be executed by a device other than a processor, and/or embodied in firmware and/or dedicated hardware in a well known manner.

Following the measurement of the expression levels of the genes identified herein, or their expression products, and the determination that a subject is likely or not likely to respond to treatment with a HER2 inhibitor, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. In some embodiments, the assays will be performed or the assay results analyzed in a country or jurisdiction which differs from the country or jurisdiction to which the results or diagnoses are communicated.

In a preferred embodiment , a diagnosis, prediction and/or treatment recommendation based on the expression level in a test subject of one or more of the biomarkers herein is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, electronic forms of communication, such as email, or telephone. Communication may be facilitated by use of a computed, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

To facilitate diagnosis and/or prognosis, the reference and/or subject biomarker profiles or expression level of one or more of the biomarkers presented herein of the present invention can be displayed on a display device, contained electronically, or in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history.

Identification of HER2 Inhibitors

The first step in identifying inhibitors of a HER2 polypeptide, is typically in vitro screening to identify compounds that selectively bind HER2. The binding affinity of the candidate compounds can be tested by direct binding (see, e.g. Schoemaker et al., J. Pharmacol. Exp. Ther., 285:61-69 (1983)) or by indirect. e.g. competitive, binding. In competitive binding experiments, the concentration of a compound necessary to displace 50% of another compound bound to the target polypeptide (IC50) is usually used as a measure of binding affinity. If the test compound binds HER2 selectively and with high affinity, displacing another compound bound to HER2, such as a HER2 antibody, it is identified as HER2 inhibitor. Cell based assays can be used in a similar manner.

A preferred group of HER2 inhibitors includes antibodies specifically binding to HER2. Antibody "binding affinity" may be determined by equilibrium methods (e.g. enzyme-linked immunoabsorbent assay (ELISA) or radioimmuno-assay (RIA)), or kinetics (e.g. BIACORE™ analysis), for example. Also, the antibody may be subjected to other "biological activity assays", e.g., in order to evaluate its "potency" or pharmacological activity and potential efficacy as a therapeutic agent. Such assays are known in the art and depend on the target antigen and intended use for the antibody.

Other HER2 inhibitors include peptide and non-peptide small molecules, and antisense, ribozyme and triple helix molecules.

Non-antibody HER2 inhibitors, such as peptide and non-peptide small molecule inhibitors of HER2, can be identified by binding or interaction assays, well known in the art.

All binding assays for inhibitors are common in that they call for contacting the candidate inhibitor with a HER2 polypeptide under conditions and for a time sufficient to allow these two components to interact. In binding assays, the interaction is binding, and the complex formed can be isolated or detected in the reaction mixture. In a particular embodiment, either the HER2 or the candidate inhibitor is immobilized on a solid phase, e.g., on a microtiter plate, by covalent or non-covalent attachments. Non-covalent attachment generally is accomplished by coating the solid surface with a solution of the HER2 polypeptide and drying. Alternatively, an immobilized antibody, e.g., a monoclonal antibody, specific for the HER2 polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound is a polypeptide which interacts with but does not bind to HER2, the interaction of HER2 with the respective polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 (1989); Chien et al., *Proc. Natl. Acad. Sci. USA*, 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

It is emphasized that the screening assays specifically discussed herein are for illustration only. A variety of other assays, which can be selected depending on the type of the antagonist candidates screened (e.g. polypeptides, peptides, non-peptide small organic molecules, nucleic acid, etc.) are well know to those skilled in the art and are equally suitable for the purposes of the present invention.

The assays described herein may be used to screed libraries of compounds, including, without limitation, chemical libraries, natural product libraries (e.g. collections of microorganisms, animals, plants, etc.), and combinatorial libraries comprised of random peptides, oligonucleotides or small organic molecules. In a particular embodiment, the assays herein are used to screen antibody libraries, including, without limitation, naïve human, recombinant, synthetic and semi-synthetic antibody libraries. The antibody library can, for example, be a phage display library, including monovalent libraries, displaying on average one single-chain antibody or antibody fragment per phage particle, and multi-valent libraries, displaying, on average, two or more antibodies or antibody fragments per viral particle. However, the antibody libraries to be screened in accordance with the present invention are not limited to phage display libraries. Other display technique include, for example, ribosome or mRNA display (Mattheakis et al., *Proc. Natl. Acad. Sci. USA* 91:9022-9026 (1994); Hanes and Pluckthun, *Proc. Natl. Acad. Sci. USA* 94:4937-4942 (1997)), microbial cell display, such as bacterial display (Georgiou et al., *Nature Biotech.* 15:29-34 (1997)), or yeast cell display (Kieke et al., *Protein Eng.* 10:1303-1310 (1997)), display on mammalian cells, spore display, viral display, such as retroviral display (Urban et al., *Nucleic Acids Res.* 33:e35 (2005), display based on protein-DNA linkage (Odegrip et al., *Proc. Acad. Natl. Sci. USA* 101:2806-2810 (2004); Reiersen et al., *Nucleic Acids Res.* 33:e10 (2005)), and microbead display (Sepp et al., *FEBS Lett.* 532:455-458 (2002)). Libraries of other molecules, such as combinatorial libraries of synthetic small molecules can also be screened in a similar manner.

HER2 inhibitors can also be designed to reduce the level of endogenous HER2 gene expression, for example, by using well-known antisense or ribozyme approaches to inhibit or prevent translation of HER2 mRNA or triple helix approachet to inhibit transcription of HER2 genes. Such antisense, ribozyme, and triple helix antagonists may be designed to reduce or inhibit either unimpaired, or if appropriate, mutant HER2 gene activity. Techniques for the production and use of such molecules are well known to those of skill in the art.

Antisense RNA and DNA molecules can act to directly block the translation of mRNA by hybridizing to targeted endogenous mRNA thereby preventing translation. Alternatively, antisense RNA or DNA can inhibit or prevent transcription of the target gene. The antisense approach involves designing oligonucleotides (either DNA or RNA) that are complementary to a HER2 mRNA, or complementary to a portion of the target gene, such as a regulatory element that controls transcription of the gene. Typically, antisense nucleic acids should be at least six nucleotides in length, and are preferably oligonucleotides ranging from 6 to about 50 nucleotides in length.

Production of Antibodies

Since, in the preferred embodiment, the HER2 inhibitor is an antibody, a description follows as to exemplary techniques for the production of HER antibodies used in accordance with the present invention. The HER antigen to be used for production of antibodies may be, e.g., a soluble form of the extracellular domain of a HER receptor or a portion thereof, containing the desired epitope. Alternatively, cells expressing HER at their cell surface (e.g. NIH-3T3 cells transformed to overexpress HER2; or a carcinoma cell line such as SK-BR-3 cells, see Stancovski et al. *PNAS (USA)* 88:8691-8695 (1991)) can be used to generate antibodies. Other forms of HER receptor useful for generating antibodies will be apparent to those skilled in the art.

Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with 1/5 to 1/10 the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Various methods for making monoclonal antibodies herein are available in the art. For example, the monoclonal antibodies may be made using the hybridoma method first described by Kohler et al., *Nature*, 256:495 (1975), by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. *Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222: 581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

U.S. Pat. No. 6,949,245 describes production of exemplary humanized HER2 antibodies which bind HER2 and block ligand activation of a HER receptor. The humanized antibody of particular interest herein blocks EGF, TGF-α and/or HRG mediated activation of MAPK essentially as effectively as murine monoclonal antibody 2C4 (or a Fab fragment thereof) and/or binds HER2 essentially as effectively as murine monoclonal antibody 2C4 (or a Fab fragment thereof). The humanized antibody herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX, where X is preferably D or S (SEQ ID NO:7); DVNPNSGGSIYNQRFKG (SEQ ID NO:8); and/or NLGPSFYFDY (SEQ ID NO:9), optionally comprising amino acid modifications of those CDR residues, e.g. where the modifications essentially maintain or improve affinity of the antibody. For example, the antibody variant of interest may have from about one to about seven or about five amino acid substitutions in the above variable heavy CDR sequences. Such antibody variants may be prepared by affinity maturation, e.g., as described below. The most preferred humanized antibody comprises the variable heavy domain amino acid sequence in SEQ ID NO:4.

The humanized antibody may comprise variable light domain complementarity determining residues KASQD-VSIGVA (SEQ ID NO:10); SASYX$^1$X$^2$X$^3$, where X$^1$ is preferably R or L, X$^2$ is preferably Y or E, and X$^3$ is preferably T or S (SEQ ID NO:11); and/or QQYYIYPYT (SEQ ID NO:12), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below. The most preferred humanized antibody comprises the variable light domain amino acid sequence in SEQ ID NO:3.

The present application also contemplates affinity matured antibodies which bind HER2 and block ligand activation of a HER receptor. The parent antibody may be a human antibody or a humanized antibody, e.g., one comprising the variable light and/or variable heavy sequences of SEQ ID Nos. 3 and 4, respectively (i.e. comprising the VL and/or VH of pertuzumab). The affinity matured antibody preferably binds to HER2 receptor with an affinity superior to that of murine 2C4 or pertuzumab (e.g. from about two or about four fold, to about 100 fold or about 1000 fold improved affinity, e.g. as assessed using a HER2-extracellular domain (ECD) ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody. The preferred intact IgG1 antibody comprises the light chain sequence in SEQ ID NO:13 and the heavy chain sequence in SEQ ID NO:14.

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and U.S. Pat. Nos. 5,591,669, 5,589,369 and 5,545,807. Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human HER2 antibodies are described in U.S. Pat. No. 5,772,997 issued Jun. 30, 1998 and WO 97/00271 published Jan. 3, 1997.

Antibody Fragments

Various techniques have been developed for the production of antibody fragments comprising one or more antigen binding regions. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a Alinear antibody@, e.g., as described in U.S. Pat. No. 5,641,870 for example. Such linear antibody fragments may be monospecific or bispecific.

Bispecific Antibodies

Bispecific antibodies are antibodies that have binding specificities for at least two different epitopes. Exemplary bispecific antibodies may bind to two different epitopes of the HER2 protein. Other such antibodies may combine a HER2 binding site with binding site(s) for EGFR, HER3 and/or HER4. Alternatively, a HER2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the HER2-expressing cell. Bispecific antibodies may also be used to localize cytotoxic agents to cells which express HER2. These antibodies possess a HER2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

WO 96/16673 describes a bispecific HER2/FcγRIII antibody and U.S. Pat. No. 5,837,234 discloses a bispecific HER2/FcγRI antibody IDM1 (Osidem). A bispecific HER2/Fcα antibody is shown in WO98/02463. U.S. Pat. No. 5,821,337 teaches a bispecific HER2/CD3 antibody. MDX-210 is a bispecific HER2-FcγRIII Ab.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N— or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in the following table, or as further described below in reference to amino acid classes, may be introduced and the products screened.

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in *Biochemistry*, second ed., pp. 73-75, Worth Publishers, New York (1975)):

non-polar: Ala (A), Val (V), Leu (L), Ile (I), Pro (P), Phe (F), Trp (W), Met (M)

uncharged polar: Gly (G), Ser (S), Thr (T), Cys (C), Tyr (Y), Asn (N), Gln (Q)

acidic: Asp (D), Glu (E)

basic: Lys (K), Arg (R), His(H)

Alternatively, naturally occurring residues may be divided into groups based on common side-chain properties:

hydrophobic: Norleucine, Met, Ala, Val, Leu, Ile;

neutral hydrophilic: Cys, Ser, Thr, Asn, Gln;

acidic: Asp, Glu;

basic: His, Lys, Arg;

residues that influence chain orientation: Gly, Pro;

aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human HER2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat. Appl. No. US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an. Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence. of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region may have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues).

Engineered antibodies with three or more (preferably four) functional antigen binding sites are also contemplated (US Appln. No. US2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Screening for Antibodies with the Desired Properties

Techniques for generating antibodies have been described above. One may further select antibodies with certain biological characteristics, as desired.

To identify an antibody which blocks ligand activation of a HER receptor, the ability of the antibody to block HER ligand binding to cells expressing the HER receptor (e.g. in conjugation with another HER receptor with which the HER receptor of interest forms a HER hetero-oligomer) may be determined. For example, cells naturally expressing, or transfected to express, HER receptors of the HER hetero-oligomer may be incubated with the antibody and then exposed to labeled HER ligand. The ability of the antibody to block ligand binding to the HER receptor in the HER hetero-oligomer may then be evaluated.

For example, inhibition of HRG binding to MCF7 breast tumor cell lines by HER2 antibodies may be performed using monolayer MCF7 cultures on ice in a 24-well-plate format essentially as described in U.S. Pat. No. 6,949,245. HER2 monoclonal antibodies may be added to each well and incubated for 30 minutes. 125I-labeled rHRGβ1177-224 (25 pm) may then be added, and the incubation may be continued for 4 to 16 hours. Dose response curves may be prepared and an IC50 value may be calculated for the antibody of interest. In one embodiment, the antibody which blocks ligand activation of a HER receptor will have an IC50 for inhibiting HRG binding to MCF7 cells in this assay of about 50 nM or less, more preferably 10 nM or less. Where the antibody is an antibody fragment such as a Fab fragment, the IC50 for inhibiting HRG binding to MCF7 cells in this assay may, for example, be about 100 nM or less, more preferably 50 nM or less.

Alternatively, or additionally, the ability of an antibody to block HER ligand-stimulated tyrosine phosphorylation of a HER receptor present in a HER hetero-oligomer may be assessed. For example, cells endogenously expressing the HER receptors or transfected to expressed them may be incubated with the antibody and then assayed for HER ligand-dependent tyrosine phosphorylation activity using an anti-phosphotyrosine monoclonal (which is optionally conjugated with a detectable label). The kinase receptor activation assay described in U.S. Pat. No. 5,766,863 is also available for determining HER receptor activation and blocking of that activity by an antibody.

In one embodiment, one may screen for an antibody which inhibits HRG stimulation of p180 tyrosine phosphorylation in MCF7 cells essentially as described in U.S. Pat. No. 6,949,245. For example, the MCF7 cells may be plated in 24-well plates and monoclonal antibodies to HER2 may be added to each well and incubated for 30 minutes at room temperature; then rHRGβ1$_{177-244}$ may be added to each well to a final concentration of 0.2 nM, and the incubation may be continued for 8 minutes. Media may be aspirated from each well, and reactions may be stopped by the addition of 100 μl of SDS sample buffer (5% SDS, 25 mM DTT, and 25 mM Tris-HCl, pH 6.8). Each sample (25 μl) may be electrophoresed on a 4-12% gradient gel (Novex) and then electrophoretically transferred to polyvinylidene difluoride membrane. Antiphosphotyrosine (at 1 μg/ml) immunoblots may be developed, and the intensity of the predominant reactive band at M$_r$–180,000 may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an $IC_{50}$ for the antibody of interest may be calculated. In one embodiment, the antibody which blocks ligand activation of a HER receptor will have an $IC_{50}$ for inhibiting HRG stimulation of p180 tyrosine phosphorylation in this assay of about 50 nM or less, more preferably 10 nM or less. Where the antibody is an antibody fragment such as a Fab fragment, the $IC_{50}$ for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g., essentially as described in Schaefer et al. *Oncogene* 15:1385-1394 (1997). According to this assay, MDA-MB-175 cells may be treated with a HER2 monoclonal antibody (10 μg/mL) for 4 days and stained with crystal violet. Incubation with a HER2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the HER2 antibody of interest may block heregulin dependent association of HER2 with HER3 in both MCF7 and SK-BR-3 cells as determined in a co-immunoprecipitation experiment such as that described in U.S. Pat. No. 6,949,245 substantially more effectively than monoclonal antibody 4D5, and preferably substantially more effectively than monoclonal antibody 7F3.

To identify growth inhibitory HER2 antibodies, one may screen for antibodies which inhibit the growth of cancer cells which overexpress HER2. In one embodiment, the growth inhibitory antibody of choice is able to inhibit growth of SK-BR-3 cells in cell culture by about 20-100% and preferably by about 50-100% at an antibody concentration of about 0.5 to 30 μg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 μg/ml of the HER2 added per dish. After six days, the number of cells, compared to untreated cells are counted using an electronic COULTER™ cell counter. Those antibodies which inhibit growth of the SK-BR-3 cells by about 20-100% or about 50-100% may be selected as growth inhibitory antibodies. See U.S. Pat No. 5,677,171 for assays for screening for growth inhibitory antibodies, such as 4D5 and 3E8.

In order to select for antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 μg/ml of the monoclonal antibody. Following a three day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FTIC) (1 μg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies. In addition to the annexin binding assay, a DNA staining assay using BT474 cells is available. In order to perform this assay, BT474 cells which have been treated with the antibody of interest as described in the preceding two paragraphs are incubated with 9 μg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay. See WO98/17797 for assays for screening for antibodies which induce apoptosis, such as 7C2 and 7F3.

To screen for antibodies which bind to an epitope on HER2 bound by an antibody of interest, a routine cross-blocking assay such as that described in *Antibodies, A Laboratory Manual*, Cold Spring Harbor Laboratory, Ed Harlow and David Lane (1988), can be performed to assess whether the antibody cross-blocks binding of an antibody, such as 2C4 or pertuzumab, to HER2. Alternatively, or additionally, epitope mapping can be performed by methods known in the art and/or one can study the antibody-HER2 structure (Franklin et al. *Cancer Cell* 5:317-328 (2004)) to see what domain(s) of HER2 is/are bound by the antibody.

Methods of Cancer Treatment

The patients identified in accordance with the present invention as likely to be resistant to treatment with HER2 inhibitors, are likely to benefit from combination treatments.

Combination treatments may include chemotherapy on conjunction with use of a HER2 inhibitor, such as a HER2 antibody, e.g. trastuzumab or pertuzumab.

The purpose of chemotherapeutic treatment of cancer is to cure the patient or, at least, slow down disease progression, increase survival, reduce the likelihood of cancer recurrence, control symptoms and/or maintain or improve quality of life. Chemotherapy varies depending on the type of cancer, and, in case of solid tumors, can be performed before and/or after surgical removal of primary tumor. For some cancers, there are a few universally accepted standard therapies, while the treatment of others is not yet standardized.

Exemplary chemotherapeutic agents have been listed before, and generally can be classified according to their mechanism of action. Some chemotherapeutic agents directly damage DNA and RNA. By disrupting replication of the DNA such chemotherapeutics either completely halt replication, or result in the production of nonsense DNA or RNA. This category includes, for example, cisplatin (Platinol®), daunorubicin (Cerubidine®), doxorubicin (Adriamycin®), and etoposide (VePesid®). Another group of cancer chemotherapeutic agents interfere with the formation of nucleotides or deoxyribonucleotides, so that RNA synthesis and cell replication is blocked. Examples of drugs in this class include methotrexate (Abitrexate®), mercaptopurine (Purinethol®), fluorouracil (Adrucil®), and hydroxyurea (Hydrea®). A third class of chemotherapeutic agents effects the synthesis or breakdown of mitotic spindles, and, as a result, interrupt cell division. Examples of drugs in this class include vinblastine (Velban®), vincristine (Oncovin®) and taxenes, such as, pacitaxel (Taxol®), and tocetaxel (Taxotere®). Other classifications, for example, based on the chemical structure of the chemotherapeutic agents, are also possible.

For breast cancer, doxorubicin (Adriamycin®) is considered by most the most effective single chemotherapeutic agent. In addition, 5-FU has been in clinical use for several decades, and is the cornerstone of many combination therapies for breast cancer. Other chemotherapeutic agents commonly used for the treatment of breast cancer include, for example, anthracyclines, taxane derivatives, and various combinations therapies, such as CMF (cyclophosphamide-methotrexate-fluorouracil) chemotherapy. Most patients receive chemotherapy immediately following surgical removal of tumor. This approach is commonly referred to as adjuvant therapy. However, chemotherapy can be administered also before surgery, as so called neoadjuvant treatment. Although the use of neo-adjuvant chemotherapy originates from the treatment of advanced and inoperable breast cancer, it has gained acceptance in the treatment of other types of cancers as well. The efficacy of neoadjuvant chemotherapy has been tested in several clinical trials. In the multi-center National Surgical Adjuvant Breast and Bowel Project B-18 (NSAB B-18) trial (Fisher et al., J. Clin. Oncology 15:2002-2004 (1997); Fisher et al., J. Clin. Oncology 16:2672-2685 (1998)) neoadjuvant therapy was performed with a combination of adriamycin and cyclophosphamide ("AC regimen"). In another clinical trial, neoadjuvant therapy was administered using a combination of 5-fluorouracil (5-FU), epirubicin and cyclophosphamide ("FEC regimen") (van Der Hage et al., J. Clin. Oncol. 19:4224-4237 (2001)). Other clinical trials have also used taxane-containing neoadjuvant treatment regiments. See, e.g. Holmes et al., J. Natl. Cancer Inst. 83:1797-1805 (1991) and Moliterni et al., Seminars in Oncology, 24:S17-10-S-17-14 (1999). For further information about neoadjuvant chemotherapy for breast cancer see, Cleator et al., Endocrine-Related Cancer 9:183-195 (2002).

5-FU, CPT-11 (irinotecan), and oxaliplatin, administered alone or in combination, have proven effective in the treatment of advanced colorectal cancer (CRC) (see, e.g. Grothey et al. (2004) J. Clin. Oncol. 22:1209-15).

Non-small-cell lung cancer (NSCLC) has been shown to respond well to combination therapy with vinorelbine, cisplatin and optionally paclitaxel (see, e.g. Rodriguez et al. (2004) Am. J. Clin. Oncol. 27:299-303).

Chemotherapeutic regimens for the treatment of other types of cancer are also well know to those skilled in the art.

Further details of the invention will be described in the following non-limiting Example

EXAMPLE 1

Identifying Markers of Trastuzumab Resistance in HER2+ Breast Cancer

HER2 is overexpresed by gene amplification in about 20% of breast cancers. It is known that HER2 gene amplification leads to significantly higher level of HER2 receptor expression compared to normal cells: e.g., IHC3+=1×10$^6$ receptors/cell (normal cells=2×10$^4$). It is also known that HER2 amplification is associated with higher tumor grade, lymph node positivity and poor prognosis, and HER2 status in metastases is highly correlated with HER2 status in the primary tumor.

While trastuzumab has been highly successful in the treatment of HER2-positive tumors, such as HER2-positive breast cancer, certain tumors are non-responsive, or show or develop resistance to trastuzumab treatment.

Using a cell line that is known to be sensitive to trastuzumab in vitro (BT474), an siRNA screen was performed to identify genes that when knocked down (or inactivated) lead to induction of trastuzumab resistance in vitro. Validated hits from the screen are candidate diagnostic markers of trastuzumab resistance in vivo.

Figure 2:
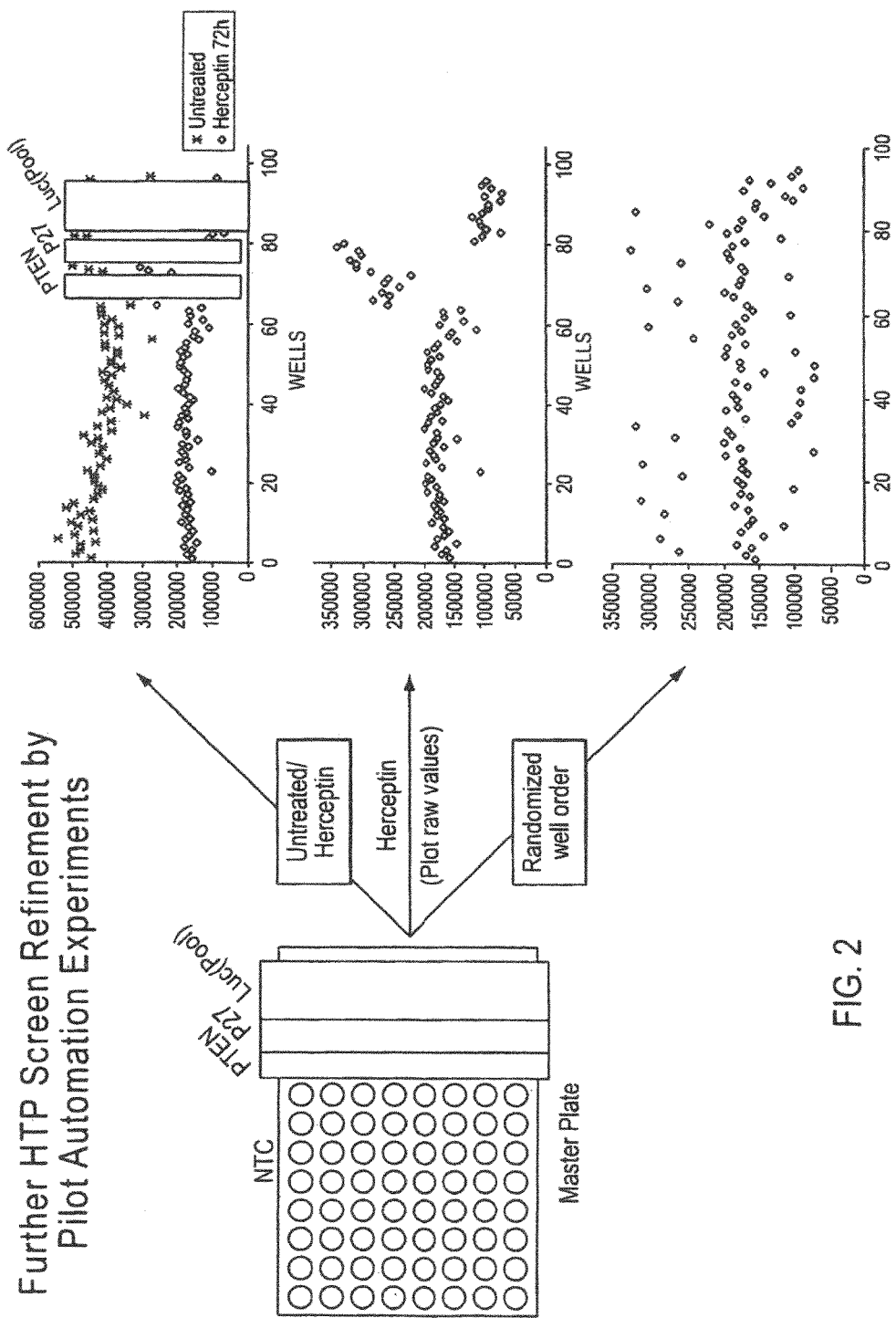
FIG. 2. Further HTP screen refinement by pilot automation experiments. NTC=non-targeting (negative) control.
Figures 4A, 4B:
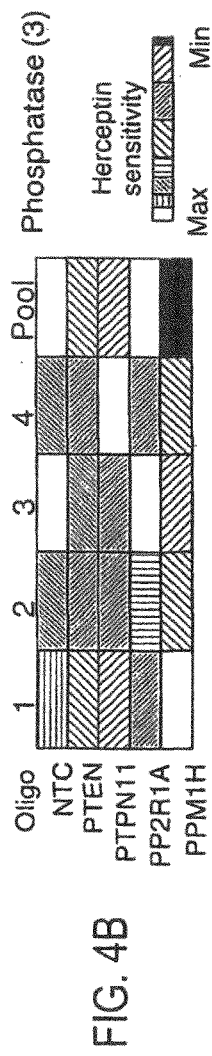
FIGS. 4A and 4B. Overview of the trastuzumab-resistance screen.

Methods:

Cell line and assay: The BT474 cell line was used, which is HER2-positive and sensitive to tastuzumab in vitro. Based on information in the literature, PTEN and p27 were used as positive controls to develop an assay for screening. Knockdown of both PTEN and p27 has been reported to reduce the ability of trastuzumab to slow cell proliferation in vitro. This effect has been observed in the present study as well and used these positive controls to optimize the assay. The most effective method of determining trastuzumab response in vitro was found to be measuring cell proliferation via a $^3$H-thymidine uptake assay. Briefly, the siRNA and lipofectamine were distributed onto 96-well plates. Cells were then plated onto the aliquoted siRNA and at 24 hours, trastuzumab was added at a concentration of 25 µg/ml. At 72 hours, $^3$H-thymidine was added to the cultures. The amount of incorporated $^3$H was measured using a 96-well plate cell harvested on day 4 (outline on FIG. 1).

siRNA screen: The screen was optimized for automated screening using a 96-well plate format using either luciferase or non-targeting controls as the negative control and PTEN and p27 as the positive control (FIGS. 2 and 3A,B). The finalized screen format is depicted in FIGS. 4A and 4B. Using this method, the Dharmacon kinase and phosphatase libraries, which covered 979 genes (779 genes from a kinase library and 200 gnes from a phosphoatase library), were screened and analyzed with 4 individually screened siRNA's against each gene.

Figure 5:
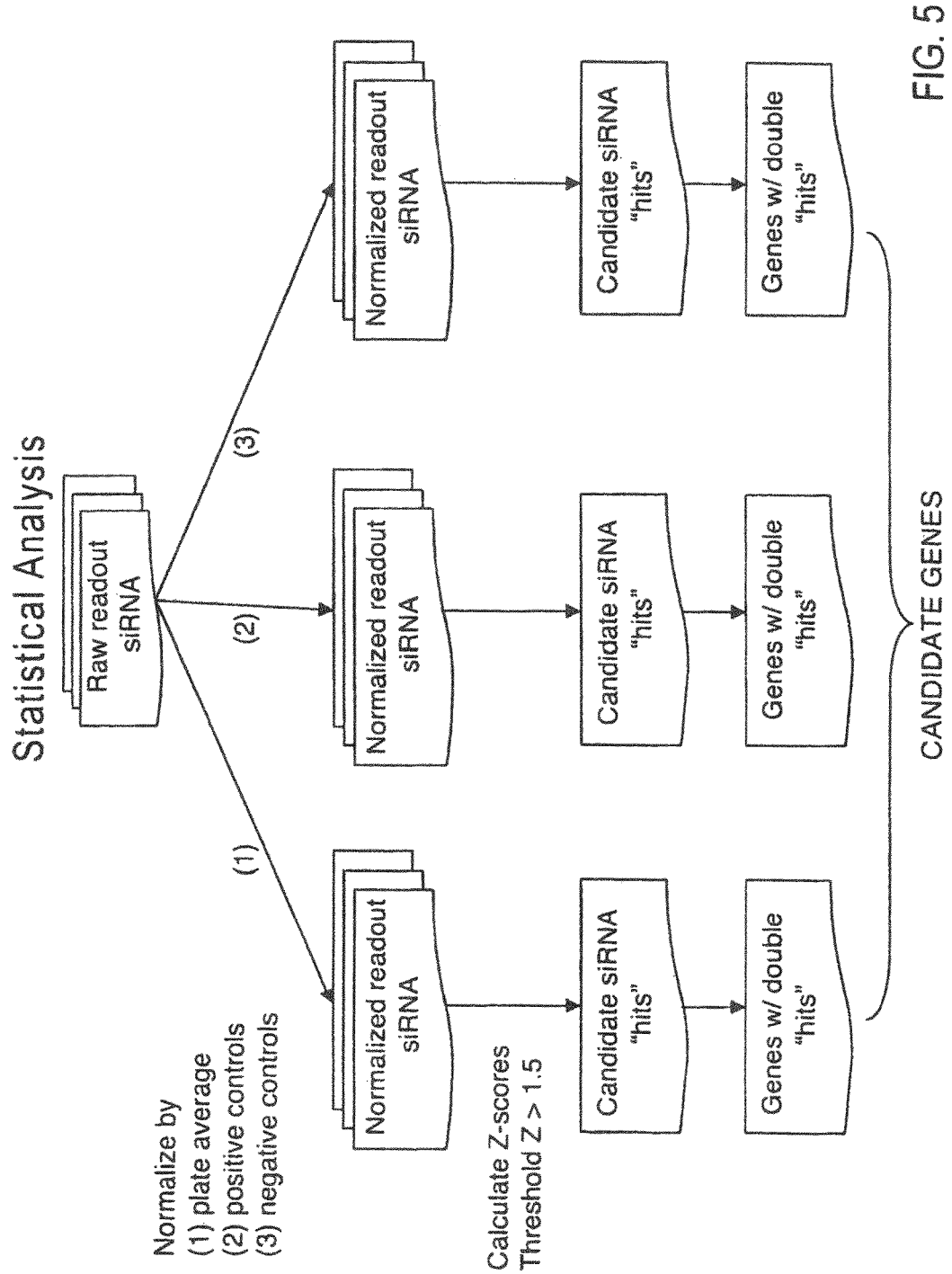
FIG. 5. Statistical analysis.
Figure 6A:
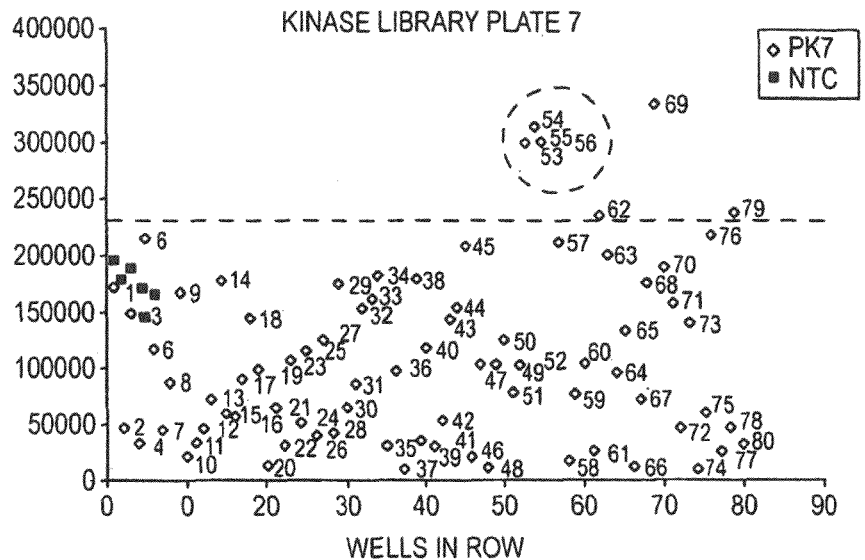
FIGS. 6A, 6B and 6C. Data analysis by plotting raw values of the screen showed p27 is a 4-oligo hit.
Figure 6B:
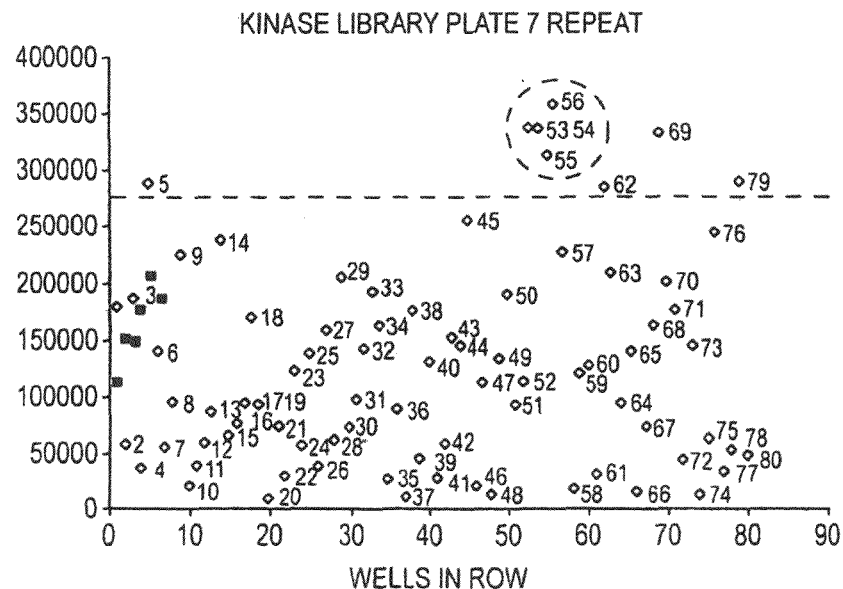
Figure 6C:
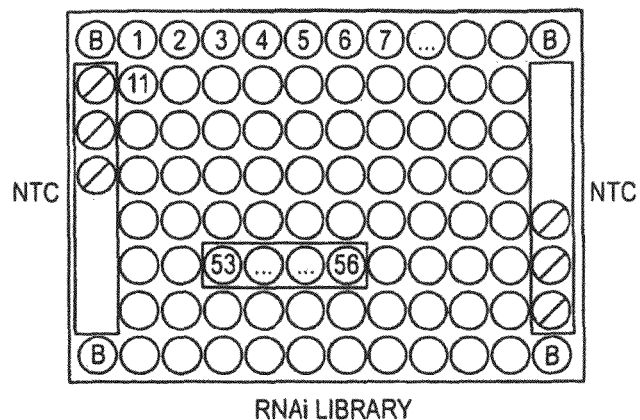

Data analysis: Data were analyzed in several ways. One method was to normalize data to various controls including the negative controls, the positive controls or to the plate average (FIG. 5). A gene was considered a hit if at least 2 of the 4 siRNA oligos were above a z-score threshold of 1.5. The data were also analyzed manually by plotting the data and identifying spots that were greater than 1.5 standard deviations above the mean for the non-targeting control, again with a minimum of 2 of the 4 siRNA oligos scoring positive to be considered a hit (FIGS. 6A-6C).

Figure 7:
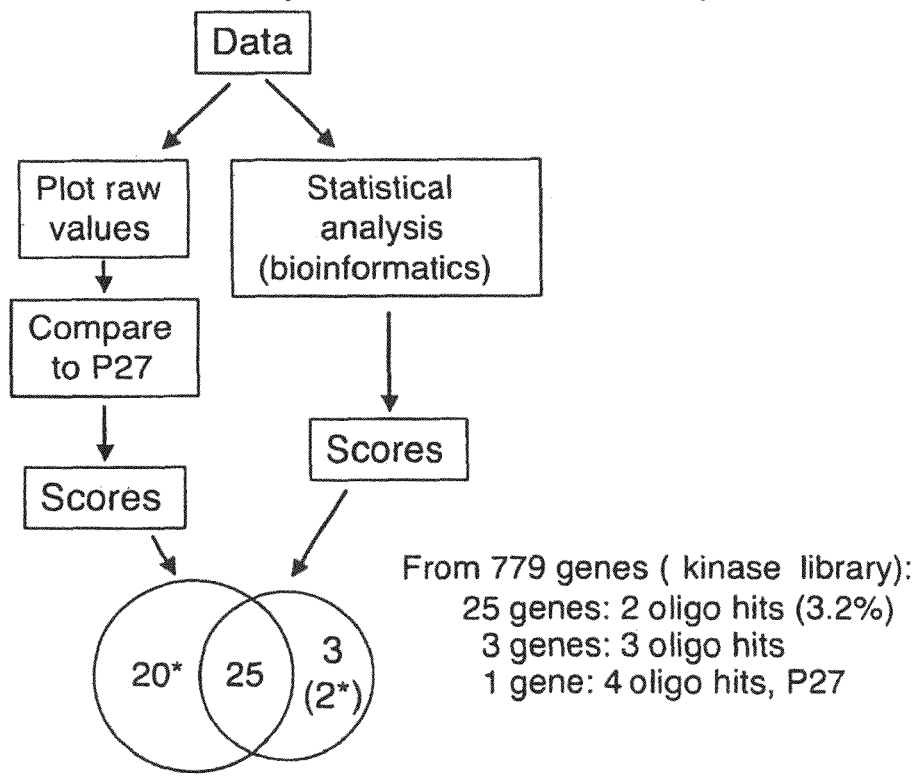
FIG. 7. Combined analysis of kinase library hits.
Figure 9A:
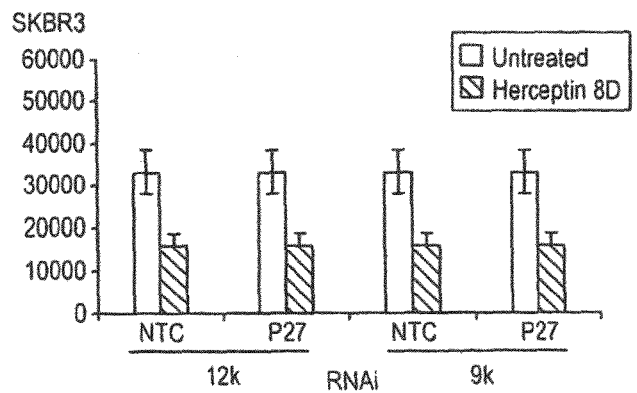
FIGS. 9A, 9B, 9C and 9D. Development of the secondary screen.
Figure 9B:
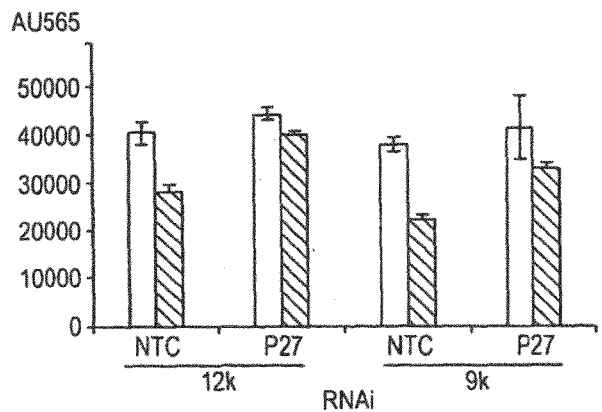
Figure 9C:
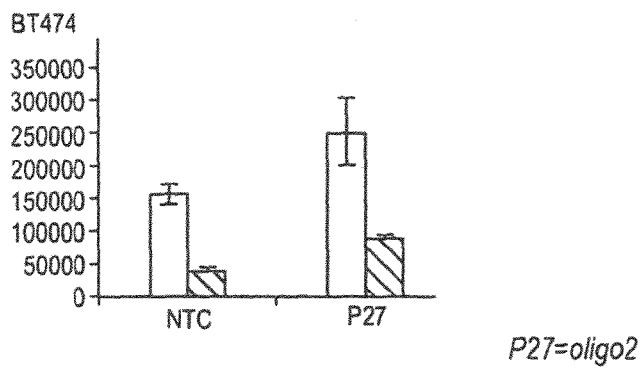
Figure 9D:
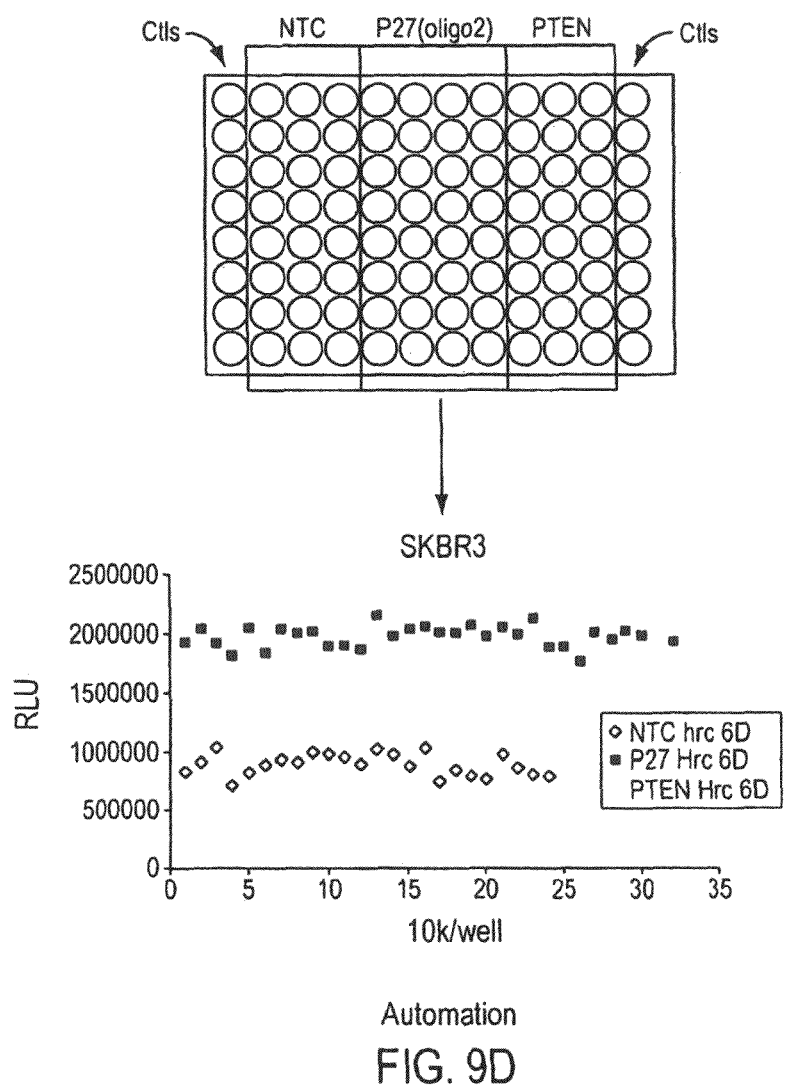
Figure 12A:
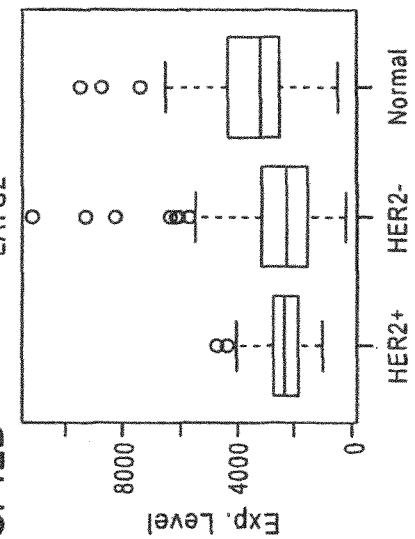
FIGS. 12A, 12B, 12C and 12D. GeneLogic expression data.
Figure 12B:
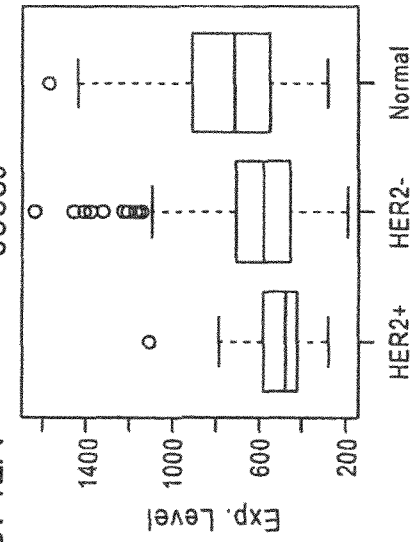
Figure 12C:
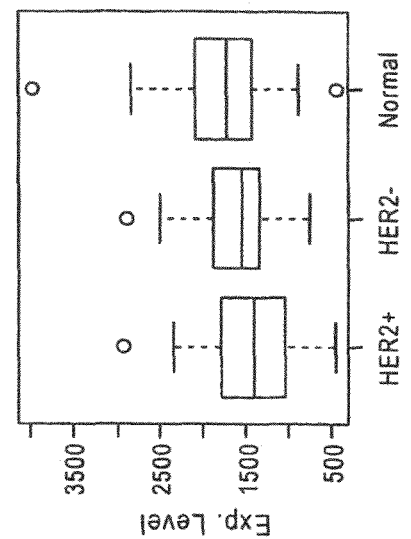
Figure 12D:
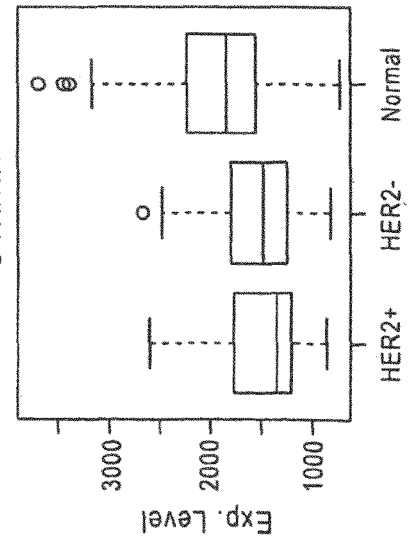

Results:

Primary screen data: From the analysis of the screen data, there were 25 genes that were identified as hits from the kinase library by all the data analysis methods that were used (FIG. 7). An additional 5 genes that were identified manually were found to be very close to the threshold in the biostatistics analysis and were included in further follow-up. Both of the positive controls, PTEN and p27, were on the plates initially screened (kinase library and one plate from phosphatase library) and were identified as hits, suggesting that the screen performed well to detect the type of hits of interest. The hits fell into several categories of potential interest including cell cycle regulators, major players in downstream receptor tyrosine kinase signaling, and several other categories (FIG. 8).

Hit validation: For further validation, we focused on 28 genes from this initial screen. This includes the 30 noted above minus the two positive controls PTEN and p27 which have already been validated in other studies. Two methods were used for validation. First, the siRNA's were re-screened in BT474 cells to determine whether the observation would repeat in the same system. The genes were then also screened in a different cell line (SKBR3) which is also HER2-positive and trastuzumab sensitive. Examples of how the positive controls PTEN and p27 performed in the validation screens is illustrated in FIGS. 9A-D. The 28 hits (other than PTEN and p27) from the primary screen are listed in FIG. 10 along with the results from the repeat screen and the screen in SKBR3 cells. Some of the most promising candidates considering the performance in validation screens are shaded.

In a smaller subsequent screen, the remaining phosphatase library plates were screened (other than the one plate containing PTEN which was screened with the kinase library). The results from the analysis of all phosphatase plates are shown in FIG. 11. PTEN was identified as a 3 oligo hit by two methods. There were an additional 3 genes that were at least 2 oligo hits by all normalization methods and are shaded in the list of hits on FIG. 11.

Another method of validation was to examine GeneLogic data to determine if any of the genes exhibited evidence of decreased expression in HER2-positive breast cancer compared to normal breast tissue or to HER2-negative breast cancer. Four genes did exhibit such a pattern—SOCS5, LATS2, PTPN11, and DYRK1A and are thus worth further follow-up even if the validation screen data is not as strong (e.g. LATS2) (FIGS. 12A-D).

The top hits based on the strongest phenotype and >2 oligo hits (PPM1H, DYRK1A, STK10, and PTPN11) are shown in FIG. 13.

Figure 14A:
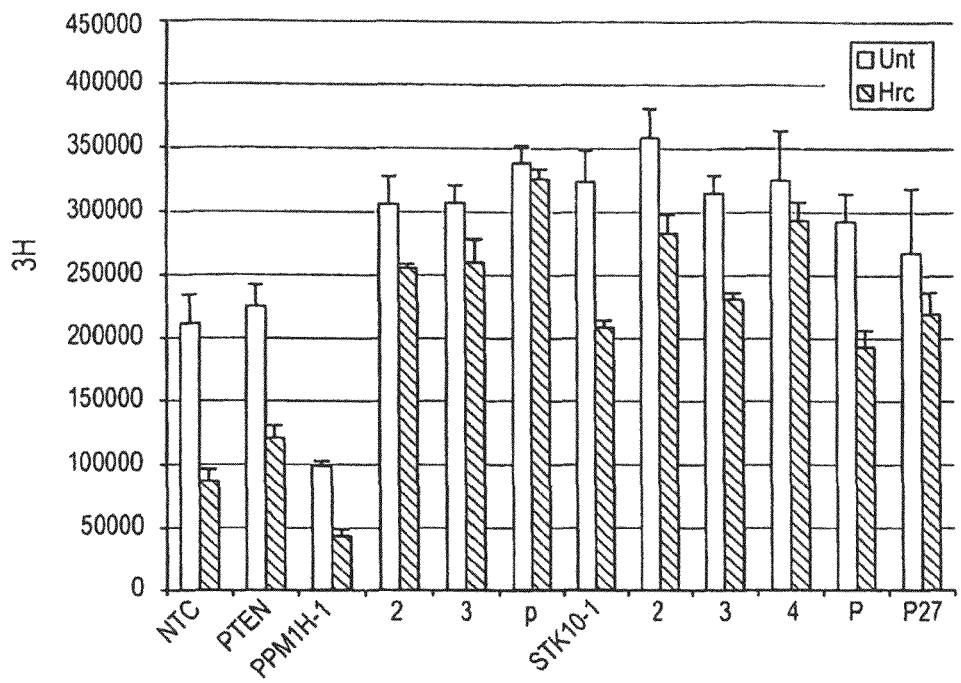
FIGS. 14A and 14B. 3H-Thymidine uptake assay after 72 hours of trastuzumab treatment in BT474 cell line, with and without the knockdown of candidate genes.
Figure 14B:
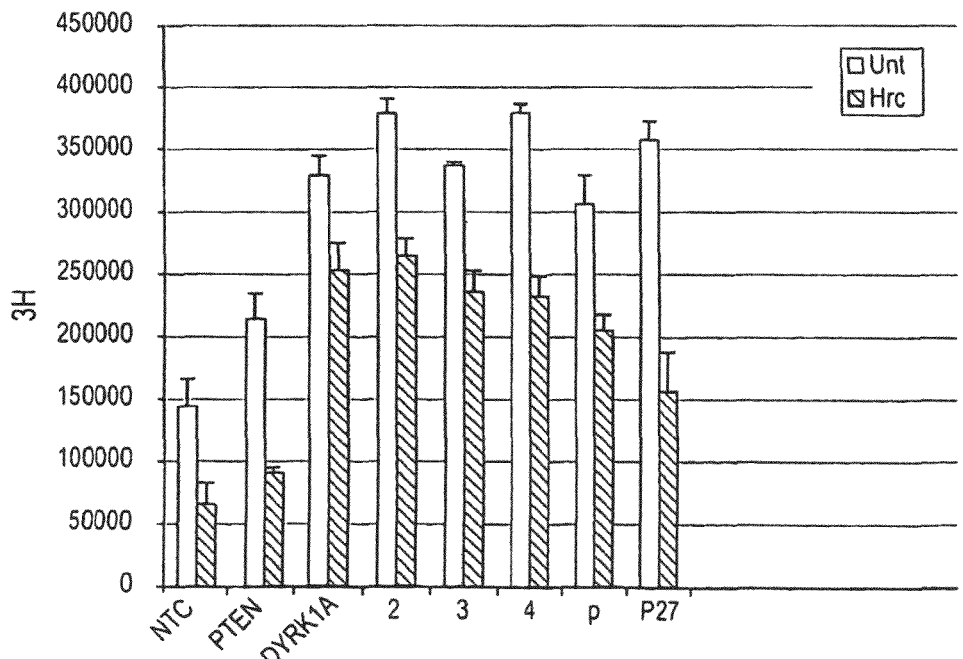
Figure 15A:
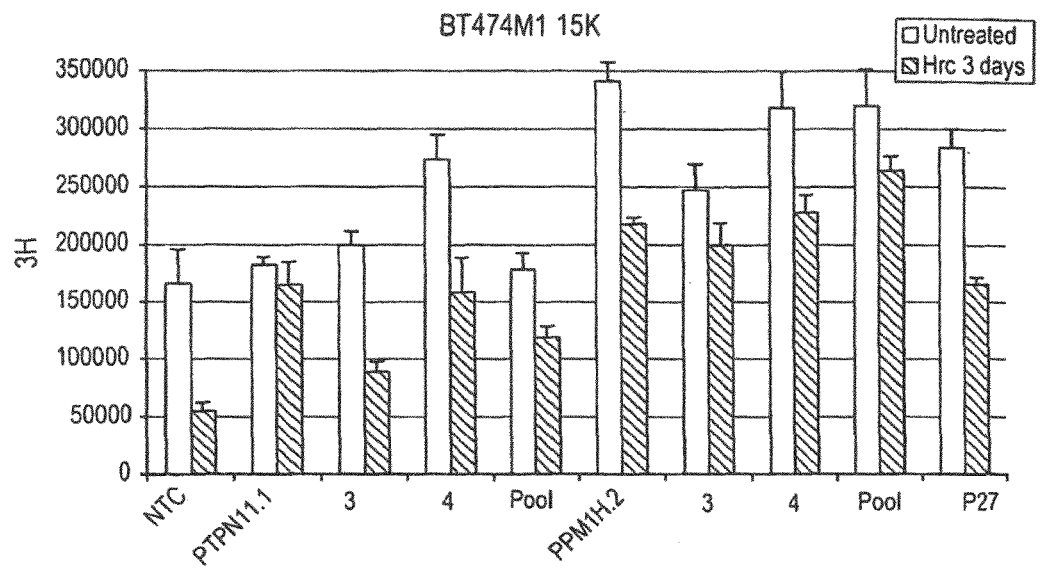
FIGS. 15A and 15B. 3H-Thymidine uptake assay after 72 hours of trastuzumab treatment in BT474M1 cell line.
Figure 15B:
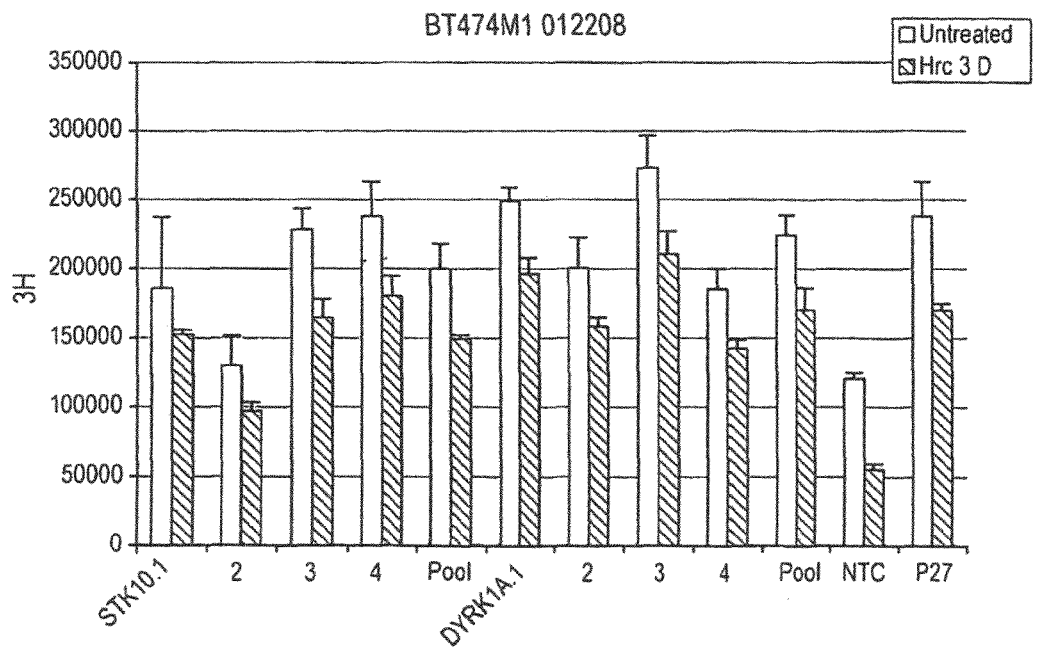

FIGS. 14A and B and 15A and B show examples of the top hits augment cell proliferation in BT474 cells and BT474-M1 cells treated with trastuzumab.

Figure 16A:
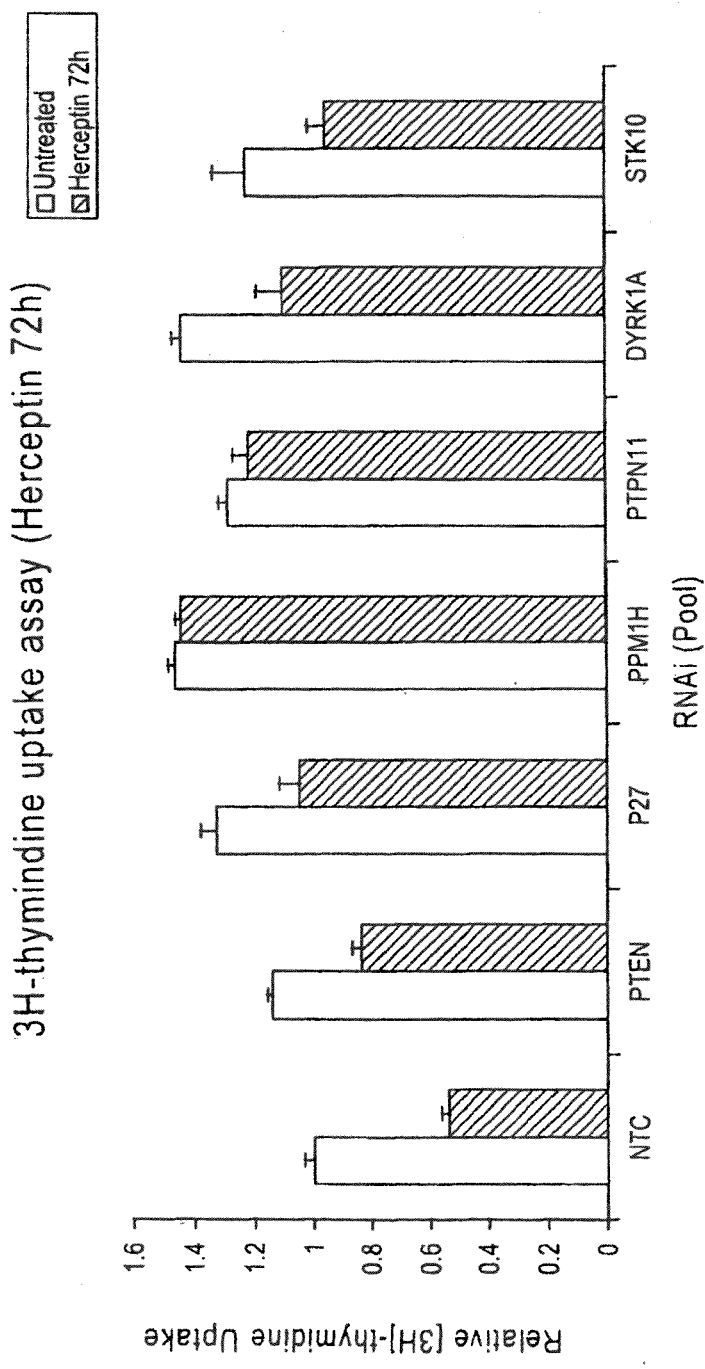
FIGS. 16A and 16B. 3H-Thymidine uptake assay of BT474M cell line after 72 hours of trastuzumab treatment and cell titer glow assays after 7 days of trastuzumab treatment.
Figure 16B:
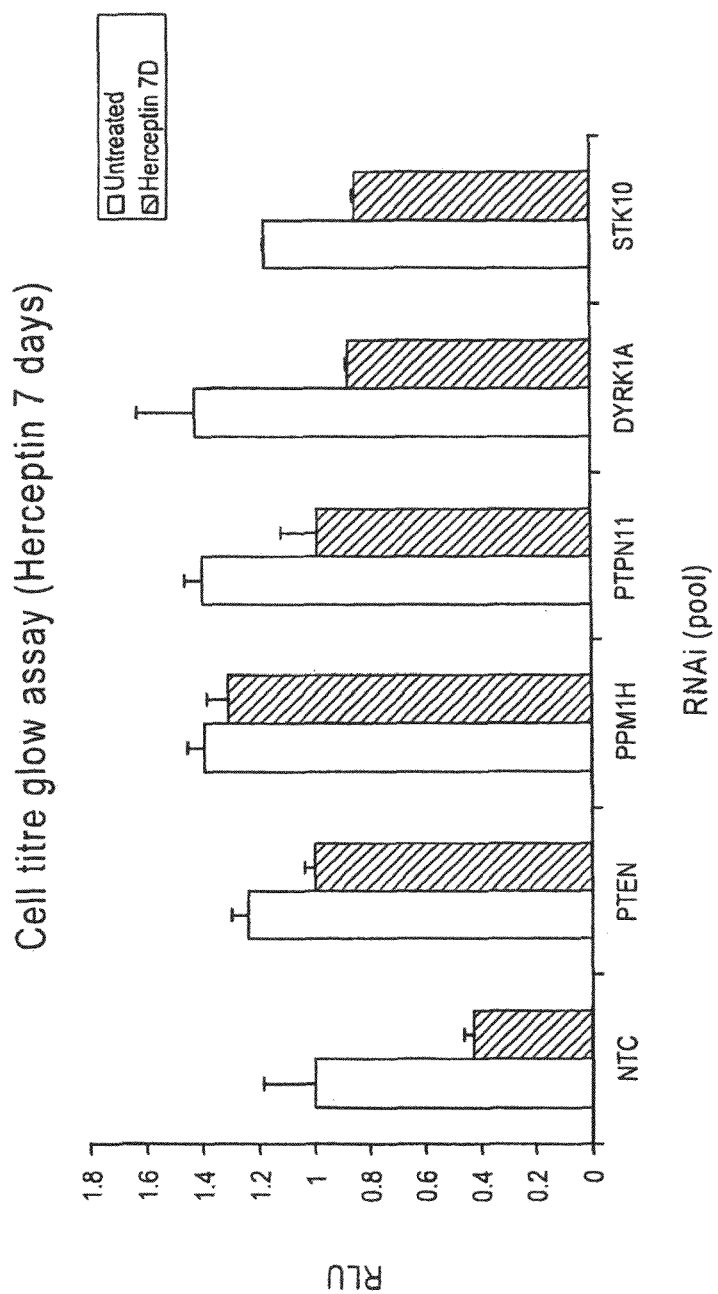
Figure 17A:
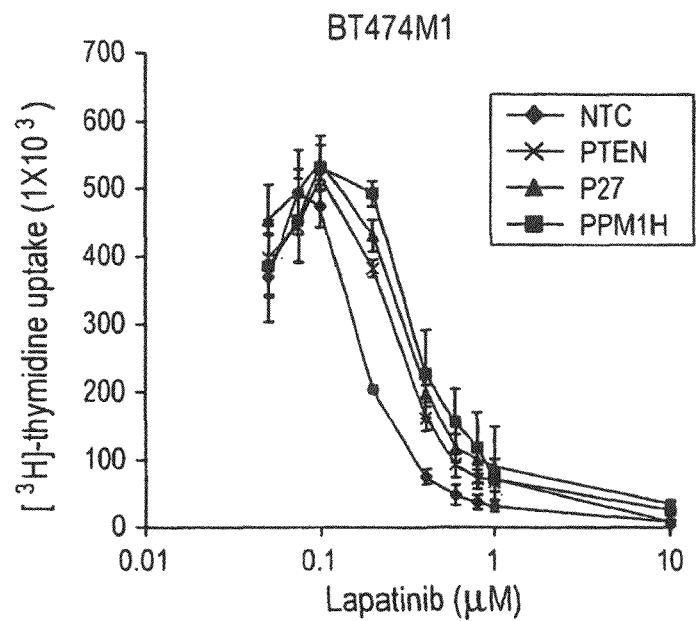
FIGS. 17A, 17B, 17C and 17D. 3H-Thymidine uptake assay of multiple HER2-amplified breast cancer cell lines by a dose range of Lapatinib treatment for 72 hours.
Figure 17B:
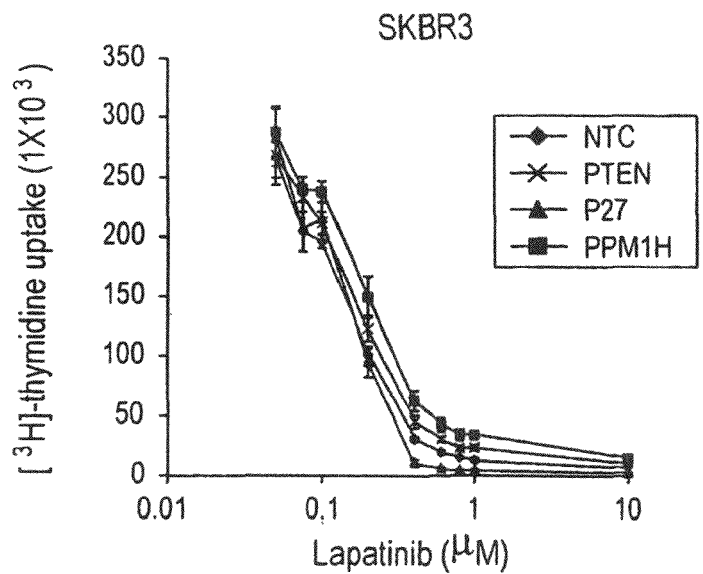
Figures 17C, 17D:
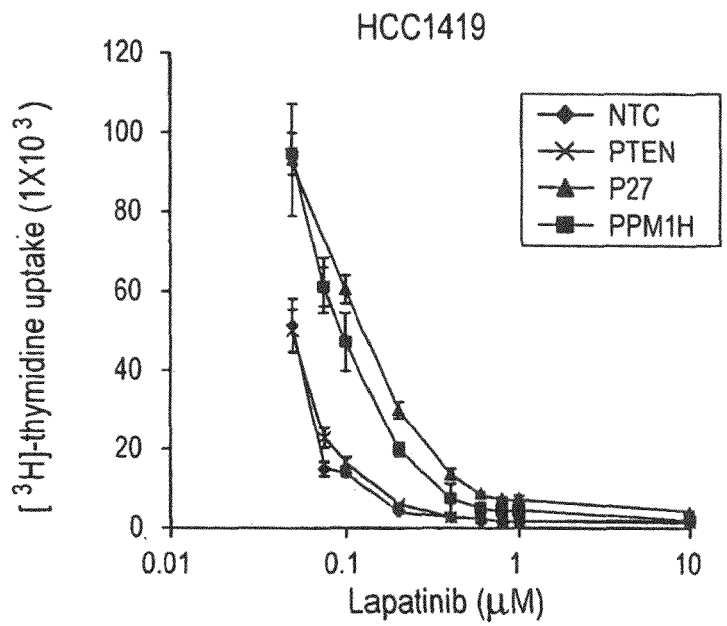

FIGS. 16A and B show that results of 3H-tymidine uptake and cell titre glow assays, and demonstrate that increased proliferation at 3 days (a) is associated with increased cell number at 7 days (b).

FIGS. 17A-D show that knockdown of the candidate genes also attenuates lapatinib response in multiple cell lines (PPM1H in particular).

Figure 18:
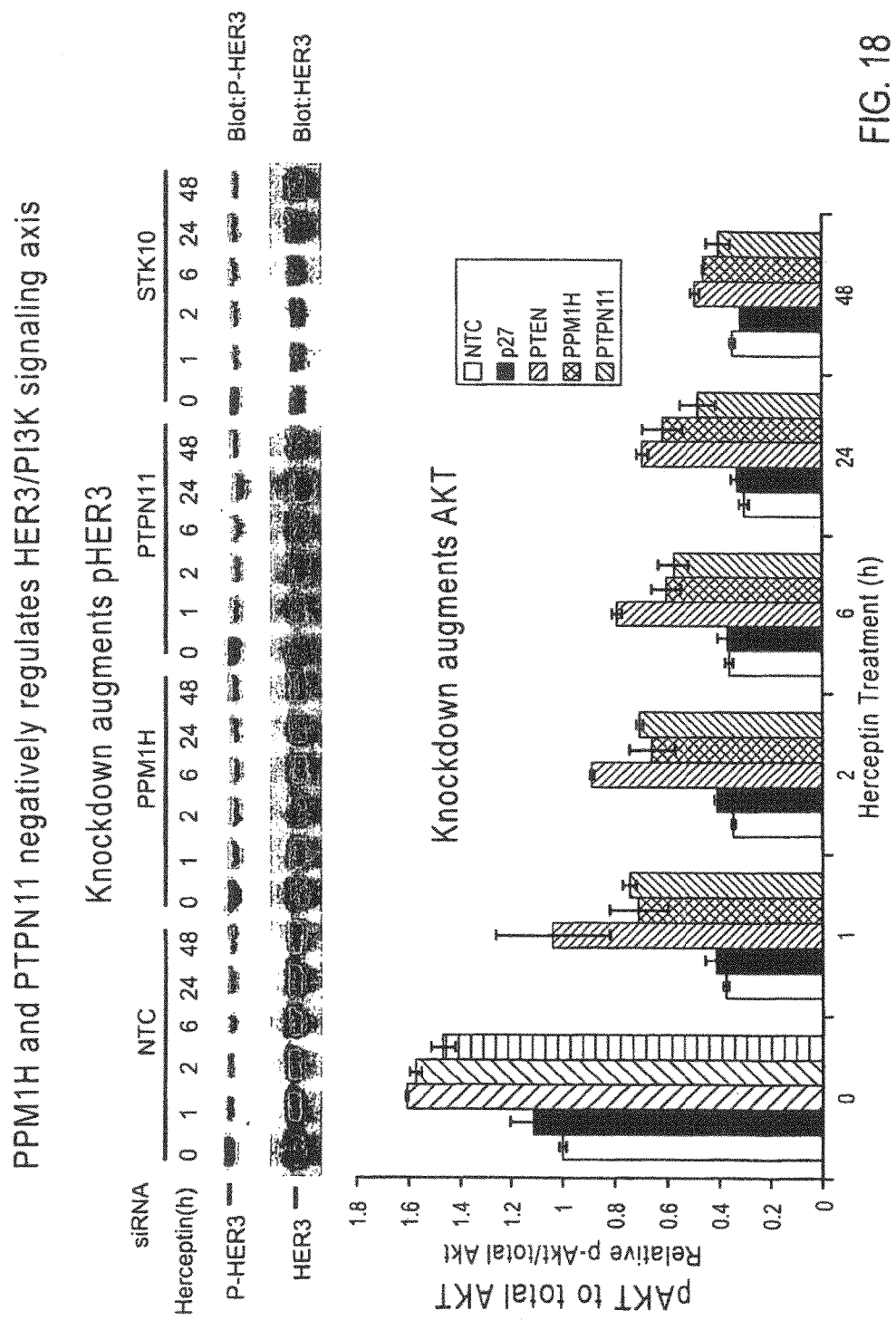
FIG. 18. Western hybridization to examine both phosphorylation level and total level of HER3 in BT474 after trastuzumab treatment over time (top). Phospho-Akt ELISA and total-Akt ELISA to measure Akt1 in BT474 cell line after treatment with trastuzumab over time (bottom).

FIG. 18 shows that PPM1H and PTPN11 negatively regulate the HER3/PI3K signaling axis.

Figure 19:
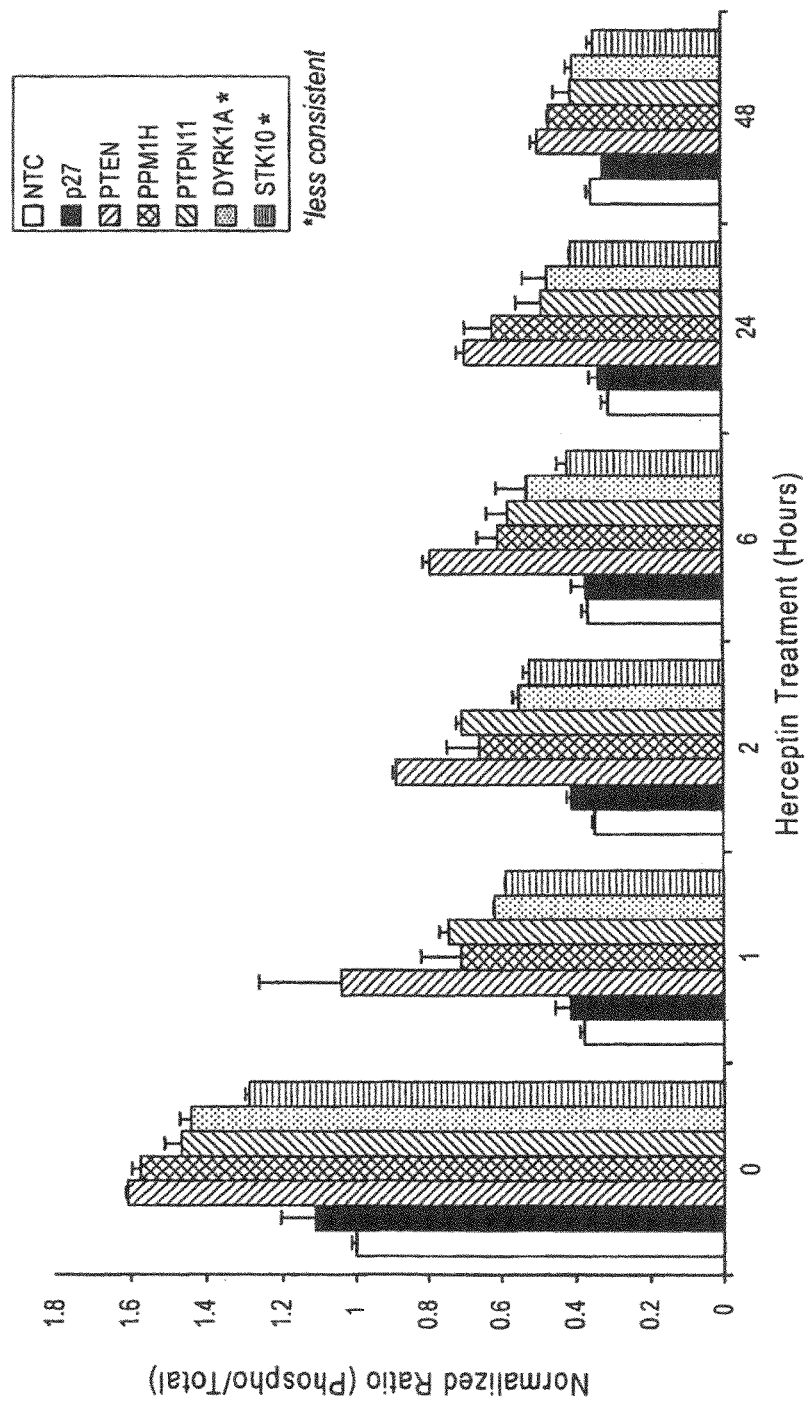
FIG. 19. Phospho-Akt ELISA and total-Akt ELISA to measure Akt1 in BT474 cells after trastuzumab treatment over time. Knockdown of all four candidate genes (PPM1H, PTPN11, DYRK1A, STK10) may increase Akt phosphorylation.

The data set forth in FIG. 19 show that knockdown of all four candidate genes (PPM1H, PTPN11, DYK1A and STK10) may increase Akt phosphorylation.

Based on these experimental data, PPM1H appears to be a particularly useful and reliable indicator of trastuzumab resistance. This molecule belongs to the protein phosphatase 2C family, and is known to play a role in other cell types, such as neurite outgrowth and putatie oncogenic role in colon adenocarcinoma. Other family members identified herein have been linked to diverse pathways, e.g., PP2Cα and β binds CDK2/CDK6; ILKAP is linked to integrin/GSK-beta signaling; PHLPP I a pAkt posphatase, and mouse PP2Cγ?FIN13 has been shown to negatively regulate growth.

Figure 20:
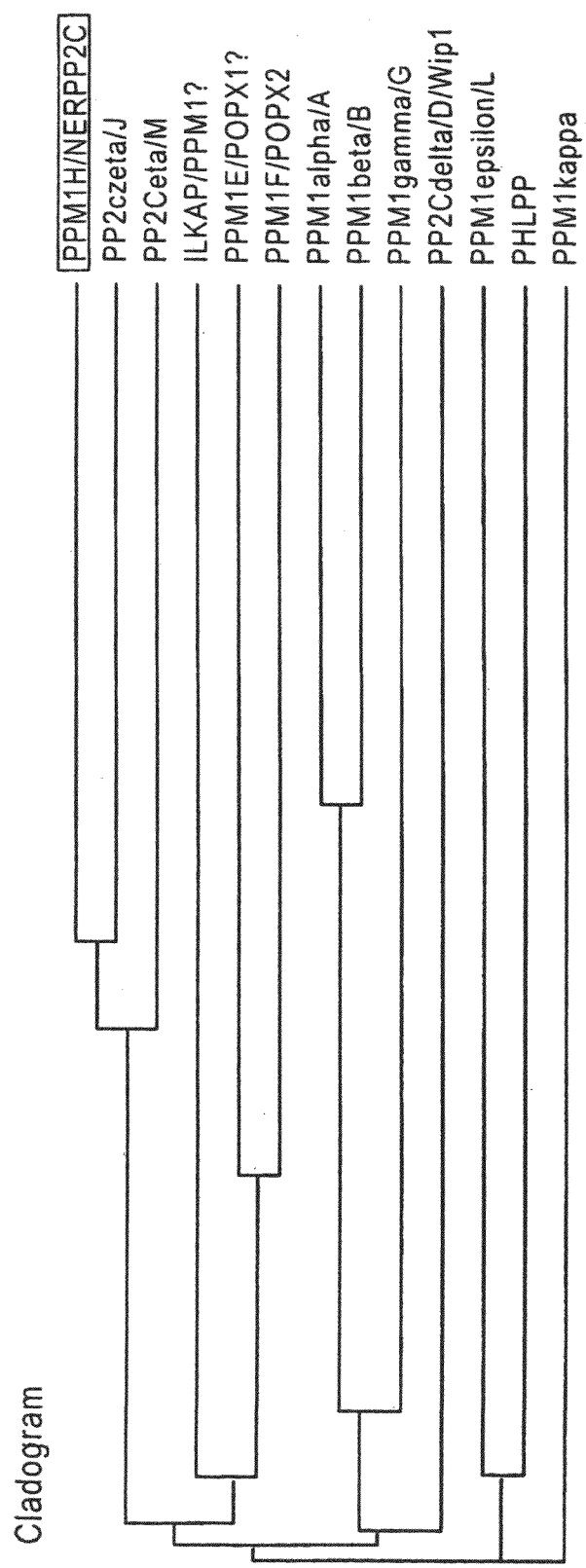
FIG. 20. Cladogram—PPM1 family members. The relative amino acid sequence similarity between other PP2C-like family members and PPM1H. By aligning amino acid sequence of the family and analyzed by computer program cluster W.

FIG. 20 is a cladogram showing PPM1 family members.

Figure 21:
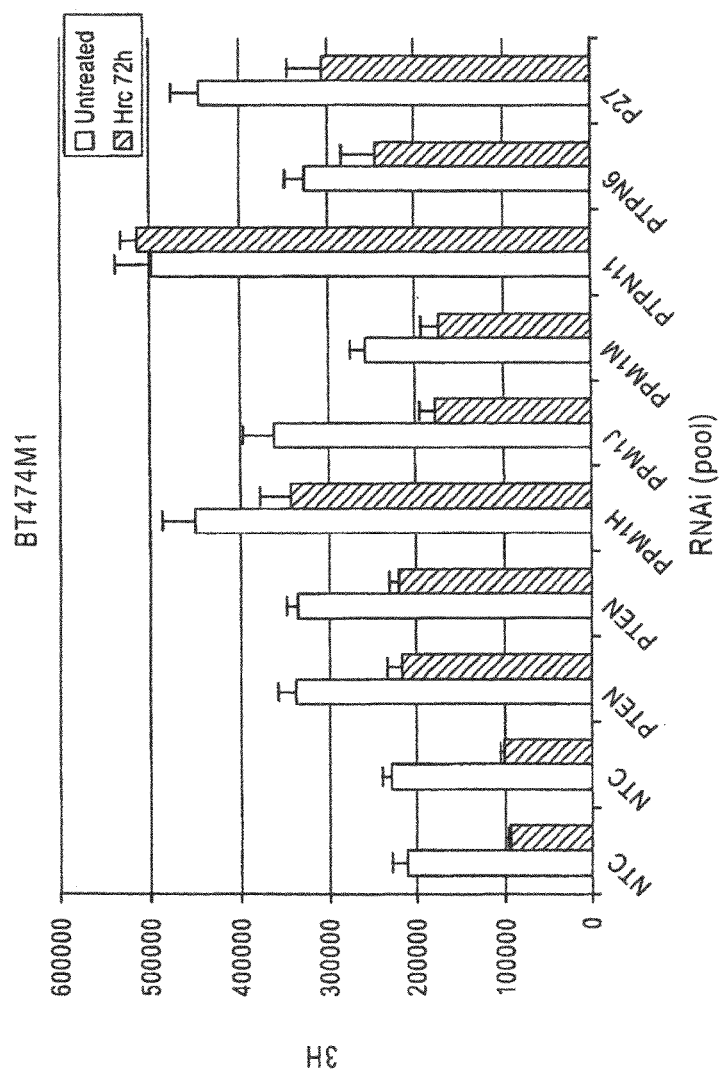
FIG. 21. 3H-Thymidine uptake assay after 72 hours of trastuzumab treatment in BT474 cell line with and without the knockdown of closely related PP2C family members PPM1H, PPM1J, PPM1M. PPM1M and PPM1J also attenuate Herceptin® response in vitro, albeit weaker than PPM1H.

FIG. 21 shows that PPM1M and PPM1J also attenuate trastuzumab response in vitro albeit weaker than PPM1H.

Figure 22:
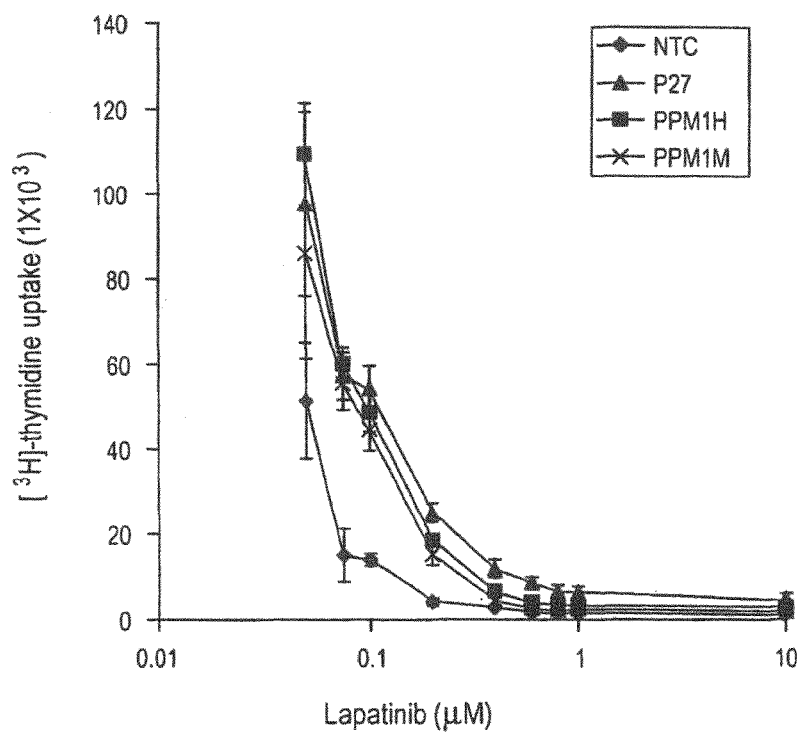
FIG. 22. 3H-Thymidine uptake assay of an HER2-amplified breast cancer cell line, HCC1419, by a dose range of Lapatinib treatment for 72 hours with and without the knockdown of closely related PP2C family members PPM1H and PPM1M. PPM1M knockdown also decreases Lapatinib response in vitro.

The results shown in FIG. 22 show that PPM1M knockdown also decreased Lapatinib response in vitro.

From these data it appears that PPM1H has similar functions to other PP2C family members. In particular, without being bound by any theory, it is believed that PPM1H may function as pAkt phosphatase similar to another family member, PHLPP to dephosphorylate P-Akt1 (S473).

However, PPM1H is also different, and may have a novel function, distinct from other PP2C family members. This new function is the modulation of signaling upstream of HER3. Thus, PP2C may function like another PP2C family member, ILKAP, to indirectly regulate GSK3/cyclin D1 signaling and thereby modulate the PI3K/Akt signaling axis downstream of pAkt.

It has been found that several genes (PTEN, CDKN1B, PPM1H, PTPN11, PPM1A, PPM1J) genes identified by the screens described in the present invention exhibit decreased expression in basal-like cell lines and tumors (see Table 2). This is of great significance, since basal-like expression has been negatively associated with poor outcome in HER2-negative patients.

EXAMPLE 2

PPM1 Loss Causes Trastuzumab Resistance

Figure 23:
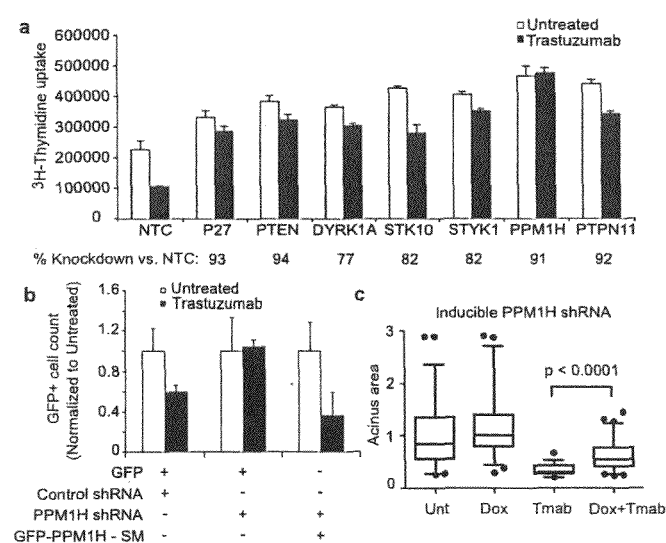
FIG. 23. Trastuzumab resistance siRNA screen identifies PPM1H. a, siRNA knockdown of 4 kinases and 3 phosphatases increased proliferation of BT474M1 cells with and without trastuzumab (mean±SEM). % knockdown measured by qRT-PCR is noted for each gene. b, PPM1H or control shRNA was transfected with a GFP vector or a GFP-PPM1H-SM vector harbouring silent mutations in the shRNA binding region. GFP-positive cells were scored with and without trastuzumab (mean±SEM). c, PPM1H knockdown with and without trastuzumab treatment was tested in 3D culture using a doxycycline inducible BT474M1-PPM1H shRNA cell line followed by measurement of acinus area. Data are represented as box and whisker plots (whiskers are $5^{th}$ and $95^{th}$ percentile).

Of the top hits identified in Example 1, knockdown of PPM stood out as being the most potent at augmenting proliferation in the presence of trastuzumab (FIG. 23a), thus we focused on better understanding the role of PPM1H in cell proliferation and trastuzumab resistance. PPM1H is a member of the PP2C family of ser/thr phosphatases distinguished by the dependence on $Mn^{2+}$ or $Mg^{2+}$ for catalytic activity (Lammers, T. & Lavi, *Crit Rev Biochem Mol Biol* 42, 437-461 (2007); Tamura, S. et al. *Cancer Sci* 97, 563-567 (2006); Stern, A. et al. Evolution of the metazoan protein phosphatase 2c superfamily. *J Mol Evol* 64, 61-70 (2007). Although, PPM1H was recently implicated as an oncogene in colon cancer (Sugiura, T. & Noguchi, Y. *Biometals* 22, 469-477 (2009); Sugiura, T., Noguchi, Y., Sakurai, K., & Hattori, C. *Cancer Biol Ther* 7, 285-292 (2008)), it was originally identified as a negative regulator of neurite outgrowth (Labes, M., Roder, J., & Roach, A. *Mol Cell Neurosci* 12, 29-47 (1998)). In fact, many PP2C family members have been described as negative regulators of growth having substrates in the PI3K pathway, the JNK pathway, or in cell cycle regulation (e.g. cyclin dependent kinases) (Lammers et al, supra; Tamura et al., supra; Stern et al., supra). Very little is known about the mechanism of PPM1H and how it might impact proliferation.

Figure 24:
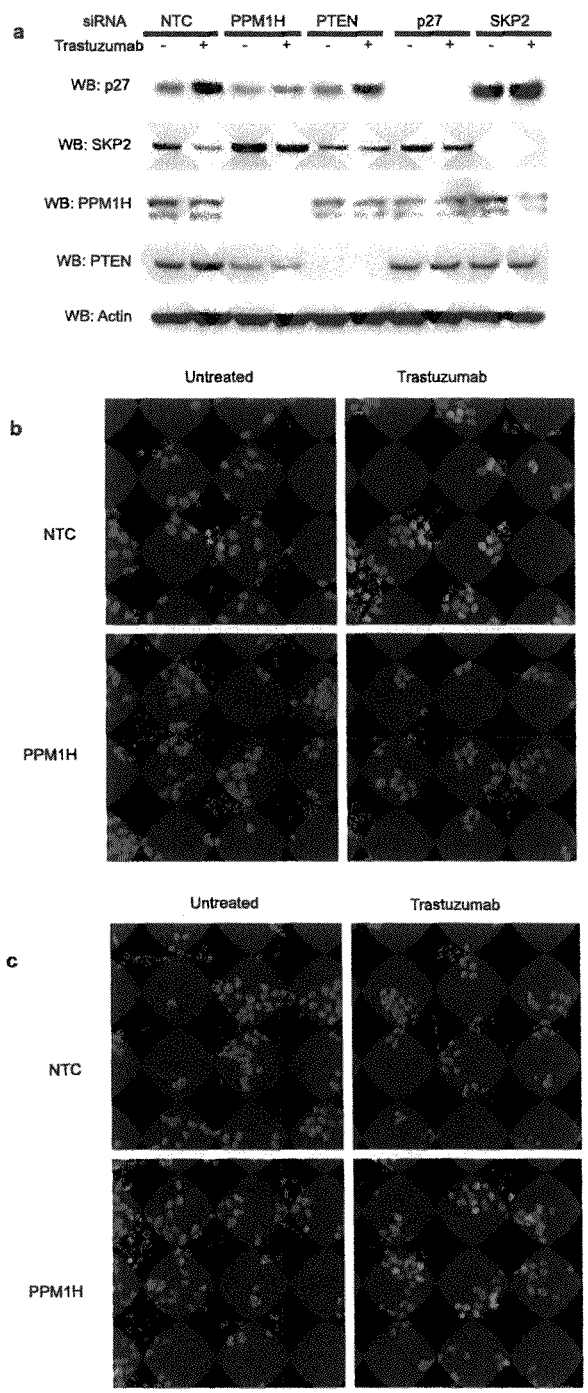
FIG. 24. PPM1H regulates expression of p27 and SKP2. a, Western blot showing expression of p27, SKP2, PPM1H, and PTEN with and without siRNA knockdown of the same genes. b, p27 immunofluorescence with and without PPM1H knockdown and with and without trastuzumab treatment. c, SKP2 immunofluorescence with and without PPM1H knockdown and with and without trastuzumab treatment.

The same phenotype was observed with 3 of 4 independent siRNA oligonucleotides targeting PPM1H, and knockdown of PPM was confirmed at the protein level (FIGS. 24 and 25), suggesting that the proliferative effect is not likely due to off-target activity. Nevertheless, to further rule out any possibility of off target effects, PPM1H shRNA was transfected into BT474M1 cells along with a control vector or a PPM1H expression vector carrying synonymous mutations within the shRNA targeted region, thus rendering the exogenous transcript resistant to knockdown. The PPM1H shRNA caused trastuzumab resistance, similar to the result with siRNA. However, when PPM1H shRNA was co-expressed with PPM1H carrying synonymous mutations, trastuzumab sensitivity was restored (FIG. 24b), providing further evidence that the observation with PPM1H is not likely due to off-target effects.

Figure 25:
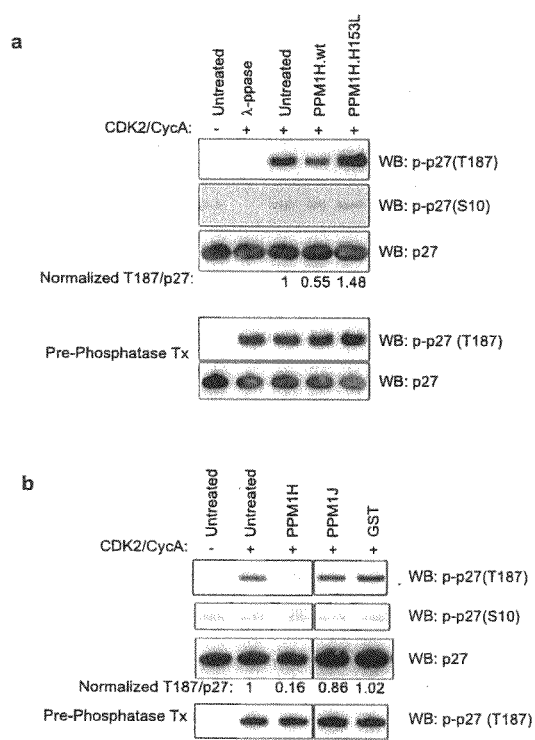
FIG. 25. PPM1H is a p27-T187 phosphatase. PPM1H activity was examined on HA-p27 produced in 293 cells. CDK2/Cyclin A (2 hours) was used to phosphorylate the T187 site of p27. One-tenth of the kinase reaction was examined to ensure equal p27 phosphorylation (Pre-Phosphatase Tx). a, flag-PPM1H and flag-PPM1H-H153L were tested in a phosphatase reaction. b, gst-PPM1H and gst-PPM1J were tested in a phosphatase reaction. The T187 and S10 phosphorylation sites were examined by Western blot.

Many studies have suggested that 3D culture may more closely mimic the milieu of a tumour mass (Weigelt, B. & Bissell, M. J. *Semin Cancer Biol* 18, 311-321 (2008)). To determine the impact of PPM1H knockdown in 3D culture, we created stable BT474M1 cell lines carrying doxycycline (dox)-inducible PPM shRNA. Treatment of the cell line with dox in 2D culture resulted in PPM1H knockdown at the mRNA and protein level and resulted in trastuzumab resistance, much like PPM1H siRNA. The same cell line was grown in 3D culture for 10 days in the presence or absence of dox, after which colony size was visualized and quantitated. In the absence of dox, trastuzumab treatment resulted in significantly smaller colony size compared to untreated colonies; in the presence of dox, the trastuzumab effect was significantly diminished (FIG. 24c). PPM1H knockdown was verified at the protein level in the 3D culture model (FIG. 25). Thus, the phenotype observed in 3D culture supports the conclusion that PPM1H knockdown augments cell growth and causes trastuzumab resistance.

EXAMPLE 3

PPM1H is a p27 T187 Phosphatase

To elucidate the molecular mechanism of PPM1H in cell proliferation, we examined the effect of PPM1H knockdown on the PI3K-Akt pathway, a key oncogenic signalling axis in HER2-amplified cells (Baselga, J. & Swain, S. M. *Nat Rev Cancer* 9, 463-475 (2009); Stern, H. M., Egfr family heterodimers in cancer pathogenesis and treatment in *Egfr signaling networks in cancer therapy*, edited by Haley, J. D. & Gullick, W. (Humana Press, 2008), Vol. 9, pp. 15-30). We speculated that the phosphatase activity of PPM1H might inactivate this pathway since PHLPP, a PPM1H-related family member, has previously been shown to dephosphorylate AKT (Brognard, J., Sierecki, E., Gao, T., & Newton, A. C. *Mol Cell* 25, 917-931 (2007)). However, knockdown of PPM1H did not change the phosphorylation levels of AKT, the downstream effectors S6, PRAS40, or GSK3β, nor the receptors HER2 or HER3 (data not shown). Furthermore, there was no evidence for modulation of the MAPK pathway as assessed by pERK.

Figure 29:
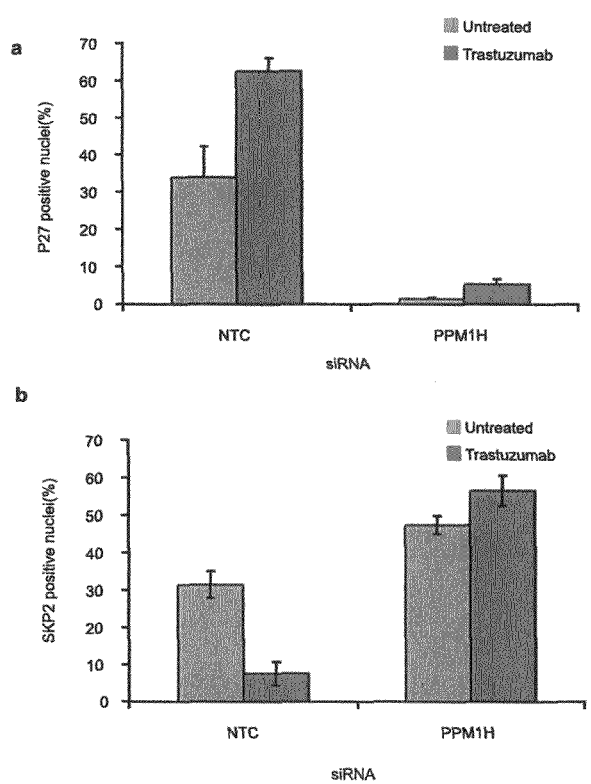
FIG. 29. Quantitation of p27 and SKP2 immunofluorescence. Images were acquired by the Ariol SL-50 automated slide scanning platform (Genetix Ltd.; Hampshire, UK) at 100× final magnification. Images were exported for analysis in the Metamorph software package (Molecular Devices, a Danaher subsidiary; Washington, DC) as individual images. Standard morphological filters were used to remove staining artifacts, and the cells were counted with the Cell Scoring application module. a, Percent of nuclei with positive staining for p27. b, Percent of nuclei with positive staining for SKP2. Error bars represent SEM.

We next examined the impact of PPM1H knockdown on cell cycle regulators including pRB, cyclin D, and p27. Only p27 protein exhibited significant modulation with PPM1H knockdown compared to both untreated and trastuzumab-treated control cells. p27 protein levels as assessed by Western blot and immunofluorescence dropped with PPM1H knockdown (FIG. 24a, b and FIG. 29), consistent with the observed increase in cell proliferation. No change in p27 mRNA levels was observed with PPM1H knockdown, suggesting that loss of p27 is due to an alteration in protein stabilization.

p27 is known to undergo ubiquitin-mediated proteasomal degradation which is initiated by phosphorylation of p27 at T187 by CDK2 in complex with cyclin A or E (Chu, I. M., Hengst, L., & Slingerland, J. M. *Nat Rev Cancer* 8, 253-267 (2008); Nakayama, K. I. & Nakayama, K. *Nat Rev Cancer* 6, 369-381 (2006)). T187 phospho-p27 is recognized by the F-box protein SKP2 which brings p27 to the COP9 signalosome (CSN) for ubiquitylation (Frescas, D. & Pagano, M. *Nat Rev Cancer* 8, 438-449 (2008)). Recently SKP2 was shown to be phosphorylated and stabilized by AKT1 at S72 (Gao, D. et al. *Nat Cell Biol* 11, 397-408 (2009); Lin, H. K. et al. *Nat Cell Biol* 11, 420-432 (2009)). However, p27 also plays a role in regulating SKP2 via inhibition of CDK2 resulting in dephosphorylation and destabilization of SKP2 (Rodier, G. et al. *Embo J* 27, 679-691 (2008)). Given this reciprocal regulation of p27 and SKP2, we hypothesized that PPM1H knockdown might be associated with increased SKP2 protein. This hypothesis was tested via Western blot and immunofluorescence, and the results clearly indicate that SKP2 protein increases while p27 decreases in the setting of PPM1H knockdown (FIG. 24a, c and FIG. 29). No change in SKP2 mRNA was observed, consistent with the conclusion that PPM1H knockdown promotes SKP2 protein stability.

Figure 30:
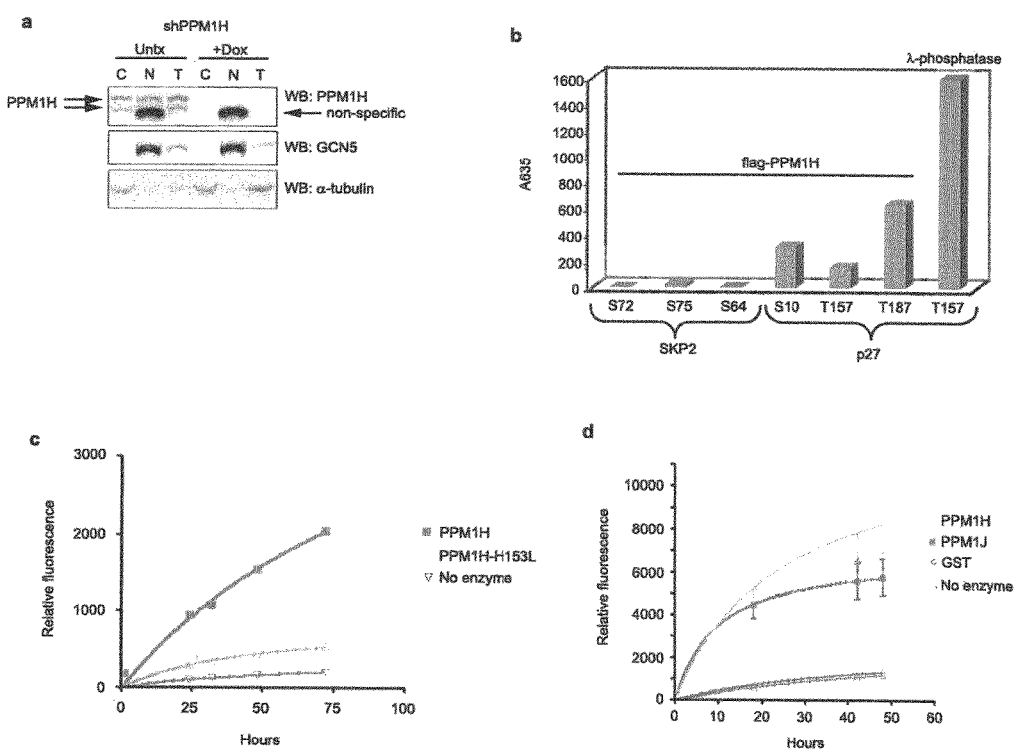
FIG. 30. PPM1H enzyme activity. a, Cells were fractionated into nuclear and cytoplasmic compartments followed by PPM1H Western blot. C, cytoplasm; N, nucleus; T, Total. b, Flag-PPM1H activity was tested on p27 and SKP2 phospho-peptides in a phosphate release assay. Phosphate release from synthetic phospho-peptides was measured using the Innova Biosciences Pi ColorLock Gold assay. Briefly 2 μg of peptide was treated with or without phosphatase in 0.1 ml 20 mM Hepes, 20 mM MgCl2, and 20 mM KCl. Absorbance of molybdate complexed free phosphate was read at A635. λ-phosphatase was used as a positive control. Activity was observed only on p27, particularly at the T187 site. c, Flag-PPM1H and flag-PPM1H-H153L were tested for activity using a synthetic phosphatase assay kit (EnzChek, Molecular Probes). d, Gst-PPM1H and gst-PPM1J were tested for activity using the EnzChek phosphatase assay kit.

Because PPM1H belongs to a ser/thr phosphatase family, it is possible that PPM1H might directly dephosphorylate p27 or SKP2. To explore these hypotheses, we first examined the subcellular localization of PPM1H. Nuclear/cytoplasmic fractionation revealed that PPM1H is present in both the nucleus and the cytoplasm (FIG. 30a). Enzymatically active recombinant flag-PPM1H was then screened for activity on in vitro synthesized phospho-peptides representing the major known phosphorylation sites on p27 (S10, T157, T187) and SKP2 (S72, S75, S64). Liberation of phosphate was observed with the p27 peptides, most notably with the T187 peptide (FIG. 30b). No evidence for PPM1H mediated dephosphorylation of the SKP2 phospho-peptides was observed.

To further examine a potential role for PPM in dephosphorylating p27, HA-tagged p27 was incubated in vitro with CDK2/cyclinA to phosphorylate T187 and was subsequently incubated with flag-PPM1H or flag-PPM1H-H153L. The H153L mutant form of PPM1H is predicted to disrupt a metal binding histidine and was found to have decreased activity in a synthetic phosphatase assay (FIG. 30c). Wild-type PPM1H but not PPM1H-H153L dephosphorylated p27 at T187 (FIG. 25a). While the S10 site on p27 was not phosphorylated by CDK2/cyclinA, there was some endogenous phosphorylation observed. PPM1H exhibited no activity at the S10 site in this assay, suggesting specificity for T187.

Specificity of PPM1H was further explored via gst tagged versions of PPM1H and the most closely related family member PPM1J. Gst-PPM1H and gst-PPM1J exhibited similar enzymatic activity in a synthetic phosphatase assay FIG. 30d), but only PPM1H was effective at dephosphorylating p27 at T187 (FIG. 25b). Neither enzyme exhibited activity at S10. Together these data further support the hypothesis that PPM is a specific p27-T187 phosphatase.

Figure 31:
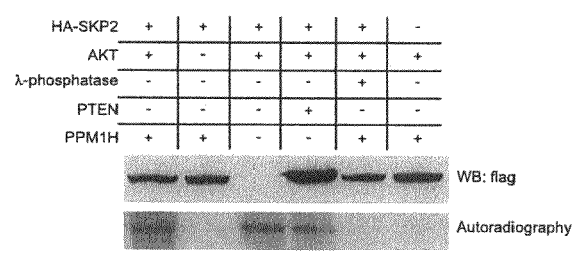
FIG. 31. AKT-phosphorylated SKP2 is not a PPM1H substrate. HA-SKP2 was incubated with AKT in a kinase reaction with $\gamma$-$^{32}$P ATP which results in radiolabeling of SKP2. The $^{32}$P-SKP2 was then incubated with λ-phosphatase as a positive control, flag-PTEN as a negative control, or flag-PPM1H. λ-phosphatase exhibited robust activity with all detectable 32P removed from SKP2. In contrast, neither PTEN nor PPM1H exhibited any evidence of phosphatase activity on SKP2.

Although PPM1H did not exhibit activity on SKP2 phosphopeptides, we nevertheless tested flag-PPM1H on full length SKP2. SKP2 was phosphorylated in vitro by AKT in the presence of g-32P-ATP and was then incubated with phosphatase. γ-phosphatase was able to dephosphorylate SKP2 but PPM1H lacked activity (FIG. 31). These data further support the conclusion that unlike p27, SKP2 is not a substrate for PPM1H.

EXAMPLE 4

PPM1H and Clinical Outcome on Trastuzumab

Figure 26:
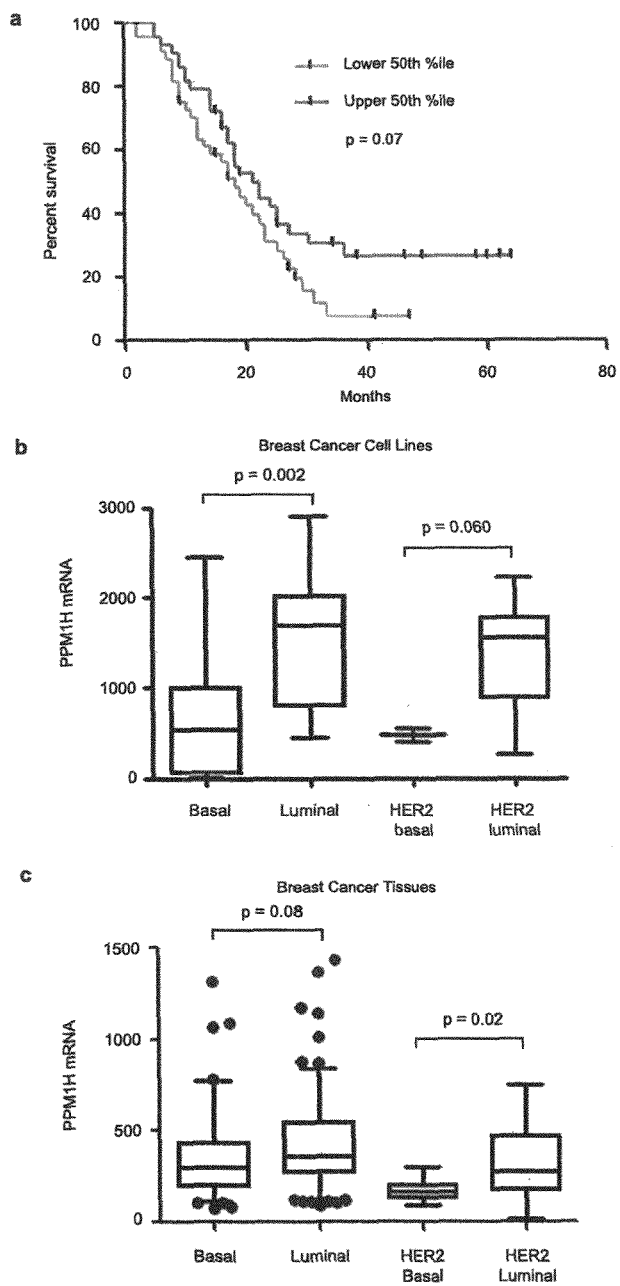
FIG. 26. Low PPM1H expression is associated with poor clinical outcome. a, PPM1H was assessed by isotopic in situ hybridization in tumour tissue from 87 metastatic breast cancer patients treated with trastuzumab. Using the median as a cutoff, Kaplan-Meier analysis reveals a hazard ratio of 1.60 for low PPM1H (p=0.07, 95% CI 0.96-2.65). b, Breast cancer cell lines were subgrouped into basal and luminal (Sorlie, T. et al. *Proc Natl Acad Sci USA* 98, 10869-10874 (2001)). PPM1H expression was examined in basal compared to luminal cell lines and further divided into those that do or do not overexpress HER2. c, PPM1H expression was examined in 261 breast tumours subgrouped into basal and luminal (Sorlie et al, supra) and HER2-positive vs. HER2-negative.
Figure 27:
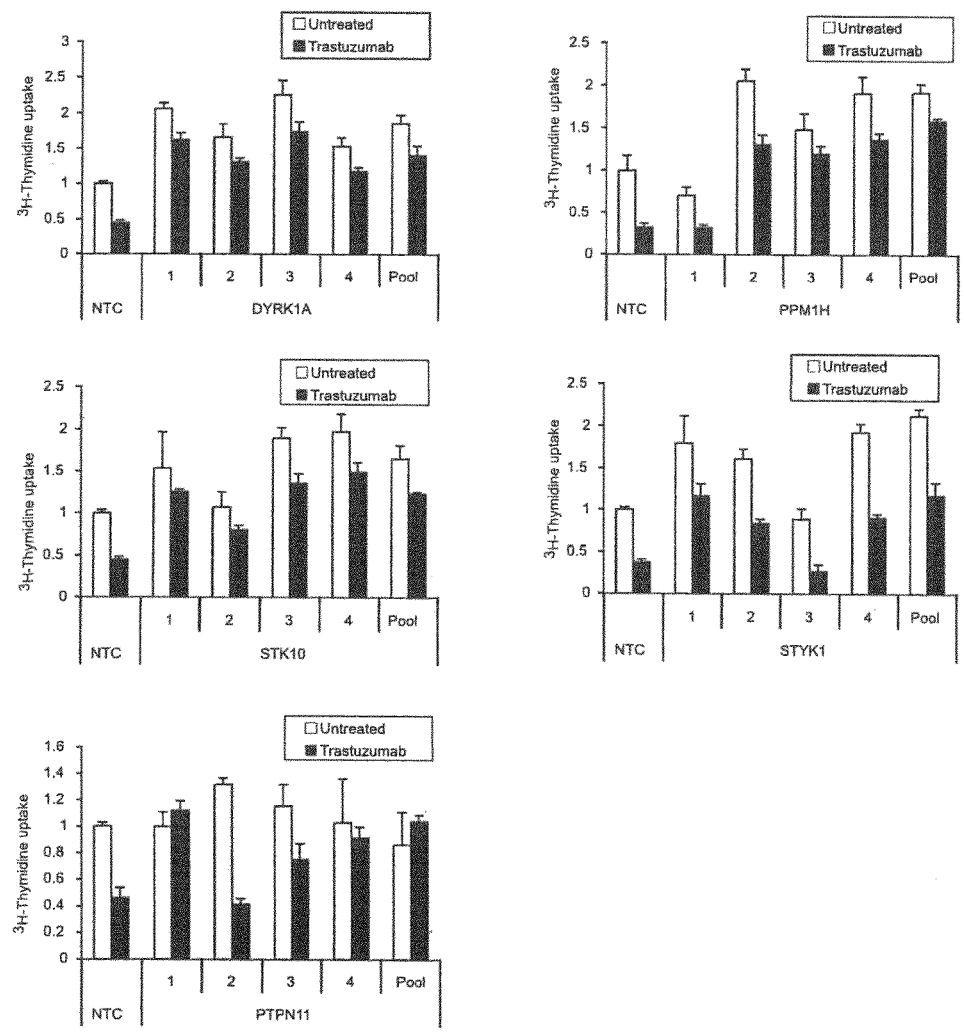
FIG. 27. Summary of individual siRNA data. Data for each of the 4 siRNA oligonucleotides and the pool are summarized for each of the top 5 novel hits in the screen.
Figure 28:
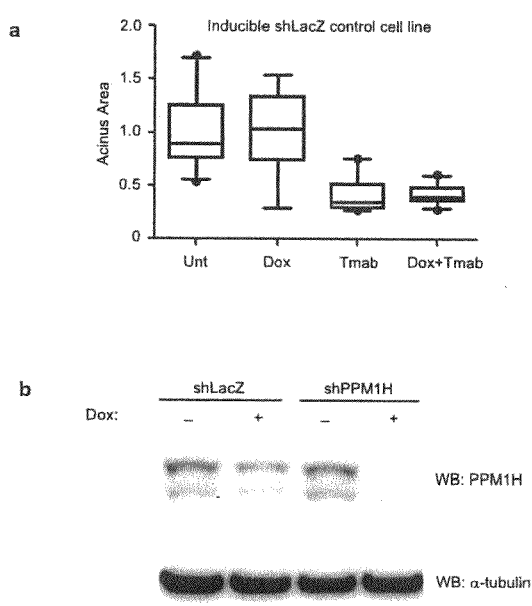
FIG. 28. Controls for assessing PPM1H in 3D culture. a, In parallel with the data shown in FIG. 1, we included a dox inducible shLacZ cell line as a negative control and saw no difference in the effect of trastuzumab with and without dox administration. Phase contrast images were quantified using the Metamorph software package (Molecular Devices, a Danaher subsidiary; Washington, DC). Briefly, a bottom hat filter was used to correct for non-uniform illumination to allow for a binary threshold to identify cell-specific regions. Sequential opening and closing was then performed to consolidate cells and remove small non-cellular debris. b, Western blot showing PPM1H knockdown with dox administration in the 3D culture model.

To explore whether expression of PPM1H might impact clinical outcome on trastuzumab, we developed an isotopic in situ hybridization probe to assay PPM1H mRNA in FFPE human breast cancer samples. PPM1H was examined in 87 HER2-amplified patients who had been treated with trastuzumab. The sample set consisted of a mixture of first-line, second-line, and later-line patients from British Columbia, most of whom were treated with trastuzumab in combination with chemotherapy as previously described (Robinson, A. G. et al. *Clin Breast Cancer* 7, 254-261 (2006)). PPM1H expression was scored via two methods. In the first, a pathologist gave a semi-quantitative assessment of expression in invasive neoplastic cells on a 0, 1+, 2+, 3+ scale. In the second, areas enriched in invasive neoplastic cells were marked by a pathologist and a quantitative phosphor-imager analysis of PPM1H expression was performed. With both scoring methods, there was a strong trend toward poor outcome with low PPM1H expression (hazard ratio 1.6), although the data did not quite reach statistical significance (p=0.07, 95% CI 0.96-2.6) (FIG. 26a and Supplementary FIG. 8a). These data suggest that low PPM1H expression could be a poor prognostic indicator in HER2-positive patients treated with trastuzumab.

Figure 32:
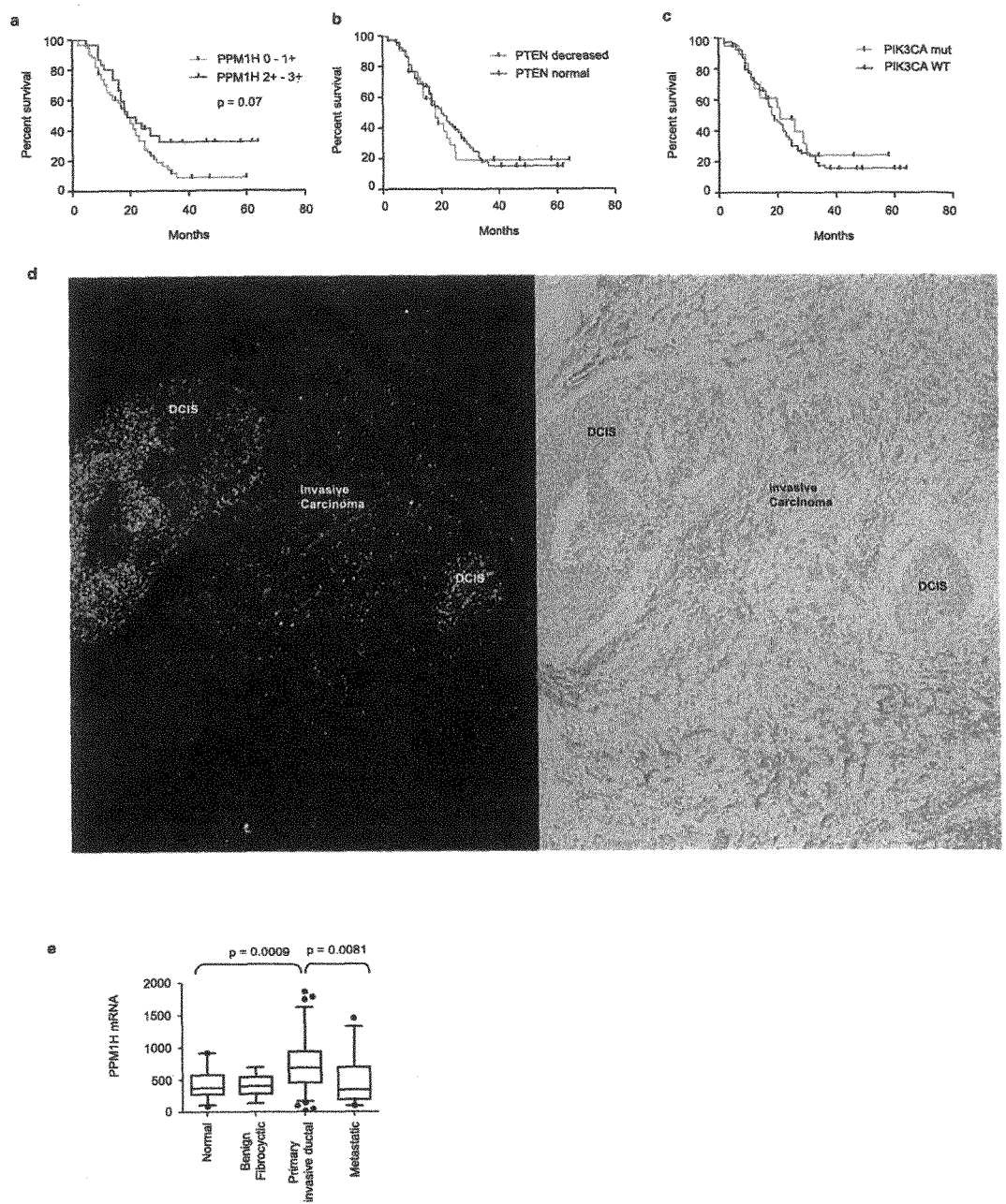
FIG. 32. PM1H expression in breast tissues. a, PPM1H in situ hybridization was performed as noted in FIG. 5. In addition to a quantitative analysis, the samples were scored by a pathologist on a 0, 1+, 2+, 3+ scale. A Kaplan-Meier analysis comparing 0 and 1+ versus 2+ and 3+ was performed. The hazard ratio was 1.58 for low PPM1H expression with a p-value of 0.07 (95% CI 0.96-2.60), very similar to the quantitative analysis. b, PTEN IHC was performed on the Ventana Discovery platform using a tissue microarray representing the same samples included in the PPM1H analysis. The IHC was scored by comparing staining in tumour cells to staining in normal tissue elements. Samples with decreased staining in tumour were considered to have decreased PTEN expression (33%). In a Kaplan-Meier analysis, there was no statistically significant difference in outcome based on PTEN status. c, PIK3CA hotspot mutations (H1047, E545, E542) were assessed by Sequenome mass spectrometry. 21% of samples were mutant. Kaplan-Meier analysis reveals no significant difference in outcome based on PIK3CA mutation status. d, Image of in situ hybridization and H&E of one sample with increased PPM1H expression in DCIS, but low expression in invasive carcinoma. e, PPM1H expression in breast tissue samples including normal, benign disease, invasive cancer and metastasis. Expression data were derived from Affymetrix HGU-133A and HGU-133B arrays and were normalized using the MAS 5.0 algorithm.

To determine if the observation with PPM1H was independent from known PI3K pathway prognostic markers, we examined PTEN expression and PIK3CA mutation status in the same trastuzumab-treated cohort. Low PPM1H expression was independent of PIK3CA mutation and PTEN expression status. Interestingly, in this sample set, neither decreased PTEN expression nor PIK3CA hotspot mutations were associated with poor outcome either alone or in combination (FIGS. 32b and 32c). While it is not clear why these PI3K pathway alterations did not trend towards predicting worse outcome, it is of potential significance that PPM1H did exhibit a trend in the same sample set.

In all cases in this cohort, PPM1H expression was observed to be low in normal breast epithelium and stroma, but appeared to be elevated in the epithelium of a proportion of the invasive breast cancers. In one case, PPM1H was observed to be elevated in pre-malignant glands (ductal carcinoma in situ), but was low in adjacent invasive cancer (FIG. 32d). This observation raises the possibility that PPM1H is upregulated earlier in the oncogenic process and in some cases is later downregulated. To further explore this possibility, we examined PPM1H expression in a panel of 192 breast tissues that had undergone expression profiling. Although ductal carcinoma in situ was not included in this sample set, there was evidence for elevated PPM1H expression in some primary tumours compared to normal and benign fibrocystic breast tissue. However, metastatic tumour tissue exhibited decreased PPM1H expression compared to primary tumours (FIG. 32e). These data are consistent with a conclusion that PPM1H expression tends to be increased in early stages of disease and is decreased at later stages.

PPM1H mRNA was also examined in a set of cell lines and cancer tissues representing the major breast cancer subtypes. The basal-like subtype tends to lack expression of ER, PR and HER2 and is associated with poor prognosis (Perou, C. M. et al. *Nature* 406, 747-752 (2000); Sorlie, T. et al. *Proc Natl Acad Sci USA* 98, 10869-10874 (2001); Sorlie, T. et al. *Proc Natl Acad Sci USA* 100, 8418-8423 (2003)). The luminal subtype expresses ER and PR, lacks HER2 amplification and is associated with a better prognosis. While HER2 positive cancers are typically treated as a single subtype, there are reports that this group can be further subdivided into HER2-basal and HER2-luminal, with HER2-basal exhibiting a worse prognosis (Neve, R. M. et al. *Cancer Cell* 10, 515-527 (2006); Liu, H. et al. *Hum Pathol* 39, 167-174 (2008)). Interestingly, breast cancer cell lines classified as basal or HER2-basal exhibited lower levels of PPM1H than did the luminal counterparts (FIG. 26b). A similar observation was made in breast cancer tissues (FIG. 26c).

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

All references cited throughout the specification, and the references cited therein, are hereby expressly incorporated by reference in their entirety.

What is claimed is:

1. A method of predicting the likelihood of response of a mammalian subject diagnosed with or at risk of developing a HER2 expressing tumor to treatment with a HER2 inhibitor, comprising
   (a) measuring in a tumor cell sample obtained from said human subject, an identical or increased expression level of the RNA transcript or expression product of a PPM1H gene relative to the expression level of PPM1H gene in a normal cell of the same cell type, wherein the identical or increased expression level identifies the subject as not likely to be resistant to treatment with trastuzumab, and
   (b) treating the subject with trastuzumab.

2. The method of claim 1 wherein the tumor is selected from the group consisting of breast cancer, squamous cell cancer, small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, and head and neck cancer.

3. The method of claim 1 wherein the tumor is selected from the group consisting of carcinomas of the stomach, endometrium, salivary gland, lung, kidney, colon, thyroid, pancreas and bladder, and prostate cancer.

4. The method of claim 1 wherein the tumor is breast cancer.

5. The method of claim 4 wherein the tumor is metastatic breast cancer.

6. The method of claim 1 wherein the tumor cell sample is from a fixed, wax-embedded cancer tissue specimen of said patient.

7. The method of claim 1 wherein the tumor cell sample is a core biopsy tissue.

8. The method of claim 1 wherein said tumor cell sample is from a biological fluid.

9. The method of claim 8 wherein the biological fluid is selected from the group consisting of blood, urine, saliva, ascites fluid, blood serum and blood plasma.

10. The method of claim 1, wherein measurement of the expression level is implemented using an apparatus adapted to determine the expression level of said RNA transcript or said expression products.

11. The method of claim 10, wherein the measurement of the expression levels is performed by using a software program executed by a suitable processor.

12. The method of claim 11, wherein the program is embodied in software stored on a tangible medium.

13. The method of claim 12, wherein the tangible medium is selected from the group consisting of a CD-ROM, a floppy disk, a hard drive, a DVD, and a memory associated with the processor.

14. The method of any one of claims 10 to 13, further comprising the step of preparing a report recording the results of said measurement.

15. The method of claim 14, wherein said report is recorded or stored on a tangible medium.

16. The method of claim 15, wherein the tangible medium is paper.

17. The method of claim 15, wherein the tangible medium is selected from the group consisting of a CD-ROM, a floppy disk, a hard drive, a DVD, and a memory associated with the processor.

18. The method of any one of claims 10 to 17, further comprising the step of communicating the results of said determination to an interested party.

19. The method of claim 18, wherein the interested party is the patient or the attending physician.

20. The method of claim 18 or claim 19, wherein the communication is in writing, by email, or by telephone.

* * * * *

SEQUENCE LISTING

```
<160> NUMBER OF SEQ ID NOS: 14

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (10)
<223> OTHER INFORMATION: /replace="Ser"
<220> FEATURE:
<221> NAME/KEY: misc_feature
<222> LOCATION: (10)
<223> OTHER INFORMATION: /note="Residue given in the sequence have no
      preference with respect to those in the annotation for said
      position"

<400> SEQUENCE: 7

Gly Phe Thr Phe Thr Asp Tyr Thr Met Asp
 1               5                  10

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

```
Asp Val Asn Pro Asn Ser Gly Gly Ser Ile Tyr Asn Gln Arg Phe Lys
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Leu Gly Pro Ser Phe Tyr Phe Asp Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ala Ser Gln Asp Val Ser Ile Gly Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (5)
<223> OTHER INFORMATION: /replace="Leu"
<220> FEATURE:
<221> NAME/KEY: VARIANT
<222> LOCATION: (6)
<223> OTHER INFORMATION: /replace="Glu"
<220> FEATURE:
<221> NAME/KEY: VARIANT
<222> LOCATION: (7)
<223> OTHER INFORMATION: /replace="Ser"
<220> FEATURE:
<221> NAME/KEY: misc_feature
<222> LOCATION: (5)..(7)
<223> OTHER INFORMATION: /note="Residues given in the sequence have no
      preference with respect to those in the annotations for said
      positions"

<400> SEQUENCE: 11

Ser Ala Ser Tyr Arg Tyr Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Tyr Tyr Ile Tyr Pro Tyr Thr
1               5
```

```
<210> SEQ ID NO 13

<400> SEQUENCE: 13

000

<210> SEQ ID NO 14

<400> SEQUENCE: 14

000
```